United States Patent
Kurdowska

(10) Patent No.: US 9,982,265 B2
(45) Date of Patent: May 29, 2018

(54) INHIBITION OF BRUTON'S TYROSINE KINASE (BTK) IN THE LUNG TO TREAT SEVERE LUNG INFLAMMATION AND LUNG INJURY

(71) Applicant: BOARD OF REGENTS, THE UNIVERSITY OF TEXAS SYSTEM, Austin, TX (US)

(72) Inventor: Anna Kurdowska, Whitehouse, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days. days.

(21) Appl. No.: 15/129,956

(22) PCT Filed: Mar. 30, 2015

(86) PCT No.: PCT/US2015/023267
§ 371 (c)(1),
(2) Date: Sep. 28, 2016

(87) PCT Pub. No.: WO2015/149056
PCT Pub. Date: Oct. 1, 2015

(65) Prior Publication Data
US 2017/0175125 A1    Jun. 22, 2017

Related U.S. Application Data

(60) Provisional application No. 61/971,784, filed on Mar. 28, 2014.

(51) Int. Cl.
| | | |
|---|---|---|
| *C07H 21/02* | (2006.01) | |
| *C07H 21/04* | (2006.01) | |
| *C12N 15/113* | (2010.01) | |
| *A61K 31/713* | (2006.01) | |
| *A61K 31/519* | (2006.01) | |
| *A61K 9/00* | (2006.01) | |
| *A61K 47/48* | (2006.01) | |

(52) U.S. Cl.
CPC ........ *C12N 15/1137* (2013.01); *A61K 9/0043* (2013.01); *A61K 31/519* (2013.01); *A61K 31/713* (2013.01); *A61K 47/484* (2013.01); *A61K 47/48561* (2013.01); *C12N 2310/14* (2013.01); *C12N 2310/3513* (2013.01); *C12N 2320/31* (2013.01); *C12N 2320/32* (2013.01)

(58) Field of Classification Search
CPC ..... A61K 48/00; A61K 31/713; C12N 15/113
See application file for complete search history.

(56) References Cited

U.S. PATENT DOCUMENTS

| | | | |
|---|---|---|---|
| 2005/0255120 A1 | 11/2005 | Simon | |
| 2005/0260214 A1 | 11/2005 | Simon | |
| 2013/0052731 A1* | 2/2013 | Ma .................. | C07K 1/1077 435/375 |
| 2013/0129752 A1 | 5/2013 | Peer et al. | |
| 2013/0178461 A1* | 7/2013 | Berthel ............ | C07D 401/14 514/210.21 |
| 2014/0175018 A1* | 6/2014 | Winqvist .......... | A61M 1/3679 210/691 |

FOREIGN PATENT DOCUMENTS

| | | | | |
|---|---|---|---|---|
| CA | 2829669 | * | 4/2015 | ........... C12N 15/113 |
| WO | 2008077022 A2 | | 6/2008 | |
| WO | 2008110624 A2 | | 9/2008 | |
| WO | 2009102782 A2 | | 8/2009 | |
| WO | 2011133609 A2 | | 10/2011 | |
| WO | 2012006083 A2 | | 1/2012 | |
| WO | 2013157021 A1 | | 10/2013 | |
| WO | 2015026934 A1 | | 2/2015 | |

OTHER PUBLICATIONS

Kunihiko Hiraiwa et al., Nature and Consequences of the Systemic Inflammatory Response Induced by Lung Inflammation, INTECH, p. 1-33 (2014).

(Continued)

*Primary Examiner* — Amy H Bowman
(74) *Attorney, Agent, or Firm* — Browdy and Neimark, PLLC

(57) ABSTRACT

Bruton's tyrosine kinase (Btk) plays an important role in the pathophysiology of local inflammation in acute lung injury (ALI)/acute respiratory distress syndrome (ARDS). A unique two hit model of ALI induced by lipopolysaccharide (LPS)/immune complex (IC)—was developed, along with viral-induced ALI caused by influenza virus and COPD caused by second hand smoke. Two types or therapeutics (i) Anti-neutrophil antibodies, and specifically their F(ab')$_2$ fragments conjugated to Btk-specific siRNA or (ii) small molecule Btk inhibitors were administered to lungs and silenced or inhibited Btk specifically in alveolar neutrophils. Such silencing/inhibition had a dramatic protective effect lung damage induced by LPS/IC, influenza virus and on COPD. Btk regulates neutrophil survival and clearance of apoptotic neutrophils in these diseases. Btk-targeted neutrophil-specific therapy restores homeostasis in lungs of patients with ALI/ARDS, acute lung infection, COPD and other lung diseases.

18 Claims, 34 Drawing Sheets

(56) References Cited

OTHER PUBLICATIONS

M. Perl et al., "Epithelial Cell Apoptosis and Neutrophil Recruitment in Acute Lung Injury—A Unifying Hypothesis? What We Have Learned from Small Interfering RNAs", Mol Med, pp. 465-475 (Jul. 2008).

B. Yu et al., "Targeted Delivery Systems for Oligonucleotide Therapeutics", The AAPS Journal, pp. 195-203, vol. 11, No. 1 (Mar. 2009).

M. Zafra et al., "Gene Silencing of SOCS3 by siRNA Intranasal Delivery Inhibits Asthma Phenotype in Mice", PLoS One, pp. 1-11, vol. 9, No. 3 (Mar. 2014).

* cited by examiner

INFLUENZA

INHIBITION OF BRUTON'S TYROSINE KINASE (BTK) IN THE LUNG TO TREAT SEVERE LUNG INFLAMMATION AND LUNG INJURY

BACKGROUND OF THE INVENTION

Field of the Invention

The invention in the field of biochemistry, molecular biology and medicine relates to the treatment of severe lung inflammation and acute lung injury (ALI) by inhibition of Bruton's tyrosine kinase (Btk) in the lung using small inhibitory RNA (siRNA) that silences Btk expression or small molecule inhibitors of Btk.

Description of the Background Art

Acute lung injury/acute respiratory distress syndrome (ALI/ARDS) is a life threatening inflammatory disease with mortality of 30 to 50%. One of the characteristic features of ALI/ARDS is a significant increase in the migration of neutrophils to lungs (18, 32, 34, 53). Multiple studies indicate a correlation between the number of neutrophils in the alveolar spaces and the resulting severity of the disease. Even though ARDS can develop in neutropenic patients, these individuals constitute a distinct minority of all ARDS cases, and, moreover, neutrophils contribute to the deterioration of lung function in patients recovering from neutropenia (4, 42). In this regard, K. Y. Yang et al. found that the early activation status of neutrophils in patients with ALI determines the clinical course of the disease (57). Many animal models of ALI are linked to presence of elevated concentrations of neutrophils (1, 11, 19, 49). Together these observations suggested to the present inventor that neutrophils may play a central role in the pathogenesis of most cases of clinical ALI/ARDS.

Both neutrophil apoptosis and the phagocytic uptake of apoptotic neutrophils (efferocytosis) are decreased at sites of pulmonary inflammation in ALI/ARDS. Impaired clearance of activated neutrophils in lungs of patients with ALI/ARDS leads to excessive accumulation of these cells at the site of inflammation and may promote lung injury (33, 35, 36).

Previous studies from the present inventor's laboratory presented a novel concept in the field of human ALI/ARDS, i.e., that Btk-associated pathways may play an important role in the pathophysiology of ALI/ARDS by influencing local inflammation (25). Btk, a Tec kinase, belongs to a family of non-receptor intracellular tyrosine kinases (38) which includes the structurally homologous kinases Btk, Tec, Itk, Bmx, and Txk. Tec kinases typically reside in an inactive form in the cytoplasm, and are translocated to the membrane fraction upon cell stimulation where they initiate down-stream signaling cascades (48).

The inactive form of Btk resides in the cytoplasm. Once activated, Btk typically migrates to the cell membrane (25, 48). Btk has been primarily studied in B lymphocytes where the engagement of the B cell receptor leads to its phosphorylation (7, 22). In human neutrophils Btk mediates signaling via toll-like receptor-4 (TLR4 receptor) and G-protein-coupled receptor (16, 55). Moreover, recent studies have shown that engagement of FcγRIIa receptors by immune complexes can also trigger Btk activation in these cells (25).

The present inventor and colleagues also noted (25) that there is cross talk between FcγRIIa and TLR4 in alveolar neutrophils from patients with ALI/ARDS and that Btk mediates the molecular cooperation between these two receptors. To study cross talk between TLR4 and FcγRIII (mouse equivalent of human FcγRIIa; 5, 15, 41) in vivo, they developed a unique two hit model of ALI (lipopolysaccharide (LPS)/immune complex (IC)-induced ALI). LPS was used because sepsis is a major risk factor for development of ALI/ARDS (34). In addition, since the previous studies showed that anti-KC:KC ICs (KC is an abbreviation for C-X-C motif ligand 1 or CXCL1) contribute in a significant way to severe lung inflammation in LPS treated mice (28), the inventor also employed anti-KC antibody:KC (anti-KC: KC) ICs. These studies with animal models of ALI as well as clinical samples from ALI/ARDS patients indicate that LPS dependent signaling induces a significant increase in the level of ICs in the alveolar compartment. Therefore a model was chosen that involves the combined effects of LPS and immune complexes to closely mimic the situation in patients with ALI. In summary, this model reflects very well the sequence of the pro-inflammatory events in patients with ALI, where the initial insult (such as LPS) triggers production of pathogenic ICs (3, 14, 26-30).

Infection with the influenza ("Flu") virus triggers the rapid recruitment of neutrophils to the alveolar compartment, where these cells play an important role in host defense by controlling viral replication and clearing dying cells. Mounting evidence supports the contribution of neutrophils to the excessive acute inflammatory responses that cause severe lung immunopathology during Flu infection (D. Damjanovic et al., *Clin. Immunol.* 144:57-69, 2012; M N Ballinger et al. *J. Interferon Cytokine Res.* 30:643-652, 2010; B. Amulic et al. *Annu. Rev. Immunol.* 30:459-89, 2012).

In view of the present inventors' recent discoveries that engagement of FcγRIIa receptors by immune complexes can trigger activation of Btk in neutrophils (25) and their discovery disclosed herein that silencing Btk in neutrophils in lungs had a dramatic protective effect on in LPS/immune complex-induced ALI studies were directed to the role of Btk and the therapeutic effect of its silencing in influenza A induced ALI and in a mouse model of emphysema/chronic obstructive pulmonary disease (COPD).

COPD is the fourth leading cause of death worldwide. The inflammatory response to cigarette smoke appears to be the major etiological factor in the pathogenesis of COPD and exposure to second hand smoke (SHS) activates an inflammatory cascade in the lungs. At present, casual interventions that can stop progression of COPD are not available primarily because of the lack of thorough understanding of the mechanism underlying the development and natural course of this disease. Indeed specific pathways/mediators that drive the induction and progression of chronic inflammation, emphysema and altered lung function are not known. Therefore, there is a clear need in the art for new therapies that can prevent the induction and progression of COPD. A hallmark of COPD is a substantially enhanced inflammatory/immune response in the airways and lung, and COPD can be described as a chronic pulmonary disease characterized by progressive airflow limitation. The natural history of COPD typically begins with inflammatory changes in the larger airways (chronic bronchitis). Additional well-recognized features of COPD include remodeling and narrowing of the small airways and parenchymal tissue destruction with airspace enlargement (emphysema). Current treatments do not effectively inhibit chronic inflammation or reverse the pathology of COPD nor do they successfully target the factors that initiate and drive the long-term progression of the disease. Development of novel therapies requires animal models that adequately reflect pathophysiology of this disease. Animal models utilizing cigarette smoke exposure display the characteristic features of human COPD including the accumulation of macrophages, influx of neutrophils and T lymphocytes, increased release of pro-inflammatory mediators (cytokines, chemokines, proteases, and reactive oxygen species), small airway fibrosis/remodeling, mucus hypersecretion, lung dysfunction and the development of emphysema. Indeed exposure of mice to SHS remains the best animal system for defining, testing, and evaluating novel drug targets for COPD (P. Barnes, COPD 1:59-70, 2004; R L Birru et al. *Front Physiol.* 3:348, 2012; M. Podowski et al. *J. Clin. Invest.* 122:229-40, 2012; K. Pappas et al., *Cytokine.* 64:613-25, 2013; R. Vlahos et al., *Clin. Sci.* 126:253-65, 2014). After 20 weeks of smoke exposure, wild type (WT) mice display chronic inflammation, mucus hypersecretion, airway remodeling, emphysema, and reduced lung function which are characteristic features of COPD (E L Beckett et al., *J. Allergy Clin. Immunol.* 131:752-62, 2013). Vascular abnormalities are well known COPD comorbidities and include endothelial dysfunction, arterial stiffness and atherogenesis. Smokers suffer from both decline in lung function and cardiovascular problems. Recent studies demonstrated that vascular inflammation, endothelial dysfunction and oxidative modification of lipids may contribute to pathogenesis. Therefore, it is not surprising that abnormal lung morphology and substantial decrease in function are found in apolipoprotein E-deficient (ApoE$^{-/-}$ mice which are susceptible to cardiovascular issues and atherosclerosis. Exposure of such mice to cigarette smoke causes premature emphysema, abnormal lung inflammation, and airspace enlargement with altered mechanical properties in the lungs (G. Arunachalam et al., *J. Inflamm.* 7:34, 2010).

Zafra, M P et al. *PLoS One* 9(3): e91996, 2014, disclosed the silencing of a "suppressor of cytokine signaling" (SOCS3) in a mouse model of chronic asthma using siRNA delivered intranasally. Improvement in the eosinophil count and the normalization of hyperresponsiveness to methacholine were observed as were an improvement in mucus secretion and a reduction in lung collagen, said to be prominent features of airway remodeling. The results were said to imply involvement of the JAK/STAT and RhoA/Rho-kinase signaling pathways. The reference did not relate to targeted delivery to neutrophils, targeting of the Btk gene, nor treatment of acute lung injury.

Perl, M. et al. (*Mol Med.* 14:465-75. 2008) is a review discussing pathogenesis of ALI and describing use of siRNA in vivo to inhibit ALI. This document elucidates mechanisms of ALI pathogenesis focusing on two main theories: that neutrophils can play a central role in driving ALI and that lung epithelial cell apoptosis is an important pathogenic factor. The authors discuss a double-hit mouse model of indirect ALI induced by hemorrhagic shock (HEM) and subsequent polymicrobial sepsis. A strategy of using siRNA in mouse lungs in vivo is described (for understanding ALI pathology). Results from the HEM-induced septic ALI model implied that the tissue environment (infectious versus inflammatory) encountered by neutrophils is important in determining whether or not they mediate organ damage. Use of silencing RNA is said to represent a potentially powerful experimental approach to allow better understanding of the pathology of ALI and a therapeutic approach to treatment. The history of siRNA, its discovery, development, the mechanisms involved, as well as its successful initial uses in mammals in vivo are described in cited references (Kumar L D et al., *Adv. Drug Deliv. Rev.* 59:87-100, 2007; Aigner A., *Curr. Opin. Mol. Ther.* 9:345-52, 2007; de Fougerolles, A, et al., *Nat. Rev. Drug Discov.* 6:443-53, 2007; Martin S E et al., *Annu. Rev. Genomics Hum. Genet.* 8:81-108, 2007). The lung is said to be a good candidate for application in vivo, as it can be accessed straightforwardly by intranasal (i.n.) or intratracheal (i.t.) routes. Although nucleic acid transfer efficiency is known to be diminished substantially by the phospholipids and proteins of the airway surface liquid, unlike systemic delivery, the delivery of naked siRNA into lungs was efficient, potentially obviating a need for complex and costly approaches using vector systems or chemical siRNA modifications. The feasibility of a surfactant-based or naked siRNA approach in the mouse lung targeting glyceraldehyde-3-phosphate dehydrogenase (GAPDH) or heme oxygenase-1 during ischemia reperfusion, respectively, was noted. The document states that Phase I/II trials for Respiratory Syncytial Virus infection have been conducted and are on their way to evaluate safety, tolerability, and antiviral activity of siRNA treatment in human lungs. The authors described their initial attempts to extend their observation that blockade of MIP-2 or keratinocyte-derived chemokine (KC) with conventional antibodies effected the development of ALI (Lomas J L et al., *Shock.* 19:358-65, 2003) by silencing these chemokines locally in the lung (Lomas-Neira J L et al., *J. Leukoc. Biol.* 77:846-53, 2005). They later studied antiapoptotic siRNA against Fas and caspase-8 assessing their capacity to protect the lung from the detrimental effects of HEM-induced septic ALI (Perl M et al. *Am. J. Pathol.* 167:1545-59, 2005). Using mice over-expressing GFP and receiving a single i.t. instillation of GFP-silencing RNA, they found that green fluorescence in the lungs (18 h post-instillation) was reduced (compared with vehicle-treated GFP mice0, while no decrease in fluorescence was seen in other organs (Perl et al., supra; Lomas-Neira et al., supra). The use of siRNA at these concentrations did not induce an interferon response (via activation of various TLR pathways nor via proinflammatory processes). However, the induction of STAT-1 by this treatment could not be ruled out. The authors' group followed the intrapulmonary deposition of Cy-5 fluorochrome labeled siRNA uptake by confocal immunofluorescence microscopy and found that labeled siRNA co-localized only with lung epithelial cells ("EC") at 18 at 24 h post instillation, but not with alveolar macrophages ("AM"). The feasibility of gene silencing in macrophages using siRNA has been described in vitro, however, silencing of typically macrophage-derived molecules such as TNF-α and IL-6 during indirect murine lung injury remained unsuccessful. Experiments were designed to modulate PMN immigration based on the "neutrophil hypothesis" using in vivo siRNA constructs against murine chemokines KC and MIP-2 during the development of indirect septic ALI. Suitable siRNA constructs were instilled into lungs 2 h following HEM (and prior to induction of sepsis by cecal ligation and puncture), and ALI was assessed 24 h later. Silencing of MIP-2 reduced tissue and plasma IL-6 concentrations, tissue MIP-2, and lung PMN influx, interstitial edema, alveolar congestion, and disruption of lung tissue architecture (citing to Lomas-Nara et al., supra). In contrast, KC-siRNA treatment, while reducing plasma KC, tissue KC, and tissue IL-6, did not significantly reduce plasma IL-6 nor lung neutrophil influx nor lung damage. siRNA sequences specific for Fas and caspase-8 were instilled i.t. during septic ALI and diminished gene-specific lung Fas and caspase-8 expression; pulmonary tissue caspase-3 activity was reduced only in response to Fas but not caspase-8 silencing. Silencing of Fas in lung ECs was associated with a reduction in lung inflammation and neutrophil influx. It was not known whether different forms of ALI (e.g., direct versus indirect) are more of a response to a certain pathogenic mechanism. While numerous diverse stimuli can initiate the pathogenesis of this clinical entity, the final steps in ALI/ARDS, such as compromise of the alveolo-capillary bather function, appear to be somewhat common. This document reviewed data supporting the independent roles of activated PMN vs EC death in ALI. Upon early Fas activation, AM and lung ECs can produce chemokines in the lung, attracting activated and potentially harmful PMNs, monocytes, or even T cells to the site of injury and potentiating the degree of injury. This documents did not mention or suggest targeting Btk nor using an anti-neutrophil antibody to deliver any siRNA let alone BTK-specific siRNAs to the lungs.

Bojnik et al., Abstract S521, 18$^{th}$ Cong. European Hematology Assoc, 2013, discloses efficient silencing of BTK in primary chronic lymphocytic leukemia (CLL) cells by RNA interference resulting in a 60-90% reduction in protein levels compared to CLL cells 'nucleofected" with a control siRNA. This resulted in silencing of BTK-accelerated apoptosis. This reference does not disclose conjugating siRNA to any antibody or targeting PMNs in vivo, let alone in the lung or in the treatment ALI.

Peer et al., US Pat. Publ. 2013/0129752 discloses a delivery agent selective for leukocytes or activated leukocytes, comprising a targeting moiety, such as an antibody or functional fragment that selectively binds LFA-1 (integrin Lymphocyte Function-Associated Antigen-1 which is also expressed on neutrophils), a protein carrier moiety covalently linked to the targeting moiety, and a therapeutic agent associated with the carrier moiety—such as a RNA interference molecule (siRNA, dsRNA, stRNA, shRNA, miRNA). Examples of a protein carrier are a basic polypeptide such as protamine or a functional fragment thereof that provide the structure for non-covalent binding to a nucleic acid. This protein carrier serves as a "bridge" between the antibody and the siRNA. Methods for selective delivery to leukocytes/activated leukocytes in vivo, in vitro and ex vivo are disclosed. In the Examples, genetically engineered scFV fragments of two different anti-LFA-1 antibodies were used as the "targeting moiety." This document does not disclose delivering siRNA to neutrophils in the lung using an antibody construct to treat ALI but it does disclose delivery of siRNA to "lungs" in vivo in an indirect and "model-peculiar" way (para's [0372]-[0374]. This cannot be equated to the present invention's delivery of Btk-siRNA to human lungs in vivo. This protein carrier artifice was needed because human LFA-1 does not cross-react with mouse LFA-1 so that the anti-LFA-1 antibody targeting moiety could not bind to mouse LFA-1 in mouse lungs. Therefore, the authors used immunocompromised SCID mice into which they xenografted human leukemia cells stably transfected to express human LFA-1. After these tumors formed small nodules in mouse lungs, i.v. fusion protein complexes comprising anti-LFA-1 Ab fragments-protamine fusions complexed with siRNA were injected and found their way to the transfected human tumor cells expressing human LFA-1 in the lung and delivered the siRNA. The authors considered this to be in vivo proof of principle for effective systemic siRNA delivery by these fusion proteins to LFA-1-expressing cells. The disclosed compositions and methods required "3-component moieties" that in addition to the targeted therapeutic (siRNA) and the targeting moiety (e.g., antibody) required a carrier protein covalently bonded to the targeting moiety. A basic polypeptide exemplified as a protamine or protamine fragment is contemplated as the carrier protein and acts by binding non-covalently to the siRNA to carry it.

Simon, US2005/0255120 describes a composition comprising: a cell surface receptor specific ligand bonded to a dsDNA that encodes a promoter region. This construct is functionally linked to express siRNA or short hairpin RNA (shRNA) that suppresses production of a cellular protein. Simon, US2005/0260214) discloses a composition comprising: a cell surface receptor-specific immunoglobulin (Ig) (antibody) or Ig component ligand bonded to a dsRNA encoding a siRNA or to a shRNA sequence that suppresses production of a cellular protein. The antibody is specific for a cell surface antigen. These references do not relate to Btk-specific siRNA's or to anti-neutrophil antibodies nor do they disclose or suggest targeting the lung, targeting neutrophils or targeting Btk. (The word "lung" does not appear in these publications.)

Ford et al., WO2009/102782 discloses a conjugate for delivery of a nucleic acid, including siRNA, to cells which comprises a carrier that binds non-covalently to the nucleic acid that is covalently coupled to a ligand that binds to a cell surface, such as an antibody or antigen-binding fragment thereof. This publication describes a method of treating a subject with this conjugate by administering a pharmaceutically acceptable composition comprising a therapeutically effective amount of the conjugate that binds to the nucleic acid non-covalently and at least partially inhibits one or more symptoms of a disease. The document refers to the "promise" of direct delivery of RNAi agents in vivo with affinity reagents, especially antibodies, for treating diseases and disorders characterized by "the under-expression or over-expression of a gene or group of genes, including genes with mutations." This is said to include metabolic diseases and disorders (e.g., where the liver is a target), infectious diseases caused by viruses, bacteria and fungi, and cancer (particularly myeloid leukemia). Pharmaceutical compositions for pulmonary (aerosol inhalation) or nasal administration, are disclosed. Pulmonary administration is said to include inhalation of aerosolized or nebulized liquid or solid particles of the pharmaceutically active component dispersed in and surrounded by a gas. The only example of in vivo use is injection of a composition that mixes GAPDH-specific siRNA anti-Her-2 mAb conjugated with protamine (which provides the nucleic acid binding capacity) into mice carrying a xenografted human tumor and demonstrating reduction of GAPDH expression in the tumors a few days later. The conjugates described in this document are not conjugates of an antibody with a siRNA (or other nucleic acid) bur rather a 3 part complexes of a conjugate of antibody with a nucleic acid binding molecule (such as a protamine) and a nucleic acid.

Cha et al., WO2012/006083 discloses molecular conjugates of ligands covalently linked, directly or via a linker, to a siRNA moiety and a method for delivering molecular conjugates to a cell. The method comprises (a) contacting a cell or cells with a molecular conjugate comprising a ligand having affinity for a cell surface receptor and an siRNA moiety linked to the ligand; and (b) maintaining the cell, or a population of such cells, under conditions whereby the ligand specifically binds to a cell surface receptor, whereupon the conjugate enters the cells by endocytosis, and delivers the siRNA moiety to the cytoplasm. The document generically discloses non-specific siRNA delivery but notes that cell-type-specific delivery is the most challenging step blocking the progress of RNAi therapy. It notes that targeting siRNA to specific cell or tissue types requires that the specificity be built into the delivery agents or the expressed siRNAs, for example by antibody targeting (citing Yu et al. *AAPS J.* 11:195-203, 2009, see below). The disclosure focuses on ligands for surface receptors, primarily muscarinic receptors and the targeting of exocrine glandular cells of salivary gland, lacrimal gland, tracheobronchial gland, digestive gland, or sweat gland. Therapeutic focus is on Sjogren's Syndrome and the silencing of inflammatory caspases. The examples are limited to targeting conjugates of carbachol (a muscarinic ligand) with siRNA specific for caspase-3 to human salivary gland cells. While intrapulmonary and intranasal administration appears in a long list of routes of administration, this application does not specifically disclose any lung disease nor its treatment by administering such a conjugate to lung tissue.

Yu, B. et al., *AAPS J.* 11:195-203, 2009, discloses various conjugates of oligonucleotides such as siRNA with ligands for cell-specific or site-specific delivery of the oligonucleotides. The following examples of target tissues and delivery strategies are disclosed using antibody targeting moieties:

| Target tissues/cells | Delivery Strategies | Ref |
| --- | --- | --- |
| Activated leukocytes/K562 leukemia | Antibody-protamine-siRNAs complexes | (a) |
| Leukocytes | β7 integrin Ab-HA coated liposomes | (b) |
| Mammary carcinoma | anti-HER2 antibody (61), | (c) |
| Human B-lymphoma cell lines | CD19-targeted liposomes | (d) |
| Neuroblastoma or melanoma | GD2 ganglioside-targeted immunoliposomes | (e) |

(a) E. Song, et al. *Nat. Biotechnol.* 23:709-17, 2005;
(b) D. Peer, et al. *Proc. Natl. Acad. Sci. U.S.A.* 104:4095-4100, 2007);
(c) D. B. Kirpotin et al., *Cancer Res.* 66:6732-40, 2006.;
(d) D. D. Stuart et al., *Cancer Gene Ther.* 7:466-75, 2000;
(e) G. Pagnan et al., *J. Natl. Cancer Inst.* 92:253-61 (2000)

This reference does not describe or suggest an oligonucleotide conjugated to neutrophil-specific antibody nor selective delivery by any antibody of an oligonucleotide to any cell in the lungs.

SUMMARY OF THE INVENTION

Previous observations by the present inventor's laboratory indicate that Bruton's tyrosine kinase (Btk) plays an important role in the pathophysiology of local inflammation in ALI/ARDS. Cross talk occurs between FcγRIIa and to TLR4 in alveolar neutrophils from patients with ALI/ARDS, and Btk mediates the molecular cooperation between these two receptors. To study the function of Btk in vivo the present inventor developed a unique two hit model of acute lung injury (ALI) induced by bacterial lipopolysaccharide (LPS) and immune complexes (IC). Further, F(ab')$_2$ fragments of anti-neutrophil monoclonal antibodies (mAbs) in the form of Ly6G1A8 (specific for mouse neutrophils) were conjugated to siRNA that is specific/selective for Btk (murine) to silence Btk specifically in alveolar neutrophils. The present inventor was the first to perform non-invasive transfections of neutrophils, both in vitro and in vivo. The present findings indicate that silencing Btk in alveolar neutrophils has a dramatic protective effect in mice with LPS/IC induced ALI, and that Btk regulates neutrophil survival and clearance of apoptotic neutrophils. Similar results occur in the case of ALI induced by pulmonary infection with influenza A ("Flu") virus and in a model for chronic obstructive pulmonary disease (COPD) induced by chronic exposure to second hand smoke (SHS).

The present invention is directed to a method for inhibiting Bruton's tyrosine kinase (Btk) activity in the lungs of a subject, comprising providing to the lungs of the subject Btk an effective amount of a Btk inhibitor that is (a) a siRNA molecule that binds specifically to a complementary target sequence of Btk RNA, or (b) a small organic molecule inhibitor of Btk, or (c) a combination of (a) and (b).

The present invention is also directed to a method for treating symptoms of a lung disease or disorder that result from activation or activity of Btk in the lungs of a subject, comprising delivering to the lungs of said subject in need of such treatment an effective amount of a Btk inhibitor that is (a) a siRNA molecule that binds specifically to a complementary target sequence of Btk RNA, or (b) a small organic molecule inhibitor of Btk, or (c) a combination of (a) and (b).

In the above method the lung disease or disorder is selected from the group consisting of ALI, ARDS, severe lung inflammation, influenza, emphysema, COPD, asthma, bronchitis, pneumonia, pulmonary edema, lung cancer, bacterial lung infections, viral lung infections, preferably, cystic fibrosis and the like.

In the above method the Btk inhibitor is preferably administered intranasally. Preferably, the siRNA is bound or conjugated to a neutrophil-selective targeting agent, preferably a neutrophil-specific antibody or antigen binding fragment or derivative thereof such that the siRNA is targeted to alveolar neutrophils. Preferred anti-neutrophil antibody (or fragment or derivative) is specific for a neutrophil surface antigen preferably CD66b/CD67 or CD177, or to an epitope thereof.

In the above method, the preferred small molecules Btk inhibitor is selected from the group consisting of Ibrutinib/PCL-32765; AVL-101; AVL-291; AVL-292; Dasatinib; LFM-A13; and GDC-08fe34, more preferably Ibrutinib/PCL-32765.

In the above method, the Btk target sequence which is targeted by the siRNA targets is preferably SEQ ID NO:5, SEQ ID NO:6, SEQ ID NO:7, SEQ ID NO:8, SEQ ID NO:9, SEQ ID NO:10 or SEQ ID NO:11. The siRNA is preferably a dsRNA molecule and is preferably between about 19 and about 29 nucleotides in length (or 2 nt's longer if a 2 nt overhang is included). Preferred the antisense sequence of the siRNA is SEQ ID NO:13, SEQ ID NO:15, SEQ ID NO:17, SEQ ID NO:19, SEQ ID NO:21, SEQ ID NO:23 or SEQ ID NO:25.

In a another embodiment, the invention is directed to the use of an siRNA molecule that binds specifically to a complementary target sequence of Btk RNA or to a small organic molecule inhibitor of Btk, for the preparation of a medicament for inhibiting Btk activity in the lungs of a subject. Also provided is the use of a siRNA molecule that binds specifically to a complementary target sequence of Btk RNA or a small organic molecule inhibitor of Btk for the preparation of a medicament for treatment of symptoms of a lung disease or disorder that result from activation or activity of Btk in the lungs of a subject. The medicament is preferably for use in ALI, ARDS, severe lung inflammation, influenza, emphysema, COPD, asthma, bronchitis, pneumonia, pulmonary edema, lung cancer, bacterial lung infections, viral lung infections, preferably, cystic fibrosis and the like. In a preferred, use, the medicament is administered intranasally.

In the above use, the siRNA is preferably bound or conjugated to a neutrophil-selective targeting agent, such that the medicament is targeted to alveolar neutrophils. A preferred targeting agent is a neutrophil-specific antibody or antigen binding fragment or derivative thereof, more preferably an antibody, fragment or derivative that is specific for a neutrophil surface antigen selected from the group consisting of CD66b/CD67 and CD177 (or an epitope thereof).

In the above use, the small molecule Btk inhibitor is preferably Ibrutinib/PCL-32765; AVL-101; AVL-291; AVL-292; Dasatinib; LFM-A13; or GDC-0834, more preferably Ibrutinib/PCL-32765.

In the above use, the Btk target sequence which is targeted by the siRNA targets is preferably SEQ ID NO:5, SEQ ID NO:6, SEQ ID NO:7, SEQ ID NO:8, SEQ ID NO:9, SEQ ID NO:10 or SEQ ID NO:11. The siRNA is preferably a dsRNA molecule and, preferably, the siRNA is between about 19 and about 31 nucleotide in length. A preferred sequence of the antisense sequence of the siRNA is SEQ ID NO:13, SEQ ID NO:15, SEQ ID NO:17, SEQ ID NO:19, SEQ ID NO:21, SEQ ID NO:23 or SEQ ID NO:25.

BRIEF DESCRIPTION OF THE DRAWINGS

FIG. 1A: Hematoxylin and eosin ("H&E") staining of lung sections. Mice were injected intraperitoneally with LPS or Saline. Eight hours later the animals received anti-KC:KC immune complexes (ALI group) or saline (Saline group). ALI/Neutrophils siRNA FcγRIII mice were injected with vinblastine to deplete neutrophils and then neutrophils were replenished with cells deficient in FcγRIII receptors (ALI/Neutrophils siRNA FcγRIII group).

FIG. 1B Expression of FcγRIII receptors (bright fluorescence) in lung neutrophils of mice treated with LPS and anti-KC:KC immune complexes (ALI group) and ALI/Neutrophils siRNA FcγRIII mice. Lung neutrophils were visualized with anti-neutrophil antibody Ly6G1A8 (Gr-1; bright cells in left panels). 3-6 animals per group; typical findings are presented.

FIG. 1C: H&E staining of lung sections of mice which were immunized with KC to develop anti-KC autoantibodies and then either received Saline (Saline) or KC (Anti-KC:KC IC ALI), or were treated with vinblastine (Anti-KC:KC IC ALI/vinblastine), or were treated with vinblastine and received neutrophils transfected with siRNA specific for FcγRIII (Anti-KC:KC IC ALI/Neutrophils siRNA FcγRIII).

FIG. 1D: Expression of FcγRIII receptors (bright fluorescence) in lung neutrophils of mice (Anti-KC:KC IC ALI) and (anti-KC:KC IC ALI/Neutrophils siRNA FcγRIII mice). Lung neutrophils were visualized with anti-neutrophil antibody Ly6G1A8 (Gr-1: bright cells in left panels). 3 animals per group; typical findings are presented.

FIG. 2D1 to 2D-3: Analysis of levels of pBtk in mouse alveolar neutrophils purified from either mice treated with LPS and immune complexes (LPS/IC) or animals treated with LPS and Saline (LPS/Sal). The vertical bar chart in FIG. 2D-3 depicts the fold increase in the level of pBtk in lung neutrophils from LPS/IC in comparison to LPS/Sal mice. Alveolar neutrophils from 3 animals per group (160-250 cells were scanned); typical findings are presented.

FIG. 3A: H&E staining of lung sections of mice treated with LPS, siRNA for Btk, and anti-KC:KC immune complexes (ALI/siRNA Btk group). 3-6 animals per group; typical findings are presented.

FIG. 3B: Expression of Btk (bright fluorescence in cytoplasm/periphery) in lung neutrophils from mice treated with Saline (Saline), LPS and anti-KC:KC ICs (ALI group), and mice that received Btk siRNA prior to the administration of ICs (ALI/siRNA Btk group). Hoechst 33442 was used to visualize DNA (grey in cells). Alveolar neutrophils from 3 mice per group were analyzed; typical findings are presented.

FIG. 3C: Expression of Btk (bright fluorescence in panels labeled Btk) in lung neutrophils (Gr-1; duller fluorescence in panels labeled Gr-1) from mice groups: ALI and ALI/siRNA Btk. Cells were photographed under 20× magnification and at least 300 neutrophils per group were evaluated. 3 animals per group; typical findings are presented. Samples were obtained 14 hours after anti-KC:KC IC administration.

FIG. 4A: H&E staining of lung sections. Mice were treated with Saline (Saline group), with LPS and anti-KC:KC immune complexes (ALI group), with LPS and Btk siRNA conjugated to F(ab')$_2$ fragments of anti-neutrophil antibody Ly6G1A8 (ALI/siRNA Btk group), with LPS and control siRNA conjugated to F(ab')$_2$ fragments (ALI/cont siRNA group), with F(ab')$_2$ fragments of Ly6G1A8 alone (ALI/F(ab')$_2$ only group). 4-5 animals per group; typical findings are presented. Samples were obtained 14 hours after anti-KC:KC IC administration.

FIG. 4B. Expression of Btk (bright fluorescence in panels labeled Btk) in lung neutrophils from mice treated with LPS and anti-KC:KC immune complexes (ALI group), with LPS and Btk siRNA conjugated to F(ab')$_2$ fragments of anti-neutrophil antibody Ly6G1A8 and immune complexes (ALI/siRNA Btk group), with LPS and control siRNA conjugated to F(ab')$_2$ fragments of Ly6G1A8 and ICs (ALI/Cont siRNA group). Neutrophils were visualized using Ly6G1A8 (Gr-1; duller fluorescence in panels labeled Gr-1). The effectiveness of Btk silencing in alveolar neutrophils was 92%. Samples were obtained 2 hours after anti-KC:KC IC administration.

FIG. 4C: Expression of Btk (bright fluorescence in panels labeled Btk) in lung neutrophils (Gr-1; duller fluorescence in panels labeled Gr-1) from mice groups: ALI, ALI/siRNA Btk and ALI/Cont siRNA. Cells were photographed at 20× magnification and at least 300 neutrophils per group were evaluated. Samples were obtained 2 hours after anti-KC:KC IC administration.

FIG. 4D: Expression of pBtk (bright fluorescence) in lung neutrophils from mice with ALI treated with either control siRNA conjugated to F(ab')$_2$ fragments of Ly6G1A8 (ALI/Cont siRNA group) or with Btk siRNA conjugated to F(ab')$_2$ fragments of Ly6G1A8 (ALI/siRNA Btk group). Samples were obtained 2 hours after anti-KC:KC IC administration.

FIG. 4E: Specificity of treatment with Btk siRNA. Expression of Btk (bright fluorescence in panels labeled BTK) in lung tissue neutrophils from mice with ALI treated with either control siRNA conjugated to F(ab')$_2$ fragments of Ly6G1A8 (ALI/Cont siRNA group) or with Btk siRNA conjugated to F(ab')$_2$ fragments of Ly6G1A8 (ALI/siRNA Btk group). Lung neutrophils were visualized with anti-neutrophil antibody Ly6G1A8 (Gr-1; bright cells in panels labeled GR-1). Arrows point to other cell types. Samples were obtained 14 hours after anti-KC:KC IC administration FIGS. 5A-5C.

FIG. 6A: Expression of matrix metalloproteinase MMP-9 (bright fluorescence) in lung neutrophils from mice treated with saline (Saline), LPS and anti-KC:KC ICs (ALI), LPS and Btk siRNA and ICs (ALI/siRNA Btk). Neutrophils were visualized using anti-neutrophil antibody Ly6G1A8 (Gr-1; neutrophils are visible as brighter objects). 3 animals per group; typical results are presented. Samples were obtained 14 hours after anti-KC:KC IC administration FIG. 6B. Fluorescence intensity of MMP-9 shown in both a bar graph (fold-increase) and micrograph insets (showing bright fluorescence) in neutrophils from mice treated with Saline (Saline), with LPS and ICs (ALI), with LPS and control siRNA conjugated to Ly6G1A8 F(ab')$_2$ fragments and ICs (ALI/Cont siRNA), with LPS and Btk siRNA conjugated to Ly6G1A8 F(ab')$_2$ fragments and ICs (ALI/siRNA Btk), and with LPS and MMP-9 siRNA conjugated to Ly6G1A8 F(ab')$_2$ fragments and ICs (ALI/siRNA MMP-9). The effectiveness of MMP-9 silencing in alveolar neutrophils was 91%. 3 animals per group; typical findings are presented. Samples were obtained 2 hours after anti-KC:KC IC administration.

FIG. 6C: H&E staining of lung sections of mice treated with Saline (Saline) and mice treated with LPS and MMP-9 siRNA conjugated to Ly6G1A8 F(ab')$_2$ fragments and ICs (ALI/siRNA MMP-9). 4-5 animals per group; typical findings are presented. Samples were obtained 14 hours after anti-KC:KC IC administration FIG. 6D: Detection of thrombomodulin (TM) in bronchoalveolar fluid of mice treated with Saline (Saline), with LPS/IC induced ALI (ALI), treated with LPS and Btk siRNA conjugated to Ly6G1A8 F(ab')$_2$ fragments and ICs (ALI/siRNA Btk), treated with LPS and MMP-siRNA conjugated to Ly6G1A8 F(ab')$_2$ fragments and ICs (ALI/siRNA MMP-9), and treated with LPS and control siRNA conjugated to Ly6G1A8 F(ab')$_2$ fragments and ICs (ALI/cont siRNA). 3 animals per group; typical findings are presented. Samples were obtained 2 hours after anti-KC:KC IC administration. The bar graph includes data from 3 experiments (see Examples).

FIG. 7D-1-3 shows number of lymphocytes (FIG. 7D-1), neutrophils (FIG. 7D-2), and total leukocytes (FIG. 7D-3) in circulation of mice treated with saline (Saline), with LPS and anti-KC:KC ICs (ALI), with LPS and Ly6G1A8 F(ab')$_2$ fragments and ICs (ALI/F(ab')$_2$), with LPS and MMP-9 siRNA conjugated to Ly6G1A8 F(ab')$_2$ fragments and ICs (ALI/siRNA MMP-9). 5 animals per group; typical findings are presented.

FIG. 10A: H&E staining of lung sections of control mice (Control), mice with Flu virus A induced ALI (Influenza), mice with ALI treated with Btk siRNA conjugated to F(ab')$_2$ fragments of anti-neutrophil mAb Ly6G1A8 (Btk siRNA) and mice with ALI that received control siRNA (Control siRNA). 3 to 5 animals per group in FIGS. 10B and 10C; typical findings are presented.

FIG. 10B: Expression of Btk in lung neutrophils (PMN) of control mice (Control), mice with Flu virus A induced ALI (Influenza), mice with ALI treated with Btk-siRNA (Btk siRNA) and mice with ALI that received control siRNA (Control siRNA).

FIG. 10C: Expression of Btk (bright fluorescence) in lung neutrophils (PMN) of mice with influenza virus A induced ALI (Influenza). 3 animals per group in FIGS. 10B and 10C; typical findings are presented.

DESCRIPTION OF THE PREFERRED EMBODIMENTS

Figure 8A:
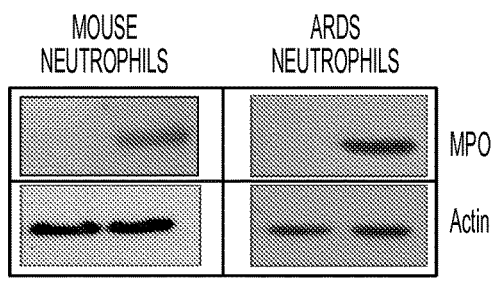
FIGS. 8A-8B. Myeloperoxidase (MPO) (FIG. 8A) and superoxide release (pp40phox) (FIG. 8B) from mouse bone marrow neutrophils stimulated with mouse anti-KC:KC ICs and human neutrophils stimulated with clinical anti-IL-8:IL-8 ICs (ICEF). ICEF were purified from pulmonary edema fluids from patients with ALI/ARDS and human neutrophils used for these experiments from blood of these patients.
Figure 8B:
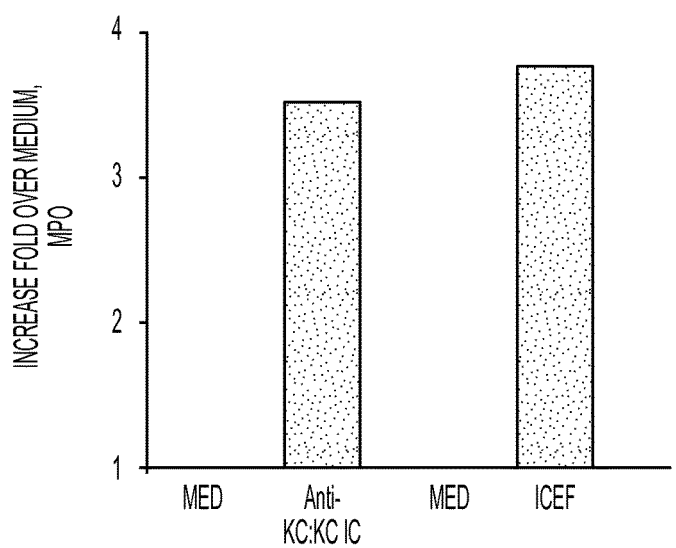
Figure 8C:
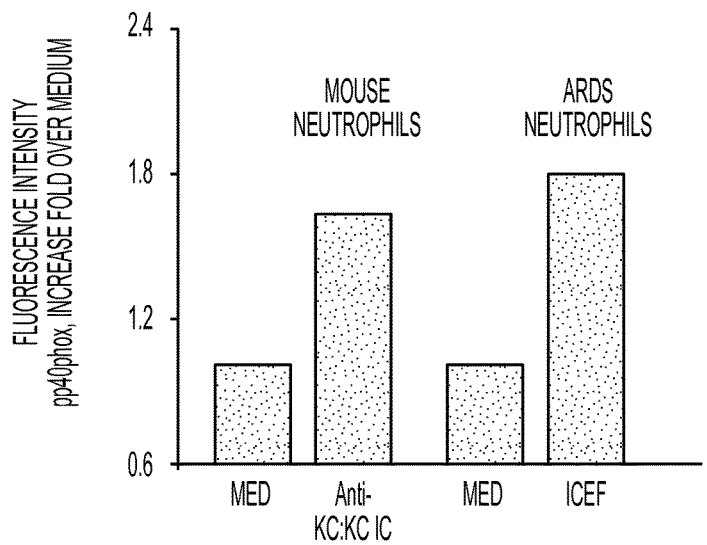

The present invention is a result of the discovery that ALI is treated by inhibition of Btk. The present inventor and colleague had previously demonstrated that Btk associated pathways may play an important role in the pathophysiology of local inflammation in ALI/ARDS (25). Moreover, their findings indicate that Btk mediates the crosstalk between FcγRIIa and TLR4 in alveolar neutrophils from patients with ALI/ARDS (25). To study the role of Btk in the cooperation between TLR4 and FcγRIII receptors (mouse equivalent of human FcγRIIa, 5, 15, 41) in vivo, unique two hit model of ALI ([LPS]/anti-KC:KC immune complex [IC]-induced ALI) was developed as a clinically relevant model of ALI. It is important to note that the inventor established that anti-KC:KC complexes are the mouse equivalent of clinical immune complexes purified from the pulmonary edema fluids of patients with ALI/ARDS, i.e., human anti-IL-8:IL-8 immune complexes. Functional assays (myeloperoxidase release [MPO; FIG. 8A] and superoxide release; pp40phox, 45; FIG. 8B) confirmed that mouse bone marrow neutrophils respond to mouse anti-KC:KC ICs in a similar manner as human neutrophils to clinical anti-IL-8:IL-8 ICs (ICEF) (13, 26, 27). Further, ICEF were purified from pulmonary edema fluids from patients with ALI/ARDS and human neutrophils used for these experiments from blood of these patients.

The present inventors and colleagues previously demonstrated that Btk associated pathways may play an important role in the pathophysiology of local inflammation in ALI/ARDS (25). Their findings indicated that Btk mediates the crosstalk between FcγRIIa and TLR4 in alveolar neutrophils from patients with ALI/ARDS (25). To better understand the role of Btk in the cooperation between TLR4 and FcγRIII receptors (mouse equivalent of human FcγRIIa, 5, 15, 41) in vivo, the present inventors developed a clinically relevant and unique two hit model of ALI ([LPS]/anti-KC:KC immune complex [IC]-induced ALI).

This two hit model was used to confirm the present inventor's conception that Btk dependent signaling pathways control neutrophil activation and survival. The present inventor's laboratory is the first to perform non-invasive transfections of neutrophils using specific siRNAs conjugated to F(ab')$_2$ fragments of anti-neutrophil antibody (Ly-6G1A8) that is specific for murine neutrophils. As detailed in the examples, conjugated siRNA were administered via intranasal route to animals pre-treated with LPS prior to the administration of ICs to counteract the pathogenic effects of these complexes. This is because their previous studies demonstrated that ICs such as anti-IL-8:IL-8 ICs may contribute to severity of lung inflammation in patients with ALI/ARDS and may affect the outcome of ALI/ARDS (3, 14, 26-30). Finally, since high concentrations of Ly-6G 1A8 are routinely utilized to deplete neutrophils by triggering their apoptosis, F(ab')$_2$ fragments were purified and employed at a low concentration that does not affect neutrophil survival.

Blocking Btk using the present methodology is advantageous to using Btk deficient (Xid) mice to study the role of neutrophils in ALI. Neutrophils from Btk deficient mice may be less readily recruited to the site of inflammation, most likely because of the impaired slow rolling mediated by E-selectin (39, 56). However, Fiedler et al. (10) did not observe an obvious defect in neutrophil recruitment in a mouse model of ear edema, using Xid mice treated with thioglycollate. Importantly, in the present two hit model of ALI, the numbers of neutrophils were similar in lungs of LPS/IC induced ALI and animals treated with siRNA specific for Btk (p=0.02), when evaluated at the peak of neutrophil influx which was 2 h after IC administration to LPS pre-treated animals. Of course, at a later time point (14 h) neutrophils underwent apoptosis and their numbers were affected by this process.

In summary, the present therapy specifically targets alveolar neutrophils. This is a unique approach that cannot be achieved using knockout (KO) or transgenic mice. Neutrophil-specific KO mice have not yet been developed, but even if they were available, they would not allow for studying the effects of Btk deficiency during the course of lung inflammation. Xid neutrophils may have other defects in signaling repertoire (10), which further reinforces the superiority of the present approach.

Figure 5A:
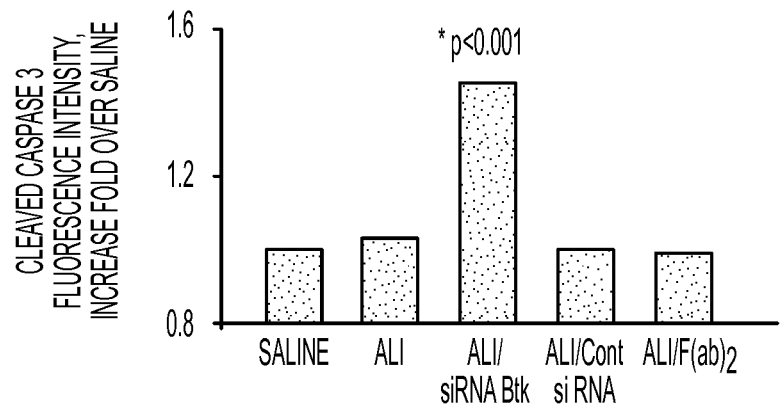
FIG. 5A: Fluorescent activity of cleaved Caspase 3 expressed as fold-increase over saline in lung neutrophils of mice treated with saline (Saline), with LPS and anti-KC:KC immune complexes (ALI), with LPS and Btk siRNA conjugated to F(ab')$_2$ fragments and ICs (ALI/siRNA Btk group), with LPS and control siRNA conjugated to F(ab')$_2$ fragments of Ly6G1A8 and ICs (ALI/cont siRNA), and with F(ab')$_2$ fragments of Ly6G1A8 and ICs (ALI/F(ab')$_2$). 4-5 animals per group; typical findings are presented.
Figure 5B:
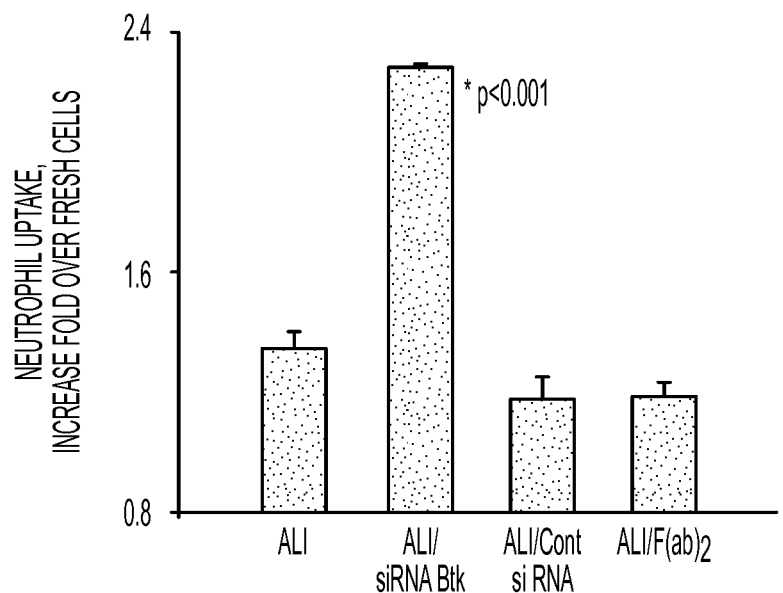
FIG. 5B: Clearance/uptake of purified lung neutrophils (fold-increase over fresh cells) from mice treated with LPS and anti-KC:KC ICs (ALI), with LPS and Btk-siRNA conjugated to F(ab')$_2$ fragments and ICs (ALI/siRNA Btk), with LPS and control siRNA conjugated to Ly6G1A8 F(ab')$_2$ fragments and ICs complexes (ALI/cont siRNA), and with F(ab')$_2$ fragments of Ly6G1A8 only and ICs (ALI/F(ab')$_2$). Neutrophils from 4-5 animals per group were analyzed; typical findings are presented.

Key responses required for the termination of inflammation in the lung are the induction of neutrophil apoptosis and the enhancement of phagocytic clearance of apoptotic neutrophils (9). Both of these pro-resolution events are suppressed during ALI/ARDS leading to excessive accumulation of these cells in the alveolar compartment promoting lung injury (33, 35, 36). The present studies showed that Btk-associated pathways have a detrimental effect on the removal of excessive numbers of neutrophils from lungs. The present two hit model of ALI was employed to address the hypothesis that Btk-dependent pathways expressed in neutrophils modulate neutrophil survival and control phagocytic uptake of these cells. The present results showed that Btk affected survival of neutrophils in lungs (FIG. 5A) and controlled the process of neutrophil uptake by macrophages (FIG. 5B). Therefore, targeted blocking of Btk in alveolar neutrophils protected mice from lung inflammation and injury by promoting apoptosis of neutrophils and by facilitating clearance of apoptotic neutrophils. In agreement with these findings Honda et al. (20) demonstrated that Btk deficient neutrophils purified from blood of patients with X-linked agammaglobulinemia (XLA) were more apoptotic than cells from normal blood.

Figure 5C:
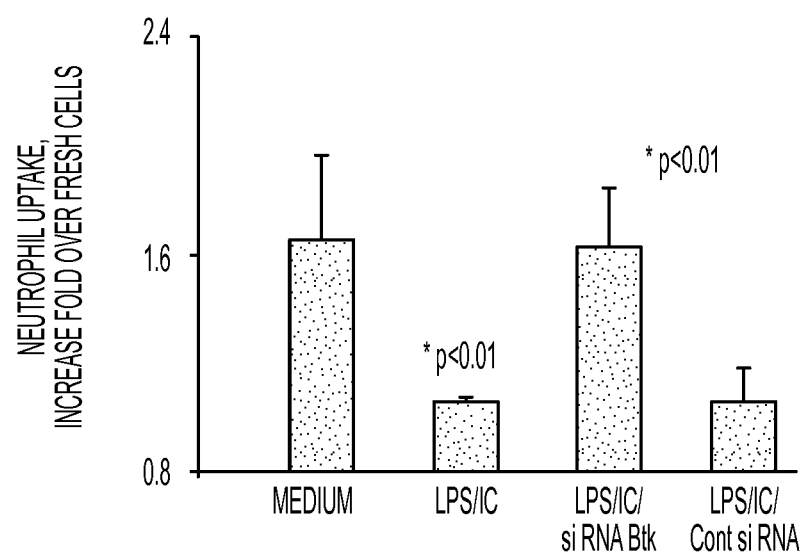
FIG. 5C: Clearance/uptake of bone marrow neutrophils undergoing spontaneous apoptosis (Medium), apoptosis in the presence of LPS and anti-KC:KC ICs (LPS/IC), apoptosis in the presence of LPS, immune complexes, and siRNA for Btk conjugated to Ly6G1A8 F(ab')$_2$ fragments (LPS/IC/siRNA Btk), and apoptosis in the presence of LPS, ICs and control siRNA conjugated to Ly6G1A8 F(ab')$_2$ fragments (LPS/IC/Cont siRNA). Results from 3 experiments were analyzed; typical findings are presented.

Various molecules on neutrophil cell surface undergo specific changes during apoptosis. These include modifications in the composition of carbohydrates and phospholipids, and altered ability to bind serum proteins (8, 23, 46). The present findings indicate that Btk has a regulatory role in the preparation of apoptotic cells for phagocytosis. Thus, Btk is conceived as being critical for identification of apoptotic cells to be cleared from the alveolar compartment (FIG. 5C).

Figure 6A:
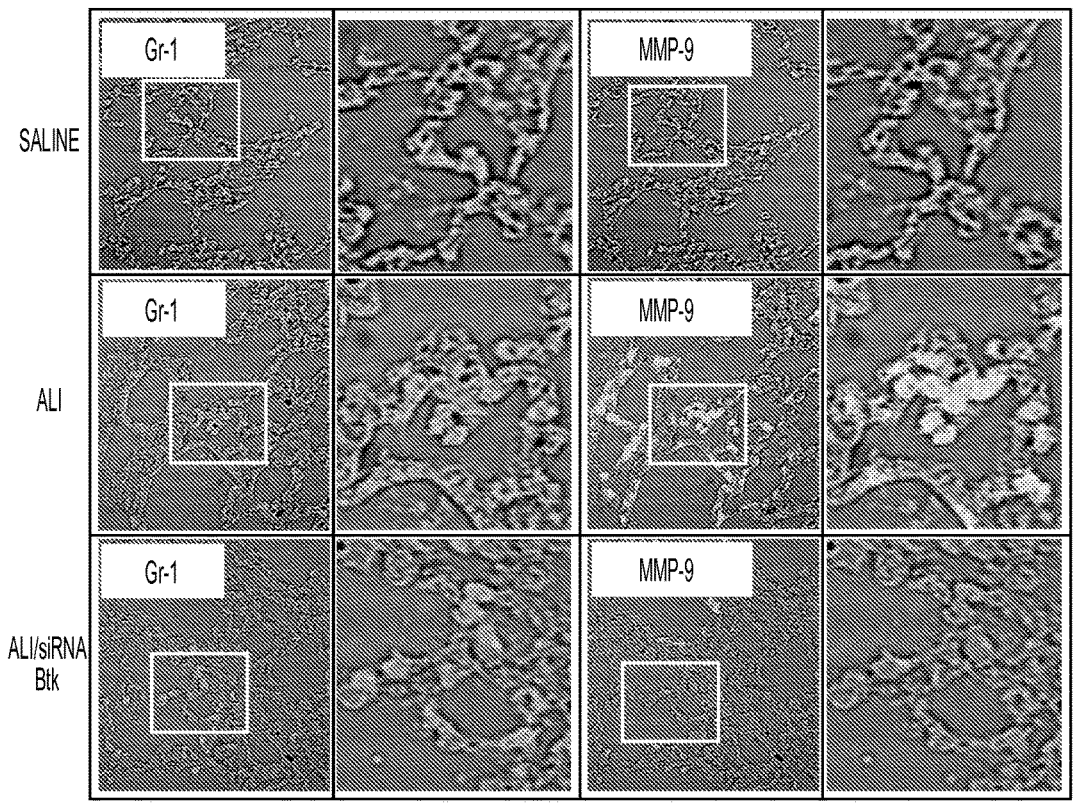
FIG. 6A-6D.
Figure 6B:
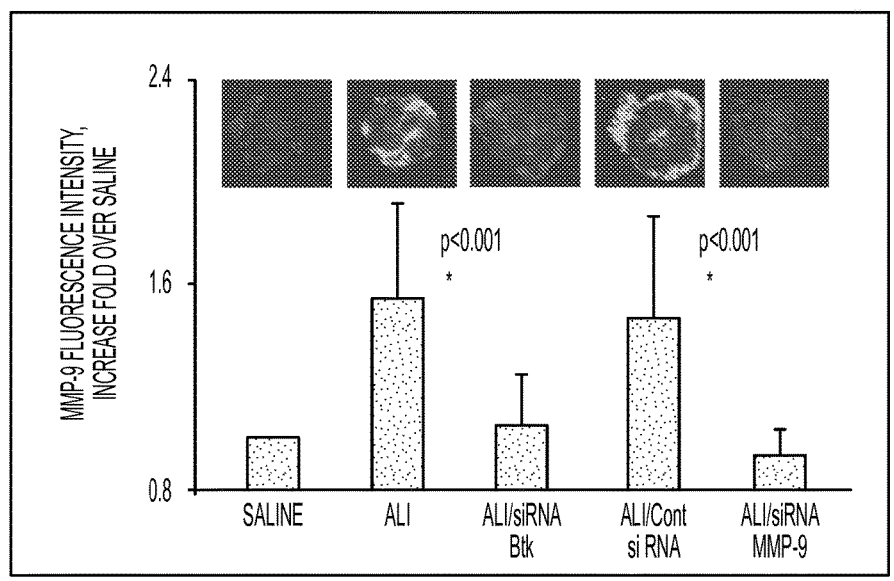
Figure 6C:
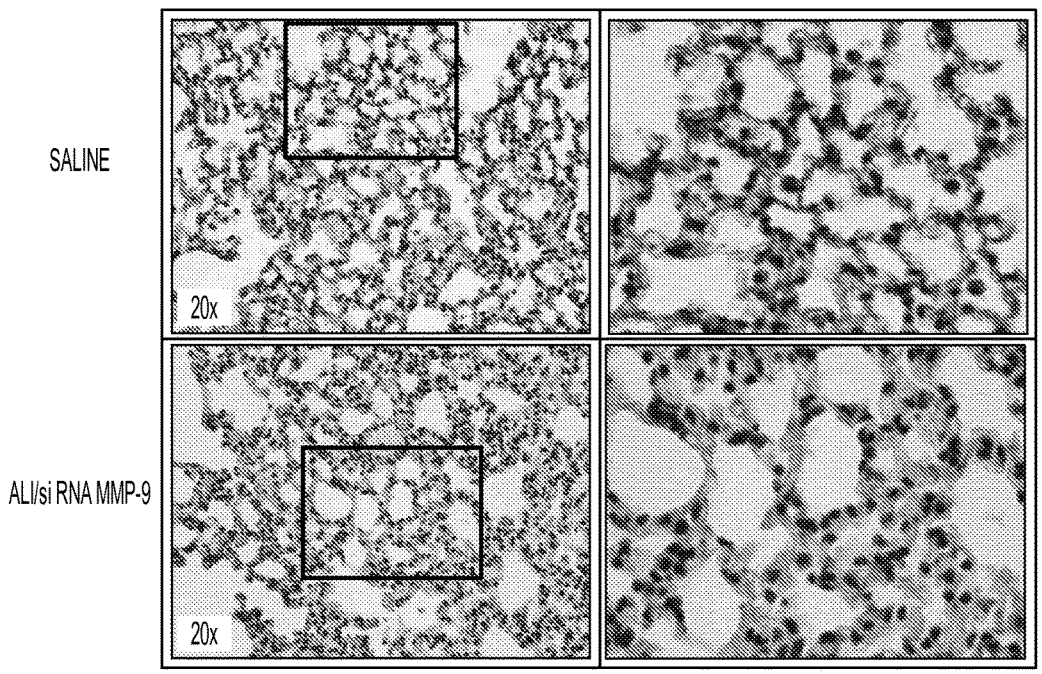
Figure 6D:
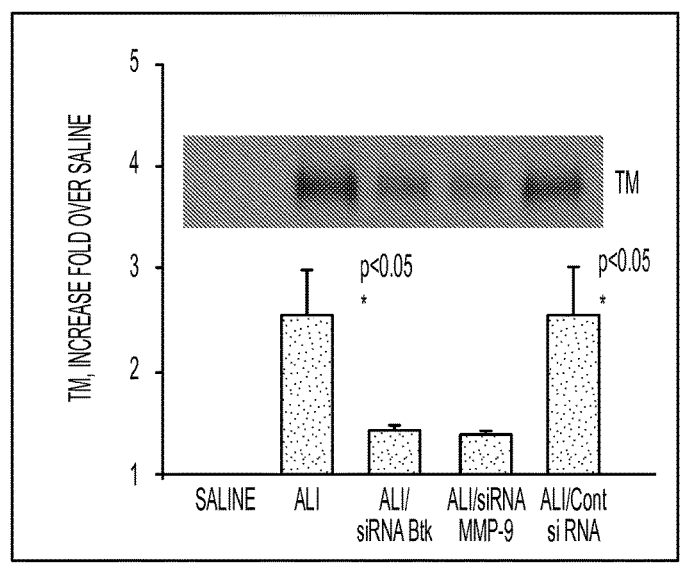

Neutrophils are implicated in ALI because of various pro-inflammatory mediators, including the matrix metalloproteinase (MMP-9), that are released from the granules in the areas of inflammation. Most recent studies have shown that bronchoalveolar lavage (BAL) fluids and plasma from patients with ALI/ARDS contain elevated concentrations of MMPs which correlate with clinical severity of ALI/ARDS (12, 17). The inventor's previous findings (25) indicated that the enhancement of NF-κB activation followed by increased release of the active form of MMP-9 are functional consequences of FcγRIIa/TLR4 receptor crosstalk. In the present studies, the two hit model of ALI was used to study the role of Btk in modulating function of alveolar neutrophils. Interestingly, Btk mediates MMP-9 production by alveolar neutrophils in mice with LPS/IC induced ALI. Blocking of Btk in mice with ALI led to inhibition of MMP-9 expression in alveolar neutrophils (FIGS. 6A and B). Moreover, treatment of mice with LPS/IC induced ALI with siRNA specific for MMP-9 conjugated to F(ab')$_2$ fragments of anti-neutrophil antibody caused a significant attenuation of lung injury and lessening of lung dysfunction (FIGS. 6C and 6D).

The role of MMP-9 in ALI is not yet clear, as conflicting reports in the literature show both beneficial and deleterious effects of this proteinase (17). However, the present observations are in line with those of Kim et al. (24) who showed that inhibition of MMP-9 attenuated ventilator induced lung injury in rats.

Based on the present inventor's discovery that specific silencing Btk in alveolar neutrophils protects subjects from lung inflammation/injury, Btk-targeted neutrophil-directed therapy contributes to restoration of homeostasis in lungs of patients with ALI/ARDS.

Figure 9:
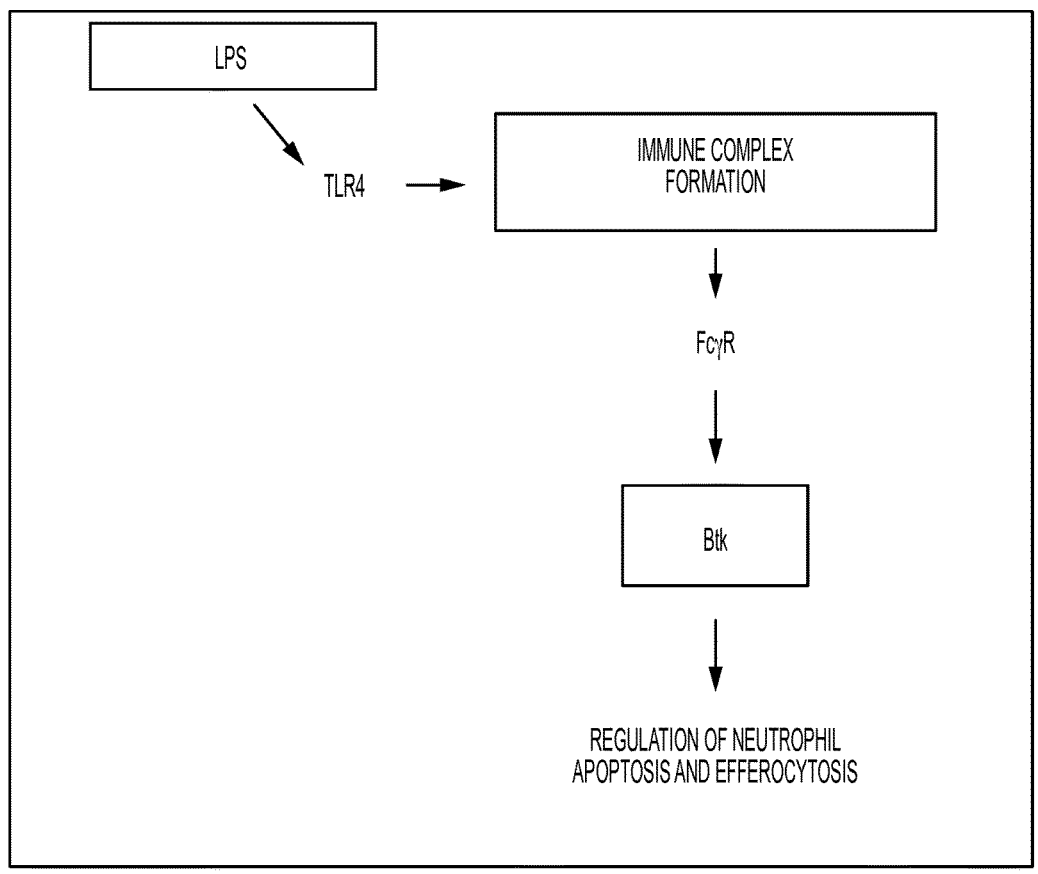
FIG. 9. Summary of findings. LPS triggers formation of immune complexes in lungs, which engage FcγRIIa receptors leading to activation of Btk and regulation of neutrophil apoptosis and efferocytosis (removal or clearance of apoptotic cells).

A summary of the present inventor's findings is presented in FIG. 9. Previous studies indicated that the initial insult (bacterial infection/LPS) subsequently triggered a secondary insult through production of pathogenic ICs in a "two hit" process. The ICs are deposited in lungs of patients with ARDS with the aid of FcγRIIa receptors. Expression of FcγRIIa is substantially elevated in lungs of these patients and FcγRIIa appears on infiltrating neutrophils. Moreover, the Btk pathway mediates pro-inflammatory interaction between ICs and FcγRIIa. According to the present invention, the Btk pathway regulates both apoptosis and efferocytosis of alveolar neutrophils in lungs of subjects with LPS/IC-induced ALI, influenza and other virus-induced ALI, and emphysema/COPD induced, inter alia, by cigarette smoke.

RNA Interference (RNAi) and siRNAs

RNA interference (RNAi) is a relatively recently reported phenomenon that has developed into a new approach for elucidating and modulating gene function (Fire, A et al., Nature 391:806-11, 1998; Tuschl, T et al., Genes Dev 13:3191-97, 1999; Sharp, P. A., Genes Dev. 15:485-90, 2001; Bernstein, E et al., Nature 409:363-66, 2001; Nykanen, A et al., Cell 107:309-21. 2001; Elbashir, S M et al., Genes Dev. 15:188-200, 2001; Elbashir, S M et al., Nature 411:494-98, 2001; Lau, N C. et al. Sci Amer 289: 34-41, 2003); McManus, M T. et al. Nature Rev Genetics 3, 737-47, 2002; and Dykxhoorn, D K et al., Nature Rev Mol Cell Bio 4: 457-67, 2003). RNAi is a sequence-specific, post-transcriptional, gene-silencing mechanism that is effected through RNA molecules, usually double stranded (dsRNA) that are homologous to a sequence of the target gene. Fragments of the dsRNA called "small interfering" RNAs (siRNAs) can rapidly induce loss of function, and only a few molecules are required in a cell to produce the effect (Fire et al., supra) through hybrid formation between a homologous siRNA and mRNA (Lin, S L et al., Curr Cancer Drug Targets 1:241-247, 2001). A member of the RNase III family of nucleases named dicer has been identified as being involved in processing (Bernstein et al., supra). DNA vector-mediated RNAi technology has made it possible to develop therapeutic applications for use in mammalian cells (Sui, G et al., Proc Natl Acad Sci USA 99:5515-20, 2002; McCaffrey, A P et al., Nature 418:38-39, 2002; Lee, N S et al., Nat Biotechnol 20:500-505, 2002). There have been reports of delivery by retroviral vectors for stable expression (Barton, G M et al., Proc Natl Acad Sci USA 99:14943-45, 2002; Paddison, P J et al., Cancer Cell 2:17-23, 2002; Rubinson, D A et al., Nat Genet 33:401-06, 2003; Tiscornia, G et al., Proc Natl Acad Sci USA 100:1844-48, 2003) or adenoviral vectors for transient expression (Xia, H et al., Nat Biotechnol 20:1006-10, 2002).

siRNA suppression or silencing of gene expression through a highly regulated enzyme-mediated process of RNAi involves multiple RNA-protein interactions characterized by four major steps: assembly of siRNA with the RNA-induced silencing complex (RISC), activation of the RISC, target recognition and target cleavage. These interactions may bias strand selection during siRNA-RISC assembly and activation, and contribute to the overall efficiency of RNAi (Khvorova, A et al., Cell 115:209-16, 2003); Schwarz, D S et al. 115:199-208, 2003).

Preferred approaches and algorithms for selecting siRNA sequences to target and silence expression of a selected gene are described, for example, in Far, R K et al., Nuc Acids Res. 31:4417-24, 2003 and Reynolds, A et al., Nature Biotech. 22:326-30, 2004. Far et al. suggests options for assessing target accessibility for siRNA and supports the design of active siRNA constructs in an approach that can be automated, adapted to high throughput and that may include additional parameters relevant to the biological activity of siRNA. To identify siRNA-specific features likely to contribute to efficient processing at each of the steps of RNAi, Reynolds et al., supra performed a systematic analysis of 180 siRNAs targeting the mRNA of two genes. Eight characteristics associated with siRNA functionality were identified: low G/C content, a bias towards low internal stability at the sense strand 3'-terminus, lack of inverted repeats, and sense strand base preferences (positions 3, 10, 13 and 19). Application of an algorithm incorporating all eight criteria significantly improves potent siRNA selection. This highlights the utility of rational design for selecting potent siRNAs that facilitate functional gene knockdown and silencing.

Candidate siRNA sequences against mouse and human Btk can be selected using a process that involves running a BLAST search against the sequence of Btk and selecting sequences that "survive" to ensure that these sequences will not be cross matched with any other genes. siRNA sequences selected according to such a process and algorithm may be cloned into an expression plasmid and tested for their activity in abrogating Btk function in Btk-expressing cells of the appropriate animal species. A number of preferred, but not limiting, sequences of targets and of siRNAs are shown below.

Those sequences that show RNAi activity may, for example, be recloned into a replication-defective human serotype 5 adenovirus (Ad5) to attain high titers of this vector (in the range of $10^{10}$). For example, infection with 100 infectious units/cell ensures all cells are infected. Another advantage of this virus is the high susceptibility and infectivity and the host range (with respect to cell types). Even if expression is transient, cells can go through multiple replication cycles before Btk activity recovers. Moreover, some cells undergo apoptosis in response to expression of the present siRNAs so that even transient expression is adequate to kill the cells if that is the objective. Preferred viral vectors are those with prolonged suppressive, silencing effects on Btk.

In a most preferred embodiment, the inhibitory nucleic acid molecule is a double stranded nucleic acid, preferably an RNA, most preferably an siRNA used in a method of RNAi that results in sequence-specific silencing, e.g., via sequence-specific degradation of homologues in an mRNA. As used herein, the term siNA (small, or short, interfering nucleic acid) is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. Longer ds RNAi's, such a miRNAs, appear to tolerate mismatches more readily than do shorter dsRNAs. In addition, as used herein, the term RNAi is meant to be equivalent to other terms used to describe sequence specific RNA interference, such as post transcriptional gene silencing, or an epigenetic phenomenon. For example, siNA molecules of this are used to epigenetically silence genes at both the pre-transcriptional and, more commonly, the post-transcriptional level.

An siNA can be designed to target any region of the coding or non-coding sequence of an mRNA, preferably the coding sequence. The siRNA's exemplified herein are "targeted to" (which is synonymous with "specific for" or are "complementary to" or "hybridize with" or "hybridize to." coding sequences. A siNA or siRNA is preferably a double-stranded polynucleotide molecule comprising self-complementary sense and antisense regions, wherein the antisense region comprises a nucleotide sequence that is complementary to the nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand and wherein the antisense and sense strands are self-complementary. The siNA can also be assembled from a single oligonucleotide, where the self-complementary sense and antisense regions of the siNA are linked by means of a nucleic acid linker or a non-nucleic acid-based linker. The siNA can be a polynucleotide with a hairpin secondary structure, having self-complementary sense and antisense regions that create the hairpin. The siNA can be a circular single-stranded polynucleotide having two or more loop structures and a stem comprising self-complementary sense and antisense regions which circular polynucleotide can be processed either in vivo or in vitro to generate an active siNA molecule capable of mediating RNAi. The siNA can also comprise a single stranded oligo- or poly-nucleotide having nucleotide sequence complementary to a target nucleotide sequence in a target nucleic acid molecule or a portion thereof, wherein the single stranded oligo- or polynucleotide can further comprise a terminal phosphate group, such as a 5'-phosphate or 5',3'-diphosphate. (See, .g., Martinez, J. et al. *Cell* 110, 563-74, 2002; Schwarz, D S et al., *Molec Cell* 10, 537-68, 2002).

In certain embodiments, the siNA molecule of the invention comprises separate sense and antisense sequences or regions, wherein the sense and antisense regions are covalently linked by nucleotide or non-nucleotide linkers as is known in the art, or are alternately non-covalently linked by ionic interactions, hydrogen bonding, Van der Waal's interactions, hydrophobic interactions, and/or stacking interactions. Some preferred siRNAs are discussed below.

As used herein, siNA molecules need not be limited to those molecules containing only RNA, but further encompasses chemically-modified nucleotides and non-nucleotides. In certain embodiments, the siNA molecules lack 2'-OH— containing nucleotides. In certain embodiments, siNA's do not require the presence of nucleotides having a 2'-OH group, and as such, siNA molecules may optionally not include any "ribonucleotides' (e.g., those nucleotides that have a 2'-OH group); these molecules can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. Such modified siNA molecules have also been referred to as short interfering modified oligonucleotides (siMON). Other chemical modifications, e.g., as described in WO 2003/070918 and WO2003074654 can be applied to any siNA sequence of the invention. In one embodiment, the molecule mediating RNAi has a 2 nucleotide 3' overhang (see several examples below). If the RNAi molecule is expressed in a cell from a construct, for example from a hairpin molecule or from an inverted repeat of the desired sequence, then the endogenous cellular machinery creates the overhangs.

Considerations to be taken into account when designing an RNAi molecule include, e.g., the sequence to be targeted, secondary structure of the RNA target and binding of RNA binding proteins. Again, methods of optimizing siRNA sequences will be evident to the skilled person. Typical algorithms and methods are described in Vickers, T A, et al. *J Biol Chem* 278:7108-18, 2003; Yang, D. et al. *Proc Natl Acad Sci USA* 99:9942-47, 2002; Far et al. (supra); and Reynolds et al. (supra).

Methods of making siRNAs are conventional. In vitro methods include processing the polyribonucleotide sequence in a cell-free system (e.g., digesting long dsRNAs with RNAse III or Dicer), transcribing recombinant double stranded DNA in vitro, and, preferably, chemical synthesis of nucleotide sequences homologous to Btk sequence. See, e.g., Tuschl et al. (1999) *Genes & Dev.* 13:3191-3197. In vivo methods include (1) transfecting DNA vectors into a cell such that a substrate is converted into siRNA in vivo. See, for example, Kawasaki et al., *Nucleic Acids Res* 31:700-7, 2003; Miyagishi et al. *Nature Biotechnol* 20:497-500, 2003; Lee et al. *Nature Biotechnol* 20:500-505, 2003); Brummelkamp et al., *Science* 296:550-53, 2003; McManus, M T et al., *RNA* 8:842-50; 2002; Paddison, P J et al. *Gene Dev* 16:948-58, 2002; Paddison P J et al. *Proc Natl Acad Sci USA* 99:1443-48, 2002; Paul et al., *Nature Biotechnol* 20:505-8, 2002; Sui et al. (supra); Yu et al., *Proc Natl Acad Sci USA* 99:6047-52, 2002);

(2) expressing shRNAs from plasmid systems using RNA polymerase III (pol III) promoters. See, for example, Kawasaki et al., supra; Miyagishi et al., supra; Lee et al., supra; Brummelkamp et al., supra; McManus et al., supra), Paddison et al., supra (both); Paul et al., supra, Sui et al., supra; and Yu et al., supra; and/or (3) expressing short RNA from tandem promoters. See, for example, Miyagishi et al., supra; Lee et al., supra).

When synthesized in vitro, a typical micromolar scale RNA synthesis provides about 1 mg of siRNA, which is sufficient for about 1000 transfection experiments using a 24-well tissue culture plate format. In general, to inhibit Btk expression in cells in culture, one or more siRNAs can be added to cells in culture media, typically at about 1 ng/ml to about 10 µg siRNA/ml.

For further guidance for methods of designing and preparing siRNAs, testing them for efficacy, and using them in methods of RNAi (both in vitro and in vivo), see, e.g., Allshire *Science* 297:1818-19, 2002); Volpe et al., *Science* 297:1833-37, 2002; Jenuwein, *Science* 297:2215-18, 2002); Hall et al. *Science* 297 2232-37, 2002; Hutvagner et al. *Science* 297:2056-60, 2002; McManus et al., supra; Reinhart et al., *Genes Dev.* 16:1616-26, 2002); Reinhart et al., *Science* 297:1831, 2002); Fire et al., supra, Moss *Curr Biol* 11:R772-5, 2001; Brummelkamp et al. *Science* 296:550-53, 2002); Bass, *Nature* 411 428-29, 2001; Elbashir et al., supra; U.S. Pat. No. 6,506,559; US Pat Appl. 2003/0206887; WO99/07409; WO99/32619; WO00/01846; WO 00/44914; WO00/44895; WO2001/29058; WO2001/36646; WO2001/75164; WO2001/92513; WO2001/29058; WO2001/89304; WO2001/90401; WO2002/16620; and WO2002/29858.

Ribozymes and siNAs can take any of the forms, including modified versions, described for antisense nucleic acid molecules; and they can be delivered to cells and introduced into cells as oligonucleotides (single or double stranded) or in the form of an expression vector.

In a preferred embodiment, an antisense nucleic acid, siNA, preferably an siRNA comprises a single stranded polynucleotide comprising a sequence that is at least about 90% or at least about 91%, 92%, 93%, 94%, 95%, 96%, 97%, 98% or 99% identical to or complementary to a segment of the human Btk mRNA or coding DNA sequence (SEQ ID NO:1). As used herein, a DNA and an RNA encoded by it are said to contain the same "sequence," taking into account that the thymine bases in DNA are replaced by uracil bases in RNA.

Active variants (e.g., length variants, including fragments; and sequence variants) of the nucleic acid-based inhibitors, preferably siRNAs, discussed herein are included. An "active" variant is one that retains the activity of the inhibitor from which it is derived (preferably the ability to inhibit Btk gene expression). It is routine to test a variant to determine its activity using conventional procedures.

As for length variants, an antisense nucleic acid or siRNA may be of any length that is effective for inhibition of the Btk gene/coding sequence. Typically, an antisense nucleic acid is between about 6 and about 50 nucleotides (e.g., at least about 12, 15, 20, 25, 30, 35, 40, 45 or 50 nt), and may be as long as about 100 to about 200 nucleotides or more. Antisense nucleic acids may have about the same length as the coding sequence to be inhibited. When referring to length, the terms "bases' and 'base pairs' (bp) are used interchangeably, and will be understood to correspond to single stranded (ss) and double stranded (ds) nucleic acids.

The full length coding sequence (equivalent of mRNA sequence) of human Btk is shown below (SEQ ID NO:1) and includes the stop codon. This corresponds to nt's 1 to 1707 of NCBI (GenBank) reference Sequence: KF241986.1 (a 2417 nt sequence "*Homo sapiens* truncated Bruton agammaglobulinemia tyrosine kinase (BTK) mRNA, complete cds"). See also NM_000061 which is a "*Homo sapiens* Bruton agammaglobulinemia tyrosine kinase (BTK), transcript variant 1, mRNA", a total of 2611 nt's of which nt's 194-2173 constitute the coding sequence). The full sequence of these two database sequence is also incorporated by reference herein, though not shown here.

```
                                                            SEQ ID NO: 1
atg gcc gca gtg att ctg gag agc atc ttt ctg aag cga tcc caa cag      48 aaa aag aaa aca tca cct cta aac ttc aag aag cgc ctg ttt ctc ttg      96 acc gtg cac aaa ctc tcc tac tat gag tat gac ttt gaa cgt ggg aga     144 aga ggc agt aag aag ggt tca ata gat gtt gag aag atc act tgt gtt     192 gaa aca gtg gtt cct gaa aaa aat cct cct cca gaa aga cag att ccg     240 aga aga ggt gaa gag tcc agt gaa atg gag caa att tca atc att gaa     288 agg ttc cct tat ccc ttc cag gtt gta tat gat gaa ggg cct ctc tac     336 gtc ttc tcc cca act gaa gaa cta agg aag cgg tgg att cac cag ctc     384 aaa aac gta atc cgg tac aac agt gat ctg gtt cag aaa tat cac cct     432 tgc ttc tgg atc gat ggg cag tat ctc tgc tgt tct cag aca gcc aaa     480 aat gct atg ggc tgc caa att ttg gag aac agg aat gGA AGC TTA AAA    528

CCT GGG AGt tct cac cgg aag aca aaa aag cct ctt ccc cca acg cct     576
```

-continued

```
gag gag gac cag atc ttg aaa aag cca cta ccg cct gag cca gca gca        624
gca cca gtc tcc aca agt gag ctg aaa aag gtt gtg gcc ctt tat gat        672
tac atg cca atg aat gca aat gat cta cag ctg cgg aag ggt gat gaa        720
tat ttt atc ttg gag gaa agc aac tta cca tgg tgg aga gca cga gat        768
aaa aat ggg cag gaa ggc tac att cct agt aac tat gtc act gaa gca        816
gaa gac tcc ata gaa atg tat gag tgg tat tcc aaa cac atg act cgg        864
agt cag gct gag caa ctg cta aag caa gag GGG AAA GAA GGA GGT TTC        912
Att gtc aga gac tcc agc aaa gct ggc aaa tat aca gtg tct gtg ttt        960
gct aaa tcc aca ggg gac cct caa ggg gtg ata cgt cat tat gtt gtg       1008
tgt tcc aca cct cag agc cag tat tac ctg gct gag aag cac ctt ttc       1056
agc acc atc cct gag ctc att aac tac cat cag cac aac tct gca gga       1104
ctc ata tcc agg ctc aaa tat cca gtg tct caa caa aac aag aat gca       1152
cct tcc act gca ggc ctg gga tac gga tca tgg gaa att gat cca aag       1200
gac ctg acc ttc ttg aag gag ctg gga act gga caa ttt ggg gta gtg       1248
aag tat ggg aaa tgg aga ggc cag tac gac gtg gcc atc aag atg atc       1296
aaa gaa ggc tcc atg tct gaa gat gaa ttc att gaa gaa gcc aaa gtc       1344
atg atg aat ctt tcc cat gag aag ctg gtg cag ttg tat ggc gtc tgc       1392
acc aag cag cgc ccc atc ttc atc atc act gag tac atg gcc aat ggc       1440
tgc ctc ctg aac tac ctg agg gag atg cgc cac cgc ttc cag act cag       1488
cag ctg cta gag atg tgc aag gat gtc tgt gaa gcc atg gaa tac ctg       1536
gag tca aag cag ttc ctt cac cga gac ctg gca gct cga aac tgt TTG       1584
GTA AAC GAT CAA GGA Gtt gtt aaa gta tct gat ttc ggc ctg tcc agg       1632
tat gtc ctg gat gat gaa tac aca agc tca gta ggc tcc aaa ttt cca       1680
gtc cgg tgg tcc cca ccg gag tcc tga                                   1707
```

(568 aa's)
The encoded human Btk protein is shown below using the single letter
designations (See also GenBank: AAB60639.1)

```
                                                          (SEQ ID NO: 2)
MAAVILESIF LKRSQQKKKT SPLNFKKRLF LLTVHKLSYY EYDFERGRRG SKKGSIDVEK        60

ITCVETVVPE KNPPPERQIP RRGEESSEME QISIIERFPY PFQVVYDEGP LYVFSPTEEL      120

RKRWIHQLKN VIRYNSDLVQ KYHPCFWIDG QYLCCSQTAK NAMGCQILEN RNGSLKPGSS      180

HRKTKKPLPP TPEEDQILKK PLPPEPAAAP VSTSELKKVV ALYDYMPMNA NDLQLRKGDE      240

YFILEESNLP WWRARDKNGQ EGYIPSNYVT EAEDSIEMYE WYSKHMTRSQ AEQLLKQEGK      300

EGGFIVRDSS KAGKYTVSVF AKSTGDPQGV IRHYVVCSTP QSQYYLAEKH LFSTIPELIN      360

YHQHNSAGLI SRLKYPVSQQ NKNAPSTAGL GYGSWEIDPK DLTFLKELGT GQFGVVKYGK      420

WRGQYDVAIK MIKEGSMSED EFIEEAKVMM NLSHEKLVQL YGVCTKQRPI FIITEYMANG      480

CLLNYLREMR HRFQTQQLLE MCKDVCEAME YLESKQFLHR DLAARNCLVN DQGVVKVSDF      540

GLSRYVLDDE YTSSVGSKFP VRWSPPES                                        568
```

The full length coding sequence of murine Btk DNA (equivalent to mRNA sequence) is shown below and includes the stop codon (SEQ ID NO:3). This corresponds to nt's 161 to 2140 of NCBI Reference Sequence (GenBank) NM_013482.2—("*Mus musculus* Bruton agammaglobulinemia tyrosine kinase (Btk), mRNA" which is a sequence of) and to nt's 133-2112 of NCBI Reference Sequence (GenBank) L29788.1 ("Mouse Bruton agammaglobulinemia tyrosine kinase (Btk) mRNA, complete cds", which is a sequence of 2468 nt's) the complete sequences of which, though not shown, are also incorporated by reference herein.

```
                                                              SEQ ID NO: 3
atg gct gca gtg ata ctg gag agc atc ttt ctg aag cgc tcc cag cag         48 aaa aag aaa aca tca cct tta aac ttc aag aag cgc ctg ttt ctc ttg         96 act gta cac aaa ctt tca tac tat gaa tat gac ttt gaa cgt ggg aga        144 aga ggc agt aag aaa ggt tca ata gat gtt gag aag atc acc tgt gtt        192 gaa aca gta att cct gaa aaa aat ccc cca cca gaa aga cag att ccg        240 agg aga ggt gag gag tct agt gaa atg gaa cag att tca atc att gaa        288 agg ttc ccg tac cca ttc cag gtt gta tat gat gaa gga cct ctc tat        336 gtt ttc tcc cca act gaa gag ctg aga aag cgc tgg att cac cag ctc        384 aaa aat gta atc cgg tac aat agt gac ctg gta cag aaa tac cat cct        432 tgc ttc tgg att gat gga cag tat ctc tgc tgc tct cag aca gcc aag        480 aat gct atg ggc tgc caa att ttg gag aac agg aat gGA AGC TTA AAA     528

CCT GGG AGt tct cat cga aaa acg aaa aag cct ctt ccc cct acc cca    576 gag gaa gat cag atc ttg aaa aaa ccg ctt ccc cgg agc cca aca gca        624 gca cca atc tcc aca acc gag ctg aaa aag gtc gtg g*cc ctt tat gat*      672

*tac atg cca atg aa*c gca aat gac tta caa ttg cga aag ggc gag gag      720 tat ttt atc ctg gag gag agc aac cta ccg tgg tgg cga gca cga gat        768 aaa aat ggg cag gaa ggc tac atc cca agt aac tat atc act gaa gct        816 gag gac tcc ata gag atg tat gag tgg tat tcc aag cac atg act cga        864 agt caa gct gag caa ctg cta aag caa gag GGG AAA GAA GGA GGT TTC    912

Att gtc aga gac tcc agc aaa gct gga aaa tac acc gtg tct gtg ttt    960 gct aaa tct act ggg gag cct caa ggg gtg atc cgc cat tac gtt gtg       1008 tgt tcc acg cca cag agc cag tat ctg gct gag aaa cac ctc ttc           1056

*agc acc atc cct gag ctc att aac ta*c cat caa cac aac tct gca ggc     1104 ctc ata tcc agg ctg aaa tat cct gtg tct aaa caa aac aaa aac gcg       1152 cct tct act gca ggc ctg ggc tat gga tca tgg gaa att gat cca aag       1200 gac ctc acc ttc ttg aag gag ctt g*gg act gga caa ttc ggt gtc gtg*    1248

*aaa tat g*gg aag tgg agg ggc caa tat gat gtg gcc atc aag atg atc     1296 aga gaa ggt tcc atg tcg gag gat gaa ttc att gaa gaa gcc aaa gtc       1344 atg atg aat ctt tcc cat gag aag ctg gtg cag ttg tat ggc gtc tgc       1392 acc aaa caa cgc ccc atc ttc atc atc acc gag tac atg gct aat ggc       1440 tgc ctc ttg aac tac ctg agg gag atg cgg cac cgc ttc cag aca cag       1488 cag ctg ctt gag atg tgc aaa gat gtc tgt gaa gca atg gaa tac ttg       1536 gag tcg aag cag ttc ctt cac aga gac ctg gca gct cga aac tgt TTG   1584

GTA AAC GAT CAA GGA Gtt gtg aaa gta tct gac ttt ggc ctg tct agg    1632 tat gtc ctt gat gat gag tac acc agc tct gta ggc tcc aag ttt cca       1680 gtc cgg tgg tct cca cca gaa gtg ctt atg tat agc aag ttc agc agc       1728
```

```
-continued
aaa tct gac atc tgg gct ttt ggg gtt tta atg tgg gag atc tac tcc    1776 ctg ggg aag atg ccg tat gag aga ttt act aac agt gag aca gca gaa    1824 cac att gct caa ggc tta cgt ctc tac agg cct cat ctg gca tca gag    1872 agg gta tat acc atc atg tac agc tgc tgg cac gag aaa gca gat gaa    1920 cgt cct agt ttc aaa att ctc ttg agt aac att cta gat gtg atg gat    1968 gaa gaa tcc tga                                                     1980

The amino acid sequence of the encoded murine
BTK protein is shown below
                                                         (SEQ ID NO: 4)
MAAVILESIF LKRSQQKKKT SPLNFKKRLF LLTVHKLSYY EYDFERGRRG SKKGSIDVEK    60

ITCVETVIPE KNPPPERQIP RRGEESSEME QISIIERFPY PFQVVYDEGP LYVFSPTEEL   120

RKRWIHQLKN VIRYNSDLVQ KYHPCFWIDG QYLCCSQTAK NAMGCQILEN RNGSLKPGSS   180

HRKTKKPLPP TPEEDQILKK PLPPEPTAAP ISTTELKKVV ALYDYMPMNA NDLQLRKGEE   240

YFILEESNLP WWRARDKNGQ EGYIPSNYIT EAEDSIEMYE WYSKHMTRSQ AEQLLKQEGK   300

EGGFIVRDSS KAGKYTVSVF AKSTGEPQGV IRHYVVCSTP QSQYYLAEKH LFSTIPELIN   360

YHQHNSAGLI SRLKYPVSKQ NKNAPSTAGL GYGSWEIDPK DLTFLKELGT GQFGVVKYGK   420

WRGQYDVAIK MIREGSMSED EFIEEAKVMM NLSHEKLVQL YGVCTKQRPI FIITEYMANG   480

CLLNYLREMR HRFQTQQLLE MCKDVCEAME YLESKQFLHR DLAARNCLVN DQGVVKVSDF   540

GLSRYVLDDE YTSSVGSKFP VRWSPPEVLM YSKFSSKSDI WAFGVLMWEI YSLGKMPYER   600

FTNSETAEHI AQGLRLYRPH LASERVYTIM YSCWHEKADE RPSFKILLSN ILDVMDEES    659
```

Human Btk and mouse Btk DNA nt coding sequences (mRNA coding sequences) are 92.3% identical over 1704 aligned nt's. Human Btk and mouse Btk aa sequences are 98.6% identical over 568 aligned aa's.

sequence 7 of human Btk differs in 4 nt's from the murine Target sequence 6 (in same location). Target sequences 1-3 are shown in Heinonen J E et al., *FEBS Lett.* 527:274-78, which describes these three siRNA targets and ds siRNA molecules that are specific for them.

TABLE 1

Examples of Target Sequences in Human and Mouse Btk

| Target | Target Sequence | SEQ ID NO: | Location (in Human and Mouse Btk mRNA or cDNA coding sequences |
|---|---|---|---|
| 1 | TTGGTAAACGATCAAGGAG | 5 | 518-536 of SEQ ID NOs: 1 and 3 |
| 2 | GGGAAAGAAGGAGGTTTCA | 6 | 895-913 of SEQ ID NOs: 1 and 3 |
| 3 | GAAGCTTAAAACCTGGGAG | 7 | 1582-1600 of SEQ ID NOs: 1 and 3 |
| 4 | CCCTTTATGATTACATGCCAATGAA | 8 | 662-686 of SEQ ID NOs: 1 and 3 |
| 5 | GCACCATCCCTGAGCTCATTAACTA | 9 | 1058-1082 of SEQ ID NOs: 1 and 3 |
| 6 | GGACAATTCGGTGTCGTGAAATATG | 10 | 1231-1255 SEQ ID NO: 3 |
| 7 | GGACAATTTGGGGTAGTGAAGTATG* | 11 | 1231-1255 SEQ ID NO: 1 |

*positions at which human Btk (SEQ ID NO: 1 differs from murine Btk (SEQ ID: 3 are underscored The length of an effective siNA is generally between about 15 bp and about 29 bp, preferably between about 19 and about 29 bp, e.g., about 15, 16, 17, 18, 19, 20, 21, 22, 23, 24, 25, 26. 27, 18 or 29 bp, with shorter and longer sequences being acceptable. Generally, siNAs are shorter than about 30 bases to prevent eliciting interferon effects.

Table 1 shows preferred Btk target sequences of the present invention to which the siRNA's of the present invention are targeted. Target sequences 1-5 are identical in human and murine Btk cDNA (and mRNA). Target The location of target sequences 1-3 in human and murine Btk nucleic acid coding sequences are shown as bold, uppercase characters in SEQ ID NOs:1 and 3 above. The location of target sequences 4-7 in human and murine Btk nucleic acid coding sequences are shown as bold, italic, lowercase characters in SEQ ID NOs:1 and 3 above.

The specific target sequences of human Btk and the specific sequences of the appropriate siRNA in Table 2 are preferred but are not the only ones included within the scope of this invention. Thus, any oligonucleotide run of Btk cDNA or RNA of similar length as disclosed more generally herein, can be targeted with siRNA and can serve as a target for RNAi and inhibition of ALI as disclosed herein. Likewise, a siRNA similar to those specific sequences listed above can be prepared and employed wits its complementary target sequence in the present methods. For example, an active variant of an siRNA having, for one of its strands, the 19 nucleotide core sequence of any of siRNA's 1-3 (SEQ ID NO:12-17) or the 25 nt sequence of any of siRNA's 4-7 (SEQ ID NO; 18-25) herein can lack base pairs from either, or both, ends of the dsRNA; or can comprise additional base pairs at either, or both, ends of the ds RNA, provided that the total of length of the siRNA is preferably between about 19 and about 29 bp (not including the overhangs). One embodiment of the invention is an siRNA that "consists essentially of" sequences represented by SEQ ID NO:12-25 or complements thereof. The term "consists essentially of" is an intermediate transitional phrase, and in this case excludes, for example, sequences that are long enough to induce a significant interferon response. A siRNA of the invention may consist essentially of between about 19 and about 29 bp in length or about 21 and about 31 nt's in length if 2 nt overhangs are present.

expected due to genetic mutation, polymorphism, or evolutionary divergence and to encompass all known or yet unknown allelic variants thereof. An example of such divergence is the 4 nt difference between target sequences SEQ ID NOs:10 and 11 (and, hence, ds siRNA's #6 and #7). The variant sequences may be artificially generated. Nucleic acid sequences with a small insertion or a small deletions (preferably of no more than 3 nt), or with a single point mutation/substitution relative to the target sequence can be effective inhibitors.

The degree of sequence identity may be optimized by sequence comparison and alignment algorithms well-known in the art (see, for example Gribskov and Devereux, Sequence Analysis Primer, W.H. Freeman, N Y, 1991), and references cited therein and calculating the percent difference between the nucleotide sequences by, for example, the Smith-Waterman algorithm as implemented in the BESTFIT software program using default parameters (e.g., University of Wisconsin Genetic Computing Group). At least about 90% sequence identity is preferred (more preferably at least about 92%, 93%, 94%, 95%, 96%. 97%, 98% or 99%) between the inhibitory nucleic acid, preferably a siRNA, and the targeted nucleotide sequence of Btk, preferably human

TABLE 2

Examples of Btk-specific siRNA Sequences
(for Targets Sequences 1-7 above

| siRNA # | siRNA Sequence* | sense/antisense | SEQ ID NO: |
|---|---|---|---|
| 1 | 5'-uugguaaacgaucaaggag<u>uu</u>-3'<br>3'-<u>uu</u>aaccauuugcuaguuccuc-5' | sense<br>antisense | 12<br>13 |
| 2 | 5'-gggaaagaaggagguuuca<u>uu</u>-3'<br>3'-<u>uu</u>cccuuucuuccuccaaagu-5' | sense<br>antisense | 14<br>15 |
| 3 | 5'-gaagcuuaaaaccugggag<u>uu</u>-3'<br>3'-<u>uu</u>cuucgaauuuuccacccuc-5' | sense<br>antisense | 16<br>17 |
| 4 | 5'-cccuuuaugauuacaugccaaugaa-3'<br>3'-uucauuggcauguaaucauaaaggg-5' | sense<br>antisense | 18<br>19 |
| 5 | 5'-gcaccaucccugagcucauuaacua-3'<br>3'-uaguuaaugagcucagggauggugc-5' | sense<br>antisense | 20<br>21 |
| 6 | 5'-ggacaauucggugucgugaaauaug-3'<br>3'-cauauuucacgacaccgaauugucc-5' | sense<br>antisense | 22<br>23 |
| 7 | 5'-ggacaauuugggguagugaaguaug-3'<br>3'-cauacuucacuaccccaaauugucc-5' | sense<br>antisense | 24<br>25 |
| 8<br>(control) | 5'-uuccucuccacgcgcaguacauuua-3'<br>3'-uaaauguacugcgcguggagaggaa-5' | sense<br>antisense | 26<br>27 |

*siRNA duplexes 1-3 were synthesized with a complementary "core" sequence for the target plus a 2 nt deoxythymidine 3'-overhangs (underscored) as described by Elbashir et al. Genes Dev., 2001, supra. In siRNA #7, the positions in both strands that differ from their corresponding positions in siRNA #6 are noted by bold/italic/underscored characters. Control siRNA #8, SEQ ID NO: 26/27 were designed to have no homology to any known vertebrate gene and not to induce a significant response in silencing Btk.

As for sequence variants, it is generally preferred that an inhibitory nucleic acid, whether an antisense nucleic acid, a ribozyme (the recognition sequences), a siNA, preferably a siRNA comprise a strand that is completely complementary to (or identical to the complement of) a sequence of the target sequence of a target nucleic acid that it is designed to inhibit. However, 100% complementarity/sequence identity is not required for the siRNA to function and thus be included within the scope of this invention. Thus, the siRNA of the present invention has the advantage of being able to tolerate and accommodate naturally occurring sequence variations, for example, in human Btk that might be Btk. Defined alternatively, an active variant of an inhibitory nucleic acid, preferably of an siRNA, of this invention is one that hybridizes to the sequence it is intended to inhibit under conditions of high stringency. For example, the duplex region of an siRNA may be defined functionally as a nucleotide sequence that is capable of hybridizing with a portion of the target gene transcript in vitro under high stringency conditions (e.g., 400 mM NaCl, 40 mM PIPES pH 6.4, 1 mM EDTA, 50° C. or 70° C., hybridization for 12-16 hours), followed generally by washing.

Delivery and expression and action of the siRNA compositions of the present invention in the lungs as described herein, preferably via intranasal administration, inhibit Btk expression in alveolar neutrophils which inhibition has been exemplified here as inhibition of lung injury in several murine models of ALI, whether induced by LPS/ICs acute infection with Flu virus, or exposure to second hand smoke (SHS) in a model of COPD. siRNA specific for murine Btk conjugated or linked to anti-neutrophil antibody and administered into mice intranasally inhibited lung injury by the relevant "pathogen" as shown histopathologically and otherwise. Thus the compositions used in the methods of the present invention are useful for inhibitory "nucleic acid" (siRNA) therapy of acute or chronic lung diseases in humans.

Molecules that Bind to Neutrophils for Delivery of Btk-siRNA to the Lung

Studies disclosed herein used a mAb specific for neutrophils for lung delivery of siRNA targeted to mouse Btk in several murine models of lung disease. The exemplified mAb in these studies was the murine mAb Ly6G 1A8 (Clone 1A8, Catalog # BE0075-1, Bio X Cell, West Lebanon, N.H.). An F(ab')$_2$ fragment of this mAb was able to deliver the siRNA alveolar neutrophils in the lungs of mice with ALI. Conjugation or chemical linkage of an RNAi, preferably a siRNA, is be performed using any method known in the art that preserves (i) the ability of the antibody, fragment or derivative thereof to bind to its target antigen/epitope on neutrophils in vivo, and (i) the ability of the conjugated or linked siRNA to enter the cell and bind specifically (hybridize) to an mRNA target sequence to mediate its silencing/inhibitory effect.

For treatment of such conditions in humans, antibodies, preferably mAbs or antigen-binding fragments thereof that are specific for human neutrophils are used for delivery. The antibodies useful in the present invention are those specific for a neutrophil surface marker or antigen. The term "antibody" refers both to monoclonal antibodies (mAbs), antibodies in polyclonal antisera derived from the sera of animals immunized with an immunogen comprising the neutrophil marker/antigen. MAbs are may be obtained by methods known to those skilled in the art (e.g., Harlow, E. et al., Using Antibodies: A Laboratory Manual: Portable Protocol NO. 1, Cold Spring Harbor Laboratory Press, Cold Spring Harbor, N.Y., 1998). Mabs may be of any immunoglobulin (Ig) isotype including IgG, IgM, IgE, IgA, IgD and any subclass thereof. Antibodies also include chimeric antibodies described below. The term "antibody" is also meant to include both intact four-chain Ig molecules as well as antigen-binding fragments thereof, such as, for example, Fab, F(ab')$_2$ and Fv as well as single chain antibodies (scFv) which bind the antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316-25, 1983). It will be appreciated that Fab, F(ab')$_2$, Fv and scFv fragments or forms of the antibodies useful in the present invention are used to deliver of Btk siRNA to neutrophils, preferably in the lungs, in the same manner as an intact antibody. Conventional fragments are typically produced by proteolytic cleavage, using enzymes such as papain (for Fab fragments) or pepsin (for F(ab')$_2$ fragments). Fv fragments are described in (Hochman, J. et al. *Biochemistry* 12:1130-35, 1973; Sharon, J, et al., *Biochemistry* 15:1591-94, 1976). A "single-chain antibody" (scFv; also termed "scAb") is a single chain polypeptide molecule wherein an Ig V$_H$ domain and an Ig V$_L$ domain are artificially linked by a short peptide linker that allows the scFv to assume a conformation which retains antigen-specificity and antigen-binding capacity for the antigen/epitope to which the original antibody (from which the V$_H$ and V$_L$ domains are derived) was specific. See, for example, Skerra, A. et al. *Science* 240: 1038-41, 1988; Pluckthun, A. et al. *Methods Enzymol.* 178: 497-515, 1989; Winter, G. et al. *Nature*, 349:293-99), 1991; Bird, R E et al., *Science* 242:423-25, 1988; Huston, J S et al., *Proc. Natl. Acad. Sci. USA* 85:5879-83, 1988; U.S. Pat. Nos. 4,704,692, 4,853,871, 4,946,778, 5,260,203, 5,455,030.

Chimeric antibodies are Ig molecules wherein different parts of the molecule are derived from different animal species. An example is an Ig having a variable region derived from a murine mAb and a human Ig constant region. A preferred chimeric antibody (or antigen-binding fragment thereof) of the present invention for use in humans has as much of the constant region derived from human Ig and as little as necessary of the variable region, preferably only the complementarity-determining regions or CDRs) derived from the mouse mAb with the specificity for a human neutrophil marker/antigen. Chimeric antibodies and methods for their production are known in the art (Cabilly, S. et al, *Proc. Natl. Acad. Sci. USA* 81:3273-77, 1984; U.S. Pat. No. 4,816,567 (Mar. 28, 1989) and U.S. Pat. No. 6,331,415 (Dec. 18, 2001); Morrison, S. et al., *Proc. Natl. Acad. Sci. USA* 81:6851-55, 1984; EP 173494 (Mar. 5, 1986); Boulianne, G L et al., *Nature* 312:643-46, 1984; Neuberger M S et al., *Nature* 314:268-70, 1985; WO 86/01533 (Mar. 13, 1986); Taniguchi, T et al., EP 171496 (Feb. 19, 1985); Kudo et al., EP 184187 (Jun. 11, 1986); Sahagan, B G et al., *J. Immunol.* 137:1066-74, 1986; Liu, A Y et al., *Proc. Natl. Acad. Sci. USA* 84:3439-43, 1987; Sun, L K et al., *Proc. Natl. Acad. Sci. USA* 84:214-18, 1987; Better, M et al., *Science* 240:1041-43, 1988. These references are hereby incorporated by reference.

The binding activity of an antibody specific for a neutrophil marker/antigen may be determined according to well known methods, such as enzyme immunoassay (EIA), particularly an enzyme linked immunosorbent assay (ELISA) or radioimmunoassay (RIA) of by immunocytochemical or immunohistochemical means (as exemplified in the examples below. Such immunoassays are described in Butler, J. E., The Behavior of Antigens and Antibodies Immobilized on a Solid Phase (Chapter 11) In: *Structure of Antigens*, Vol. 1 (Van Regenmortel, M., CRC Press, Boca Raton 1992, pp. 209-259; Butler, J. E., ELISA (Chap. 29), In: van Oss, C. J. et al., (eds), *Immunochemistry*, Marcel Dekker, Inc., New York, 1994, pp. 759-803; Butler, J. E. (ed.), *Immunochemistry of Solid-Phase Immunoassay*, CRC Press, Boca Raton, 1991; Voller, A. et al., *Bull. WHO* 53:55-65 (1976); Voller, A. et al., *J. Clin. Pathol.* 31:507-520 (1978); Weintraub, B., *Principles of Radioimmunoassays*, 7$^{th}$ Training Course on Radioligand Assay Techniques, The Endocrine Society, March, 1986; Chard, T., An Introduction to Radioimmune Assay and Related Techniques, in: Work, T. S. et al., *Laboratory Techniques and Biochemistry in Molecular Biology*, North Holland Publishing Company, NY, (1978). Those skilled in the art will be able to determine operative and optimal assay conditions for each determination by employing routine experimentation.

The above antibodies/fragments are can be specific for any neutrophil cell surface marker, more preferably markers such as human CD66b (=CD67), CD177, CD15 and CD16, most preferably markers that are unique to, or most selectively expressed on, neutrophils, such as CD66b and CD177.

CD66b also designated CD67 and carcinoembryonic antigen-related cell adhesion molecule 8 (CEACAM8 and non-specific cross-reacting antigen (NCA-) is encoded by the CEACAM8 (CGM6) gene and is exclusively expressed in neutrophils and eosinophils, particularly in granulocytes in the spleen, thymus and lungs, attached to the membrane by a GPI-anchor. For a review, see, e.g., Futosi K et al., *Int Immunopharmacol.* 17:638-50, 2013). The protein is also found in the secondary granules in the cytoplasm. Surface CD67 is upregulated upon granulocyte activation. CD67 binds heterophilically with CD66c, which is coexpressed with CD67 in granulocytes. Anti-CD67/CD66b mAbs are available from a number of standard commercial sources; non-limiting examples are GM2H6 from Santa Cruz Biotechnology (Dallas Tex.) and G10F5 from BioLegend (San Diego Calif.).

CD177 is a GPI-anchored glycoprotein present mainly on neutrophils (also known as PRV1). Fore a review, see, e.g., Muschter S et al., *Curr Opin Hematol.* 18:452-60, 2011. Its plasma membrane expression is increased during inflammation (or exposure to granulocyte colony stimulating factor (G-CSF) and pregnancy. Maternal antibodies against CD177 have been implicated in neonatal alloimmune neutropenia (see, e.g., Curtis B R et al., *Transfusion.* 45:1308-13, 2005). Anti-CD177 mAbs of different isotypes are known in the art and available from known commercial sources, e.g., MEM-166, C-5 and C1.

CD15 is 3-fucosyl-N-acetyllactosamine (3-FAL), also known as Lewis X, 3-FAL, X-hapten, and SSEA-1. For reviews, see, e.g., Hakomori S., *Histochem J.* 24:771-6, 1992; Munro J M, *Eur Heart J.* 14 *Suppl K:* 72-7, 1993). CD15 is involved in adhesion, chemotaxis, phagocytosis, and bactericidal activity. Many anti-CD15 mAbs have been produced are of various isotypes (IgM, IgG1 or IgG3) and can be obtained from various standard commercial sources. Non-limiting examples are HI98, TG1, 3G75, 1-BB-22E1, MCS-1-581, 4-00E-10, BRA-4F1, C3D-1, By87a, VIM-C6, 28 and CHO131. The hybridoma CSLEX1 (producing a mAb against sialyl-CD15) may be obtained from American Type Culture Collection (ATCC, Manassas, Va.)

CD16 is a low affinity IgG receptor III (FcγRIII) that is expressed as two distinct forms (CD16a and CD16b). (For reviews, see, e.g., Edberg J C et al. *Immunol Res.* 11:239-51, 1992; Tsokos G C et al., *Curr Opin Rheumatol.* 10:417-25, 1998.) Of these, markers, CD16b (or FcγRIII$_B$) is a 48 kD glycosylphosphatidylinositol (GPI)-anchored protein expressed specifically on neutrophils (Selvaraj P, *Immunol Res.* 29:219-30, 2004). CD16b binds aggregated IgG or IgG-antigen complex which functions in cell activation, phagocytosis, and antibody-dependent cell-mediated cytotoxicity. Many anti-CD16 or CD16b mAbs have been produced, are of various isotypes and can be obtained from various standard commercial sources. Non-limiting examples are the anti-CD16b mAb Z64 and the anti-CD16 mAbs DJ130c, 3G8, Y-15, YFC 120.5, GRM1, MEM-154, LNK16, B-E16, 2Q1240, ASH 1975

Additional delivery molecules to deliver Btk-targeted siRNA to alveolar neutrophils in accordance with this invention are ligands for neutrophil-specific cell surface molecules. These can be soluble proteins including extracellular domains of such proteins that are normally expressed as cell-surface proteins or shorter neutrophil binding peptide fragments of these molecules. Such proteins or peptides are used to deliver siRNA targeted Btk to alveolar neutrophils. The two best known ligands are CD31 and CD66c.

CD31, also know as Platelet endothelial cell adhesion molecule (PECAM-1) is a CD177 ligand that is normally found on endothelial cells, platelets, macrophages/Kupffer cells, neutrophils, T lymphocytes, NK cells, megakaryocytes, and osteoclasts. Soluble PECAM-1 has been described by Muller's group (e.g., Liao F et al. *J Exp Med* 185:1349-57, 1997; *J Immunol* 163:5640-48, 2000) and is discussed in a review (Ilan N et al. *Curr Opin Cell Biol* 15:515-24, 2003). Soluble CD31 is available commercially (e.g., from Sino Biological, Inc., Beijing, China).

CD66c, also known as carcinoembryonic antigen-related cell adhesion molecule 6 protein (CEACAM6) is a ligand for CD66b (=CD67). See, for example, Skubitz K M et al. *J Biol Regul Homeost Agents* 13):244-5, 1999. This protein occurs naturally as a highly glycosylated 90 kDa, 286 aa, GPI-linked membrane protein, is found in azurophilic granules in cells of the granulocyte lineage and serves as an intercellular adhesion molecule, forming homotypic and heterotypic bonds with CD66b. CD66c or peptides thereof are available commercially, e.g., from R&D Systems (now Biotechne; Minneapolis Minn.) and Novus Biologicals (Littleton Colo.). CD66c or a neutrophil binding domain or peptide thereof can be used to deliver siRNA targeted to Btk to alveolar neutrophils in accordance with this invention.

Small Molecule Inhibitors of Btk for Treating Lung Injury

The present invention is also directed to method of inhibiting Btk in lung neutrophils by treatment of subject in need thereof, preferably a human with ALI, with an organic small molecule Btk inhibitor.

Btk is intimately involved in multiple signal-transduction pathways regulating survival, activation, proliferation, and differentiation of B lymphoid cells. Because Btk is overexpressed and constitutively active in several B-lineage lymphoid malignancies, it has become a molecular target of new drugs for treatment of B-lineage leukemias and lymphomas; preclinical and early clinical results indicate such treatment utility (D' Cruz. O J et al., *Onco Targets and Therapy* 6:161-76, 2013). The following small-molecule Btk inhibitors in development were listed there:

| Company | Compound | Indications | Stage of Development |
|---|---|---|---|
| Pharmacyclics, Janssen | Ibrutinib/ PCL-32765 | R/R CLL/SLL, MCL, FL, DLBCL, MM, indolent NHL, MALT/MZL | Phase Ib/ IIPhase III(CLL/ NHL) |
| Pharmacyclics, Janssen | PCL-32765 + rituximabPCL-32765 + ofatumumabPCL-32765 + bendamustine and rituximab | R/R CLL/SLLHigh-risk CLL | Phase IIPhase III |
| Avila Therapeutics, Celgene | AVL-292 | CLL, B-cell NHL, WM | Phase Ib |
| Bristol-Myers Squibb | Dasatinib + fludarabine | R/R CLL/SLL | Phase II |
| University of Southern California | LFM-A13 | B-cell malignancies | Preclinical |
| Ono Pharmaceutical | ONO-WG-307 | B-cell malignancies | Preclinical |
| Genentech, Gilead | GDC-0834 | B-cell malignancies | Preclinical |

Abbreviations:
DLBCL, diffuse large B-cell lymphoma; R/R CLL/SLL, relapsed/refractory chronic lymphocytic leukemia/small lymphocytic lymphoma; MCL, mantle-cell lymphoma; FL, follicular lymphoma; MM, multiple myeloma; NHL, non-Hodgkin's lymphoma; MALT/MZL, mucosa-associated lymphoid tissue/marginal zone lymphoma; WM, Waldenström macroglobulinemia.

A number of Btk inhibitors which have been discovered are also useful in the present invention as a means to treat ALI as discussed above and as exemplified below. A preferred inhibitor is the covalent inhibitor ibrutinib/PCI-32765 (Pharmacyclics), a potent selective and irreversible inhibitor of Btk at the nanomolar level and targets the Cys-481 residue in the enzyme's active site (Pan Z et al., *Chem Med Chem* 2:58-61, 2007).

Of the dianilinopyrimidine-based irreversible Btk inhibitors (with micromolar activity) which have been developed, two lead compounds are AVL-101 and AVL-291 (Avila Therapeutics). Dasatinib®/Sprycel, a breakpoint cluster region Abelson (BCR-Abl) kinase inhibitor which (approved for treatment of chronic myelogenous leukemia) is a potent Btk inhibitor (Marcotte D J et al. *Protein Sci.* 19:429-39, 2010; Hantschel 0 et al., *Proc Natl Acad Sci USA.* 104:13283-88, 2007). The knowledge of the X ray crystal structure coordinates of the Btk kinase domain serve as the basis for further development of rationally designed Btk inhibitors (Marcotte et al. supra; Mao C et al. *J Biol Chem.* 276:41435-43, 2001).

Covalent Btk inhibitors include ibrutinib/PCI-32765 whose chemical structure is shown below, AVL-101, and AVL-291/292. Conventional small-molecule inhibitors interact with high affinity in the binding site of a protein target, and the drug-target complex is favored when plasma drug concentration is high. Covalent inhibitors form high-affinity interactions with the binding site of the protein target and can bring a low-reactivity "warhead" into close proximity to a structurally unique amino acid followed by covalent bonding to lock the drug to its target, thereby silencing the target's activity. This couples the pharmacodynamic behavior of a compound to protein half-life and turnover rather than pharmacokinetic properties.

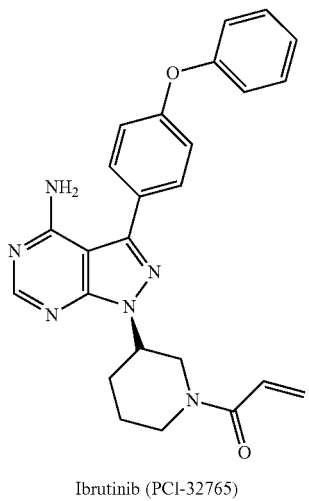

Ibrutinib (PCI-32765)

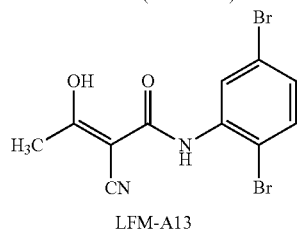

LFM-A13

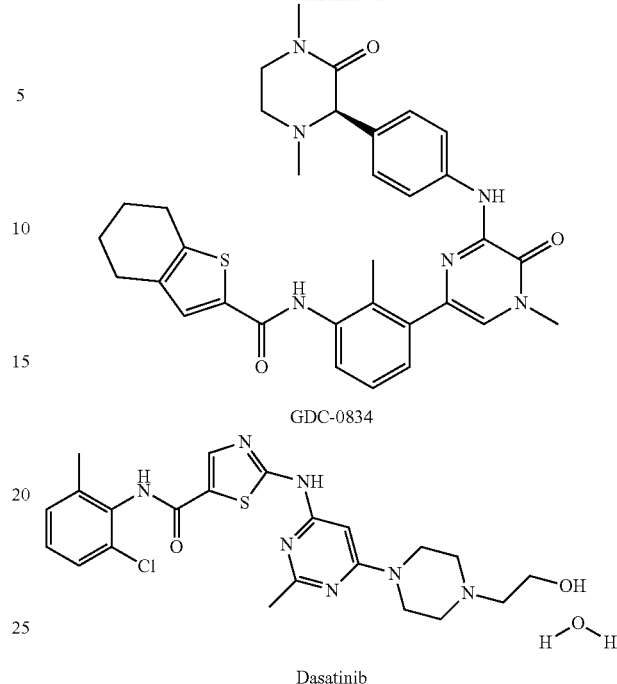

GDC-0834

Dasatinib

LFM-A13, GDC-0834, and Dasatinib are noncovalent adenosine triphosphate-competitive Btk inhibitors.

Ibrutinib/PCI-32765 whose chemical name is (1-[(3R)-3-[4-amino-3-(4-phenoxyphenyl)-pyrazolo[3,4-d]pyrimidin-1-yl]piperidin-1-yl]prop-2-en-1-one) is a small-molecule inhibitor that forms an irreversible bond with Cys-481 in the active site of Btk and inhibits Btk phosphorylation on Tyr223, resulting in Btk inhibition with an $IC_{50}$ of 0.5 nM (Pan et al. supra). In vitro studies demonstrated that PCI-32765 blocks B cell receptor (BCR)-stimulated activation of ERK1/2, PI3K, and NF-κB, inhibits growth, and induces apoptosis and activation-induced proliferation of certain chronic lymphocytic leukemia (CLL) cell lines (Herman S E et al., *Blood.* 23:6287-96, 2011). PCI-32765 also targets not monocytes, macrophages, and mast cells and inhibits TNF-α, IL-1β, and IL-6 production (in primary monocytes (Chang B Y et al. *Arthritis Res Ther.* 4:R115, 2011).

PCI-32765 is active in various in vivo models, including (1) a transgenic murine model of BCR-driven lymphoma, (2) spontaneous B-cell lymphoma in canines, and (3) mouse models of autoimmune disease and at TCL1 transgenic mouse model of CLL which has been validated as a model for human CLL. PCI-32765 induced objective clinical responses in dogs with a spontaneous B-cell non-Hodgkin's lymphoma (Honigberg L A et al., *Proc Natl Acad Sci USA* 107:13075-80, 2010).

AVL-101, AVL-291, and AVL-292 (Avila Therapeutics/Celgene Corporation) are active dianilinopyrimidine-based irreversible Btk inhibitors with micromolar activity (against lymphoma cells). 136 AVL-101/291/292 covalently modify their targets, leading to nonspecific and durable silencing of the targeted proteins, including PDGFR, c-Kit, EGFR, and Btk, in vitro, ex vivo and in vivo. At low μM concentrations, AVL-101 inhibited the Tec family of kinases (Bmx, Btk, Itk) as well as JAK 2, Aurora A, fibroblast growth factor receptor (FGFR)-1, Flt4, Ret, and TrkA. AVL-291/292 also inhibited the Tec family of kinases (Bmx, Btk, Tec) as well as JAK2, JAK3, Txk, Flt4. 136 AVL-101 disrupts the BCR-signaling pathway. AVL-101 inhibited the proliferation of B-cell lymphomas in vitro. AVL-101 inhibited Btk-dependent B-cell function in vivo. These properties support the potential of AVL-101/291/292 in the present invention.

AVL-291 selectively and potently inhibited Btk and BCR signaling in vitro and was efficacious in a variety of animal disease models. AVL-292 inhibited osteoclast function and reduced osteoclast-stimulated proliferation 0.139 AVL-291 modified the course of rheumatoid arthritis (RA) in animal models, with 75% inhibition of the clinical score (at an oral dose of 3 mg/kg that correlated directly with 75% Btk target occupancy) 0.140 AVL-291 reduced clinical arthritis scores, inflammation, joint damage, cartilage damage, and bone erosion in the collagen-induced arthritis models of RA. Complete inhibition of the disease correlated with complete target occupancy at 10 mg/kg. Thus, AVL-291 is expected to be useful for patients with lymphoid malignancies and RA and other autoimmune diseases. AVL-292 is currently being investigated in autoimmune diseases as well as in B-cell malignancies and. has demonstrated biological activity in CLL patients and preclinically in prevention of bone destruction.

Noncovalent Btk inhibitors, are exemplified by Dasatinib® (Sprycel/BMS-354825, Bristol-Myers Squibb) whose IUPAC name is [N-(2-chloro-6-methylphenyl)-2-(6-(4-(2-hydroxyethyl) piperazin-1-yl)-2-methylpyrimidin-4-ylamino) thiazole-5-carboxamide] (and its chemical structure is shown above). Dasatinib®/Sprycel is a potent inhibitor of Btk (105,144) and a potent inhibitor of multikinase BCR/Abl and Src family TKI (and is approved for treatment of CML)/and A chemical proteomics-profiling approach identified the Tec kinases Btk and Tec to be very prominent targets of dasatinib (Hantschel et al., supra; Hallaert D Y et al. *Blood* 112:5141-49, 2008). The gatekeeper residue of Btk which is as a critical determinant for LFM-A13 (α-cyano-β-hydroxy-βeta-methyl-N-(2,5-ibromophenyl) propenamide) (see chemical structure above) is a rationally designed selective Tec family kinase inhibitor. LFM-A13 binds to the catalytic pocket of the kinase domain. In vitro, LFM-A13 inhibited recombinant Btk with an $IC_{50}$ value of 2.5 µM without affecting enzymatic activity of other protein tyrosine kinases at concentrations as high as 278 µm. Particularly relevant to the present invention, its effects were virtually identical to those of Btk-specific siRNA duplexes that target human Btk mRNA (Heinonen J E et al., *FEBS Lett.* 527:274-78, 2002; Kim Y J et al., *Mol Cell Biol.* 24:9986-99, 2004, The only other kinase affected by this inhibitor was polo-like kinase (Plk), but none of 12 other kinases (Uckun F M et al., *Br J Haematol.* 148:714-25, 2010).

GDC-0834 (Genentech, Gilead), IUPAC name is [R—N-(3-(6-(4-(1,4-dimethyl-3-oxopiperazin-2-yl) phenylamino)-4-methyl-5-oxo-4,5-dihydropyrazin-2-yl)-2-methylphenyl)-4,5,6,7-tetrahydrobenzo[b]thiophene-2-carboxamide] (structure shown above) is a reversible, adenosine triphosphate-competitive small-molecule inhibitor of Btk that inhibited Btk phosphorylation (p-Btk) in in vitro assays and in vivo in rodents. GDC-0834 inhibited p-Btk-Y223 with an in vitro $IC_{50}$ of 5.9 nM and 6.4 nM in biochemical and cellular assays, respectively, and in vivo $IC_{50}$ of 1.1 and 5.6 µM in mouse and rat, respectively. GDC-0834 prevented murine and human B-cell proliferation in response to BCR or CD40 stimulation and suppressed arthritis in the prophylactic rat collagen model in a dose-dependent manner.

In summary, a number of small molecule Btk inhibitors are emerging, which have utility in the present invention to inhibit alveolar neutrophil Btk in the treatment of ALI. Some of these have been found to be well tolerated in humans. Even if covalent inhibition of Btk function is accompanied by inhibition of a number of—other kinases and potential side effects such as thrombocytopenia, localized administration to the lungs, such as by intranasal route, as disclosed herein, would be expected to minimize such toxicities. In contrast, rationally designed noncovalent Btk inhibitors which show potential as antileukemia/antilymphoma drug candidates would also be useful in the present and novel application to ALI.

The preferred animal subject of the present invention is a mammal. The invention is particularly useful in the treatment of human subjects. By the term "treating" is intended the administering to subjects of a pharmaceutical composition comprising a siRNA specific for Btk, preferably human Btk, preferably conjugated to an anti-neutrophil antibody or an antigen-binding fragment thereof, preferably a mononuclear antibody (or fragment) specific for human neutrophils.

Administration may be by parenteral, subcutaneous (sc), intravenous (iv), intramuscular, intraperitoneal, transdermal routes or by intranasal (i.n.) administration, inhalation or lung instillation. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein siRNA of the appropriate sequence, preferably conjugated or linked to a neutrophil ligand, preferably a conjugate with an anti-neutrophil antibody, more preferably a mAb or antigen-binding fragment thereof, or a small organic Btk inhibitor molecule is contained in an amount effective to achieve its intended purpose. While individual needs vary, determination of optimal ranges of effective amounts of each component is within the skill of the art. Typical dosages comprise 0.1 to 500 mg/kg/body wt, though more preferred dosages are described for certain particular uses.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired.

In addition to the pharmacologically active inhibitory siRNA conjugate or small organic molecule, the pharmaceutical preparations may contain suitable pharmaceutically acceptable carriers comprising excipients and auxiliaries which facilitate processing of the active compounds into preparations which can be used pharmaceutically as is well known in the art. Suitable solutions for administration by injection or orally, may contain from about 0.01 to 99 percent, active compound(s) together with the excipient.

The pharmaceutical compositions of the present invention are manufactured in a manner which is itself known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the proteins in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension.

The pharmaceutical formulation for systemic administration according to the invention may be formulated for enteral, parenteral administration or administration by inhalation or intranasal administration or lung instillation; and more than one of these formulations may be used concurrently to achieve effective levels and localization of the active ingredient.

For intranasal administration and lung instillation, aerosolized solutions are used. In a sprayable aerosol preparations, the active siRNA or conjugate thereof, or small organic molecule, may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the active ingredient of the invention.

Other pharmaceutically acceptable carriers the present composition are liposomes and nanoparticle, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The methods of this invention are used to treat ALI, ARDS, etc. in a subject in need thereof. The active nucleic acid conjugate or small organic molecule or pharmaceutically acceptable salt thereof is preferably administered in the form of a pharmaceutical composition as described above.

Dosage forms preferably include pharmaceutical dosage units comprising an effective amount of the therapeutic agent. Dosage unit form refers to physically discrete units suited as unitary dosages for a mammalian subject, preferably a human. Each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects By an effective amount is meant an amount sufficient to achieve a regional concentration or a steady state concentration in vivo which results in a measurable reduction in any relevant parameter of disease, as is well-known in the art.

The amount of active compound to be administered depends on the nucleic acid conjugate or small organic molecule that is selected, the state of the disease or condition, the route of administration, the health and weight of the recipient, the existence of other concurrent treatment, if any, the frequency of treatment, the nature of the effect desired, for example, silencing/inhibition of alveolar neutrophil Btk, and the judgment of the skilled practitioner.

A preferred single dose, given once daily for treating a subject, preferably a mammal, more preferably human who his suffering from or susceptible to ALI is between about 0.1 mg/kg and about 250 mg/kg, preferably between about 10 mg/kg and about 50 mg/kg, for example, via instillation (by inhalation). Such a dose can be administered daily for anywhere from about 3 days to one or more weeks. Chronic administration is also possible, though the dose may need to be adjusted downward. The foregoing ranges are, however, suggestive, as the number of variables in an individual treatment regime is large, and considerable excursions from these preferred values are expected.

For continuous administration, e.g., by a pump system such as an osmotic pump, a total dosage for a time course of about 1-2 weeks is preferably in the range of 1 mg/kg to 1 g/kg, preferably 20-300 mg/kg, more preferably 50-200 mg/kg. After such a continuous dosing regiment, the total concentration of the peptide is preferably in the range of about 0.5 to about 50 µM, preferably about 1 to about 10 µM.

Effective doses and optimal dose ranges may be determined in vitro or in vivo using methods well-known in the art, including method described herein.

Having now generally described the invention, the same will be more readily understood through reference to the following examples which are provided by way of illustration, and are not intended to be limiting of the present invention, unless specified.

EXAMPLE I

Materials and Methods

Animal Studies: All studies involving animals were approved by the appropriate committees at the University of Texas Health Science Center, and conform to National Institutes of Health guidelines. Human studies were also approved by relevant institutional committees.

BALB/c mice (Taconic Germantown, N.Y.) were first injected intraperitoneally (i.p.) with either LPS or saline and 8 h later received anti-KC:KC immune complexes or saline (control) by intranasal (i.n.) route. Anti-KC:KC immune complexes were prepared according to the protocol routinely used in our laboratory (28). Some mice received Btk specific siRNA intranasally. In other experiments the animals were treated i.n. with siRNA specific for Btk (see SEQ ID NOs:18-25) or MMP-9 (Invitrogen), both conjugated (T3™-MAX Conjugation Kit (Bioo Scientific Corporation, Austin, Tex.) to F(ab')$_2$ fragments of anti-mouse neutrophil antibody Ly-6G1A8). F(ab')$_2$ fragments alone or conjugated to control siRNA (SEQ ID NO's 26 and 27) (Invitrogen) served as controls of the treatment. Two or fourteen hours after i.n. administration of either immune complexes or saline, the animals were euthanized and samples collected for further evaluation. To study role of neutrophil FcγRIII receptors neutrophils were first depleted by i.p. injection of vinblastine (31) followed by adoptive transfer of cells deficient in FcγRIII receptors prepared as described below. In these experiments purified bone marrow neutrophils (BMPMN) were transfected with siRNA specific for FcγRIII or control siRNA conjugated to fluorescein (FITC; Santa Cruz Biotechnology) according to a previously described procedure (37). Lung dysfunction was assessed by analysis of pulmonary histopathology.

Influenza Virus infections: Mice in the Flu study were infected with a sublethal dose of the Flu virus (mouse adapted H1N1/PR8) by the intranasal (i.n.) route (Z. Sever-Chroneos et al., *Antiviral Res.* 92:319-328, 2011).

Second Hand Smoke (SHS)-Induced COPD: Chronic exposure of mice to SHS induces abnormal pulmonary inflammation, airway remodeling and airspace enlargement due to destruction of alveolar walls which are characteristic of COPD (Pappas et al., supra). The present studies used both wild-type (WT) mice exposed to SHS and apolipoprotein E-(ApoE$^{-/-}$)-genetically deficient mice to study comorbidities of COPD. The targeted deletion of the apoE gene leads to severe hypercholesterolemia and spontaneous atherosclerosis. Lesions of ApoE$^{-/-}$ mice resemble their human counterparts and develop over time from initial fatty streaks to complex lesions. (A high-fat, high-cholesterol diet can strongly accelerate the process.) Exposure of ApoE$^{-/-}$ mice to SHS triggers characteristic decline of lung function that is seen in patients with COPD (Arunachalam, G. et al., supra). ApoE$^{-/-}$ mice were fed a regular diet (control) and a high fat/cholesterol (1%) diet to shorten the time required for the development of atherosclerosis.

WT and ApoE$^{-/-}$ diet groups were divided into equal subgroups: control and SHS. SHS groups were exposed to cigarette smoke for 4 h per day, 5 days a week, for up to 20 weeks. A Teague TE-10 microprocessor-controlled smoking machine was used to produce side stream mixed with a smaller amount of main stream smoke. The chamber (28× 19×15 inches) generates smoke with a particulate value (total suspended particles or TSP) of ~80 mg/m$^3$. The standard exposure conditions were 40 cigarettes at 3 cigarettes/cycle taking close to 2 h to complete. TSP values were measured twice a week or as necessary. Using 4 cigarettes/cycle the TSP count was around 115 mg/m$^3$. Sham controls were exposed to filtered ambient air.

Treatment with Antibody-conjugated siRNA or Btk Inhibitors

Mice were treated i.n. with siRNA specific for Btk conjugated (T3™-MAX Conjugation Kit [Bioo Scientific Corporation, Austin, TX) to F(ab')$_2$ fragments of anti-mouse neutrophil antibody (clone Ly-6G1A8). Btk-specific siR-NA's used are siRNA's #4-6 in Table 2. F(ab')$_2$ fragments conjugated control siRNA (Invitrogen) served as controls for this treatment. Control siRNA #8, SEQ ID NO:26/27 was designed to have no homology to any known vertebrate gene and not to induce a significant response in silencing Btk. In some experiments the animals received i.n. a specific inhibitor of Btk (Pharmacyclics, Inc.).

Seven days after i.n. administration of either therapeutic, mice were euthanized and samples collected for further evaluation. Lung dysfunction was assessed using Computer Tomography (CT) and by analysis of pulmonary histopathology.

Treatment of "COPD" Mice: Animals were injected i.v. with the Btk inhibitor PCI-32765 (Selleck Chemicals). Treatments were started after 7 weeks of CS exposure/western diet and animals were treated twice a week for 4 weeks while continuing regular chronic smoke exposure and a "western" diet.

Pulmonary Histopathology: Lungs were fixed in ExCell-Plus (AMTS, Lodi, Calif.), embedded in paraffin, and sectioned at 5 μm. After staining with hematoxylin and eosin, the sections were photographed using Olympus DP12 camera attached to Olympus BX41 microscope. The images of stained sections were evaluated for the presence of alveolar exudate, infiltration of inflammatory cells, and interstitial thickening. Lung Injury Score (LIS) was assessed as described earlier (28). Most images were assessed at magnification of over 400×. The grading system was based on previously published histopathologic criteria for evaluating the extent of lung tissue damage and ranged from 0 (no changes) to 2 (significant changes). At the minimum twenty sections from each group of mice were evaluated and 4 investigators participated in the analysis of 50 or more fields per group. According to recommendation of "An Official American Thoracic Society Workshop Report: Features and Measurements of Experimental Acute Lung Injury in Animals" (*Am J Respir Cell Mol Biol* 44 725-738, 2011) more than 20 high power fields were independently scored (as described above) and at least 50% of each field was occupied by lung alveoli.

In the COPD model, PicroSirius Red staining of lung sections is used with plane polarized light to visualize collagen content of the airway walls. This method is known to have higher specificity for collagen as well as allowing detection of very fine fibers missed by traditional trichrome methods. Hart's Elastin stain was used to visualize airspace elastin in order to detect strand breaks in alveolar walls.

Cell Counts and Cytology in BAL Fluid: Total cell numbers were assessed using a hemocytometer. To determine cell types in BAL fluid, 5×10$^5$ cells were mounted on slides by cytospin centrifugation. BAL fluid cells were identified and counted microscopically after differential staining using a HEMA 3 stain kit (Fisher Diagnostics, Pittsburgh, Pa.). In addition, slides were photographed obtained using Olympus DP12 camera attached to an Olympus BX41 microscope.

Western Blotting: BAL fluids were subjected to SDS PAGE electrophoresis, transferred onto PVDF membrane and further evaluated for the presence of thrombomodulin using anti-mouse TM antibody (M-17; Santa Cruz Biotechnology, Santa Cruz, Calif.). In some experiments cell culture media or cell lysates were analyzed for level of MPO or actin (EMD Millipore, Billerica, Mass. and Santa Cruz Biotechnology, respectively) or phospho-p40 phox (Santa Cruz Biotechnology).

Laser Confocal Microscopy: Purified alveolar neutrophils mounted on cytospins were incubated with the following primary antibodies: anti-mouse Btk, anti-mouse MyD88, anti-mouse MMP-9 (Santa Cruz Biotechnology), and anti-mouse pBtk (Invitrogen, Grand Island, N.Y.). Species specific antibodies conjugated with fluorescent dyes were subsequently applied to slides. Lung tissue sections, processed as routinely done in our laboratory (26, 28), were incubated with anti-mouse FcγRIII antibody (R&D Systems, Minneapolis, Minn.), or anti-mouse MMP-9 antibody (Santa Cruz Biotechnology), or with anti-neutrophil (Ly6G1A8) antibody (Bio X Cell, West Lebanon, N.H.) followed by fluorescence dye-conjugated secondary antibodies. Hoechst 33342 (Calbiochem, San Diego, Calif.) was employed to stain nuclei. Laser confocal microscopy was performed using PerkinElmer Ultra VIEW LCI confocal imaging system with Nikon TE2000-S fluorescence microscope and PlanApox60 immersion oil objective (numerical aperture [NA] 1.4) at room temperature. Ultra VIEW Imaging Suite software (version 5.5.0.4) was used for image processing.

Neutrophil Apoptosis/Uptake: Purified alveolar neutrophils were evaluated for the presence of cleaved caspase 3 as done routinely in our laboratory (13). Cells mounted on cytospins were incubated with anti-mouse cleaved caspase 3 antibody (Cell Signaling Technology, Danvers, Mass.), followed by dye-conjugated secondary antibody. Fluorescence intensity of cleaved caspase 3 was analyzed as described above. In addition, alveolar neutrophils were co-cultured with mouse spleen macrophages for 1 h (43, 44), and percentage of phagocytosed neutrophils was calculated. In separate sets of experiments bone marrow neutrophils (BMPMNs) were purified according to the previously published protocol (54) and cultivated for 24 h to induce spontaneous apoptosis. Some cells were cultured in the presence of LPS and anti-KC:KC immune complexes. In other experiments, BMPMNs were treated with siRNA specific for Btk (Santa Cruz Biotechnology) conjugated to F(ab')₂ fragments of the Ly6G1A8 antibody. Similarly conjugated control siRNA (Santa Cruz Biotechnology) or F(ab')₂ fragments of the Ly6G1A8 alone served as controls.

Intravital Microscopy: Animal handling procedures were approved by the Louisiana State University (LSU) Health Institutional Animal Care and Use Committee and were in accordance with the guidelines of the American Physiological Society. Neutrophil adhesion to endothelium (intravital microscopy technique) was performed as described previously (50). Briefly, mice were anesthetized with ketamine hydrochloride (150 mg/kg body weight, i.p.) and xylazine (7.5 mg/kg body weight, i.p.) and prepared cremaster muscle was superfused with bicarbonate buffered saline (BBS) at a rate of 1 ml/min (50). A leukocyte was considered adherent if it remained stationary for ≥30 s (#/mm² vessel surface) and was measured off-line for the duration of each observation period. Leukocyte emigration was measured at the end of each 1 min observation period. Emigrated leukocytes were expressed as the number of interstitial leukocytes per mm² of view adjacent to the segment under observation (#/mm² interstitium). Additionally, blood samples were collected to calculate the number of circulating leukocytes.

Statistics: Differences between groups were evaluated by a simple one-way ANOVA or t test when appropriate. All pair-wise multiple comparisons were performed using the Fisher's least significant differences method. A P value of less than 0.05 was considered significant. All statistics were performed using SigmaStat (SPSS Science, Chicago, Ill.).

EXAMPLE II

Two Hit Model of LPS/IC Induced Acute Lung Injury

The present inventor previously postulated that FcγRIIa receptors may control inflammatory responses in lungs of patients with ALI/ARDS (3, 14). Further, the inventor's recent study has shown that LPS triggers an increase in expression of FcγRIIa on the neutrophil surface, and this leads to augmentation of neutrophil responses to stimulation with anti-IL-8:IL-8 immune complexes (25). Importantly, the existence of the molecular cooperation between FcγRIIa and TLR4 receptors in alveolar neutrophils from patients with ALI/ARDS (25) was noted. In order to mimic closely the succession of inflammatory events in lungs of patients with ALI/ARDS, the present inventor developed a two hit model of lung injury in which mice are first treated with LPS, then after 8 h with anti-KC:KC immune complexes (LPS/IC). KC (C-X-C motif ligand 1 or CXCL1) is an early response chemokine in mice responsible for the initial influx of neutrophils to the alveolar compartment, and shares more common properties with human IL-8 than MIP-2 (6, 51). Further, anti-KC:KC immune complexes contribute in a significant way to severe lung inflammation in LPS treated mice and the pro-inflammatory activity of these complexes is mediated by IgG receptors (FcγRs) (14, 26, 28).

Figure 1A:
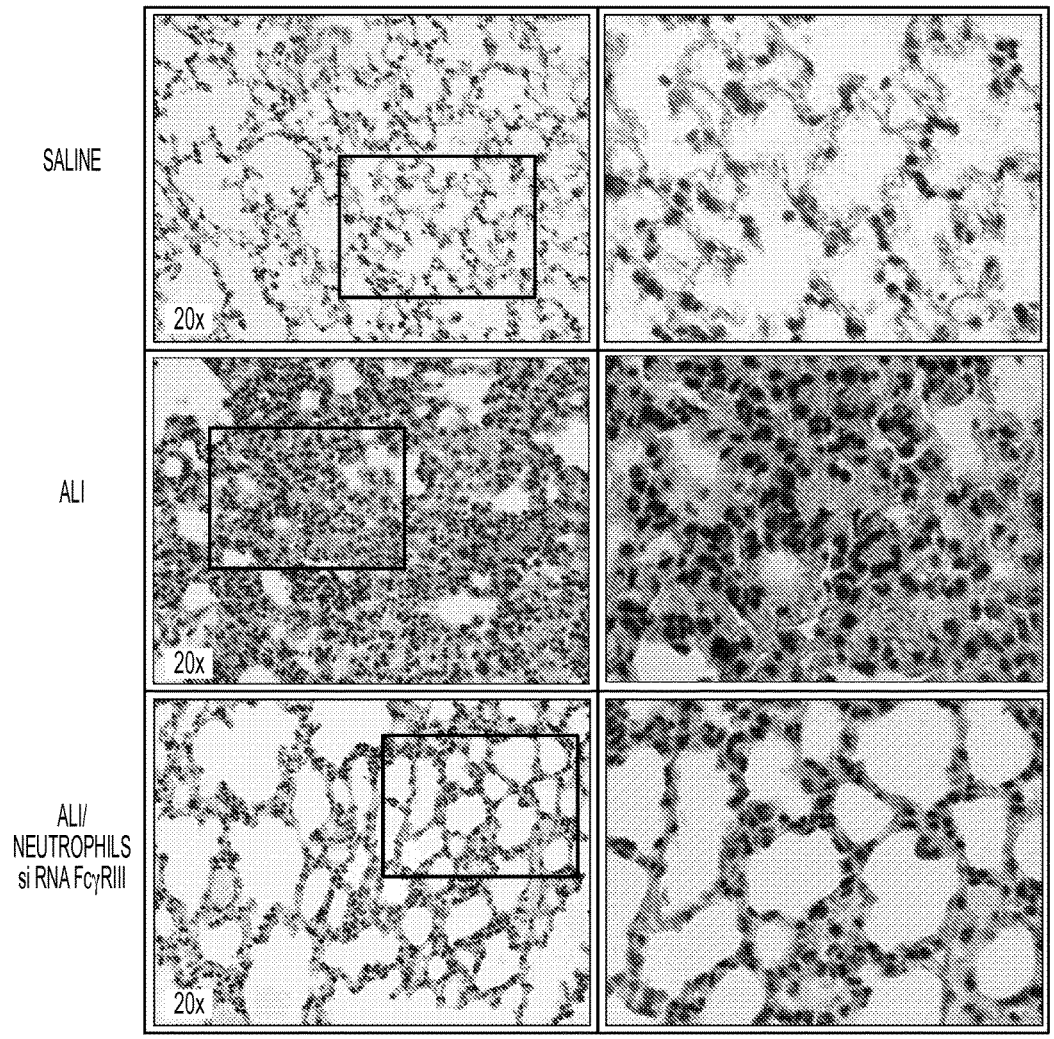
FIGS. 1A-1D.

Histopathological changes characteristic of the lung in ALI/ARDS were alveolar hemorrhage, interstitial thickening, and the presence of alveolar exudate. Further noted was evidence of increased infiltration of inflammatory cells when analyzing lung tissue sections from the present model of ALI-LPS/IC induced lung injury (FIG. 1A; Table 3).

TABLE 3

Lung Injury Induced by LPS and Immune Complexes

| Treatment | Lung Injury Score | | |
|---|---|---|---|
| | Edema fluid | Thickening of alveolar septa | Inflammatory infiltration |
| Saline | 0.000 ± 0.000 | 0.103 ± 0.178 | 0.193 ± 0.109 |
| ALI | 1.624 ± 0.176* | 1.581 ± 0.337* | 1.662 ± 0.245* |
| ALI/siRNA-Btk | 0.243 ± 0.225 | 0.110 ± 0.120 | 0.076 ± 0.094 |
| ALI/Neutrophils siRNA-FcγRIII | 0.323 ± 0.046 | 0.131 ± 0.075 | 0.030 ± 0.052 |

Values are means ± SD.
Analysis was done for 3 animals per group.
*P < 0.001 compared with remaining groups of mice To study the role of neutrophil FcγRIII receptors in this model neutrophils were depleted with vinblastine and an adoptive transfer was performed using cells deficient in FcγRIII receptors. Replenishing of neutrophils with the cells lacking FcγRIII receptors (FIG. 1B) led to significant attenuation of alveolar inflammatory responses and lung injury in LPS/IC induced ALI (FIG. 1A) that is most likely due to the inability of anti-KC:KC ICs to trigger activation of neutrophils via these receptors. To validate this assumption mice were immunized with KC and then administered this protein intratracheally to promote the formation and deposition of anti-KC:KC immune complexes in lungs (anti-KC:KC IC model of ALI, (28)), and subsequently depleted neutrophils. Removal of neutrophils in this group of mice significantly attenuated lung inflammation (FIG. 1C and Table 4.; Anti-KC:KC IC ALI/Vinblastine group).

Figure 1B:
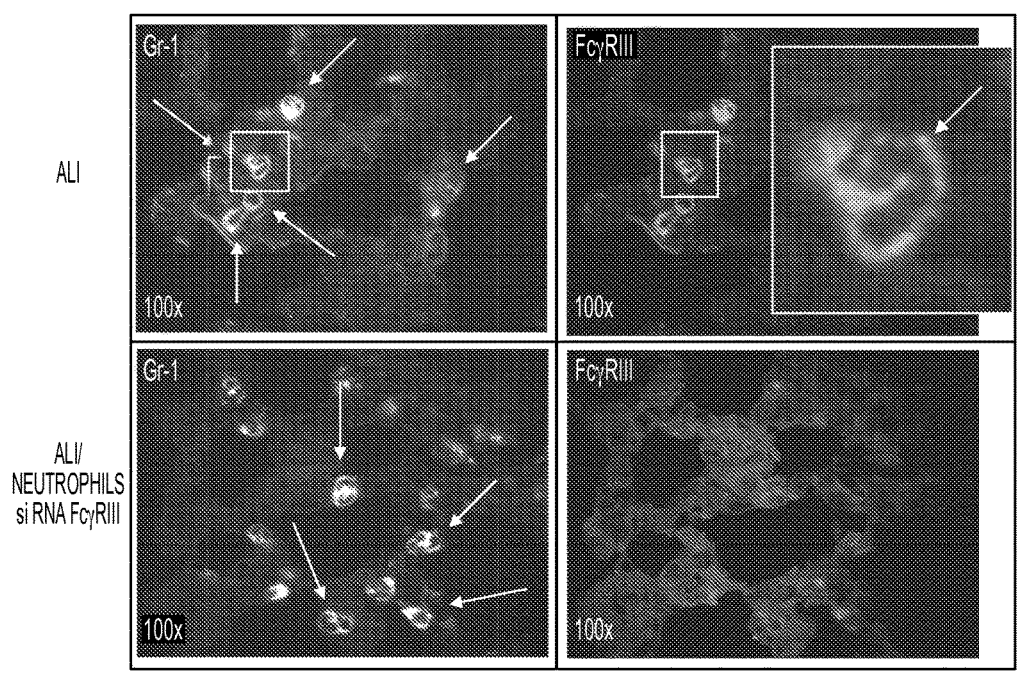
Figure 1C:
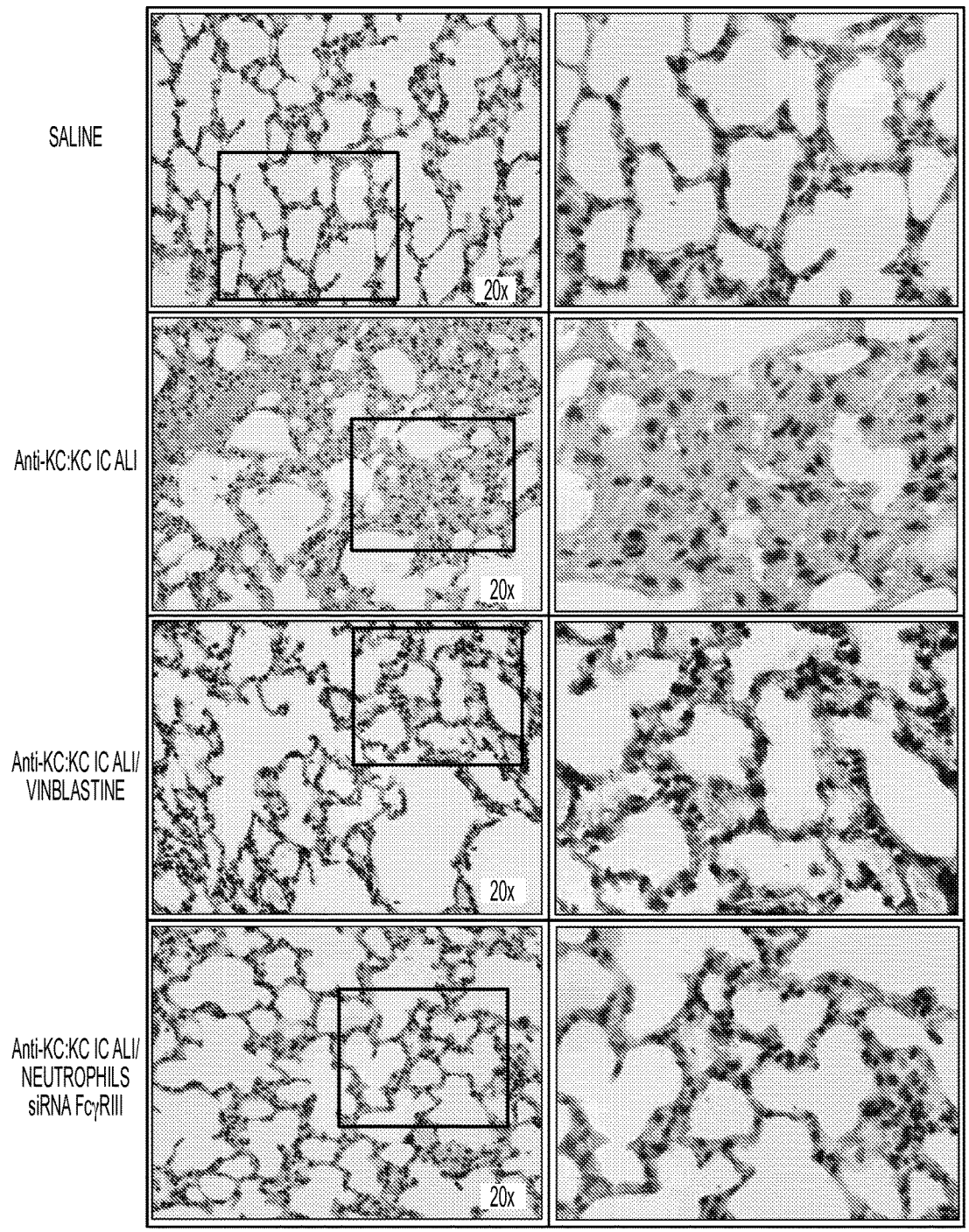
Figure 1D:
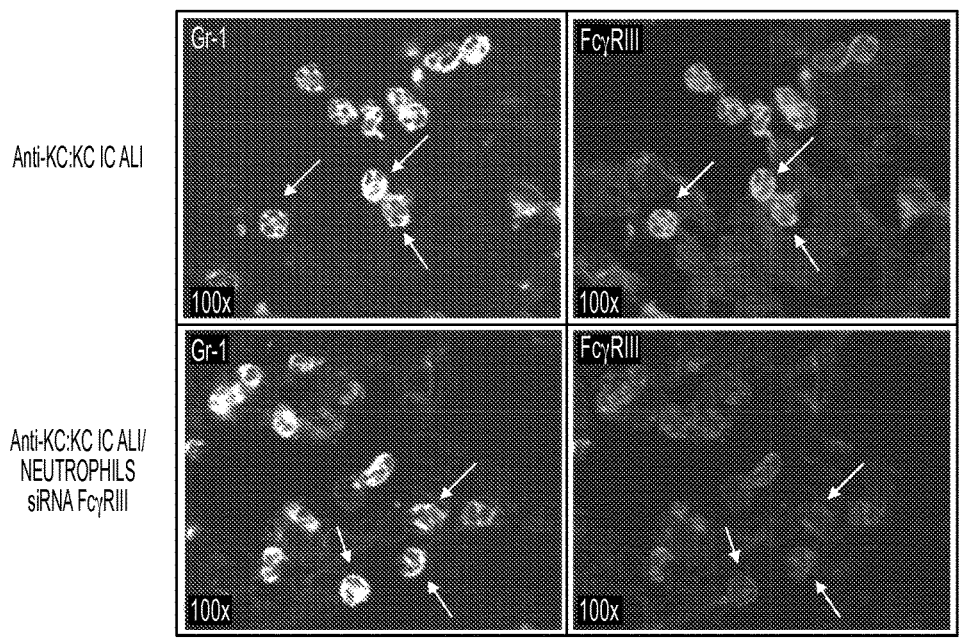
Figure 1E:
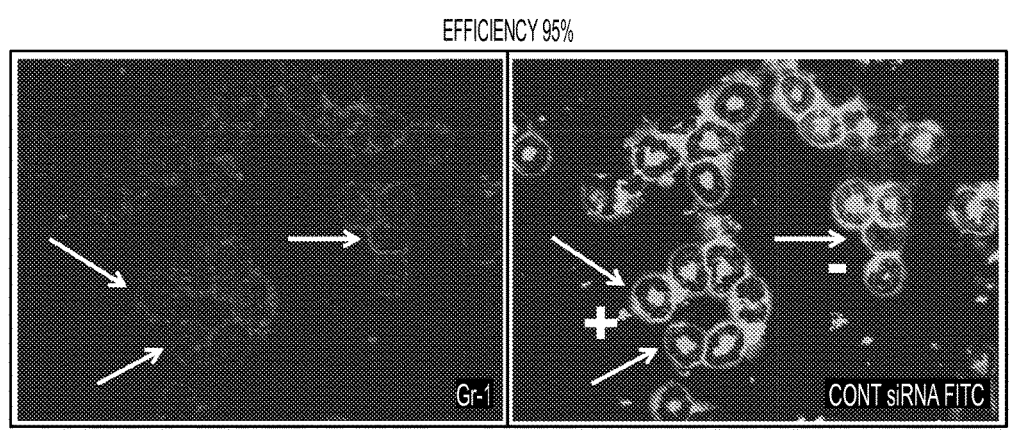
FIG. 1E: Efficiency of transfection of bone marrow neutrophils (neutrophil marker Gr-1-cells "outlined" in white in left panel; control siRNA/FITC-bright fluorescence). Approximately 300 cells were analyzed; typical findings are presented.

Moreover, mice that received neutrophils deficient in FcγRIII receptors were also protected from development of lung inflammation/injury (FIG. 1C; Anti-KC:KC IC ALI/Neutrophils siRNA FcγRIII group). Expression of Fcγ RIII receptors is depicted in FIGS. 1B and D. Fcγ RIII receptors were present in lung tissue neutrophils of mice with LPS/IC induced ALI and anti-KC:KC IC ALI but not in cells from the animals which received Fcγ RIII deficient neutrophils (FIGS. 1B and D). The efficiency of transfection was calculated using a confocal microscopy and is approximately 95% (FIG. 1E).

TABLE 4

Lung Injury with Immune Complexes: Removal of Neutrophils-

| Treatment | Lung Injury Score | | |
|---|---|---|---|
| | Edema fluid | Thickening of alveolar septa | Inflammatory infiltration |
| Saline | 0.017 ± 0.029 | 0.167 ± 0.076 | 0.083 ± 0.144 |
| Anti-KC:KC ALI | 1.667 ± 0.284* | 1.733 ± 0.225* | 1.633 ± 0.202* |
| Anti-KC:KC ALI/vinblastine | 0.033 ± 0.029 | 0.133 ± 0.153 | 0.167 ± 0.029 |
| Anti-KC:KC ALI/Neutrophils siRNA FcγRIH | 0.201 ± 0.043 | 0.187 ± 0.234 | 0.196 ± 0.194 |

Values are means ± SD.
Analysis was done for 3 animals per group.
*P < 0.001 compared with remaining groups of mice

EXAMPLE III

Signaling Events in Alveolar Neutrophils from Mice with LPS/IC Induced Acute Lung Injury As stated above, the existence of Btk dependent cooperation between FcγRIIa and TLR4 signaling cascades in alveolar neutrophils from patients with ALI/ARDS was shown. Therefore, the expression and activation of Btk in lung neutrophils from the two hit model of ALI was analyzed.

Mouse alveolar neutrophils were purified from mice treated with LPS and immune complexes (LPS/IC) as well as mice treated with LPS and Saline (LPS/Sal). The cells were stained using specific antibodies and secondary antibodies conjugated with a fluorescent dye. Florescence intensity was measured for over 100 cells and graphed as fold over average fluorescence value for a control group.

Figure 2A:
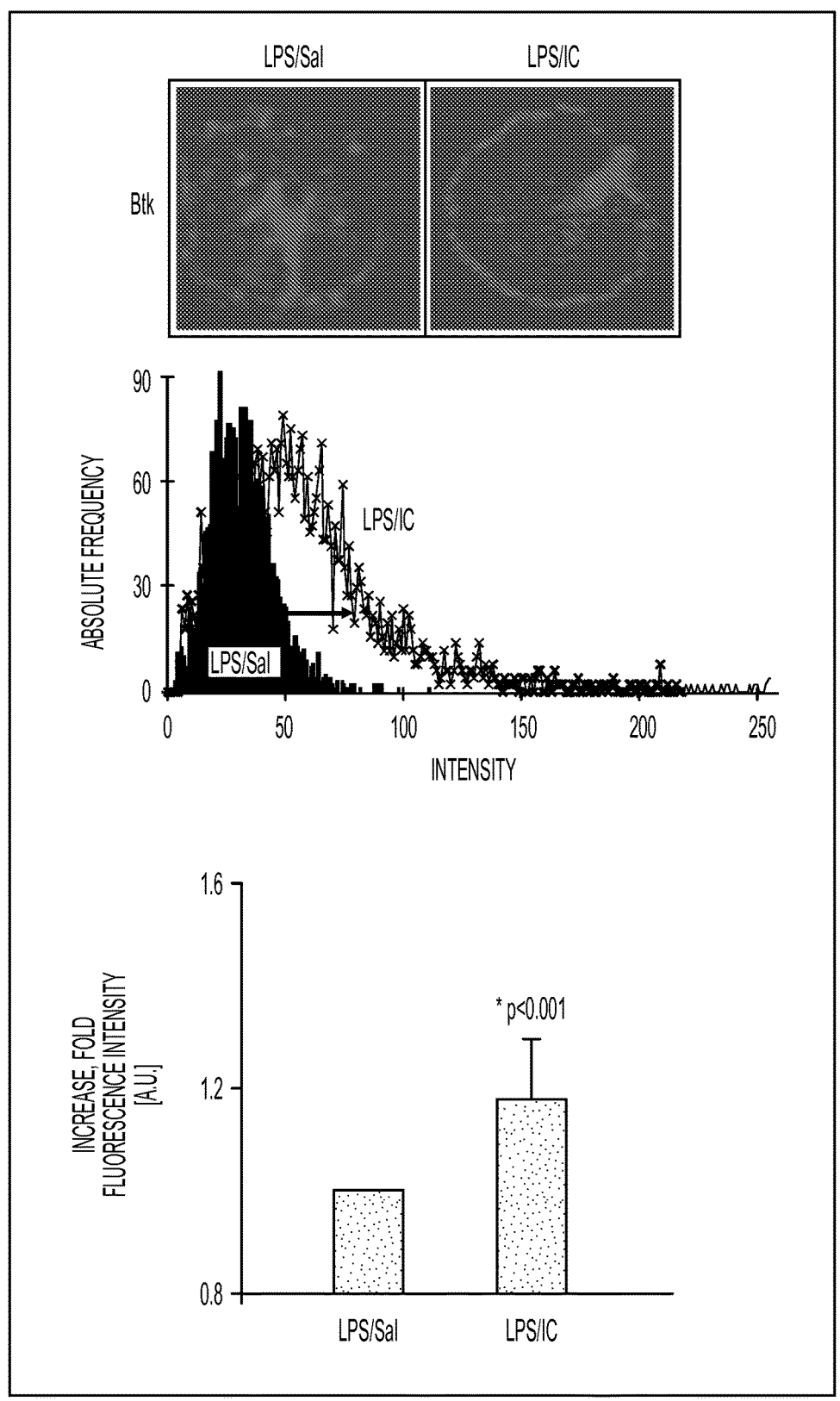
FIGS. 2A-2D: Analysis of expression of Btk (FIG. 2A-1 to 2A-3) and MyD88 (FIG. 2B-1 to 2B-3) in mouse alveolar neutrophils obtained from mice treated with LPS and immune complexes (LPS/IC), and mice treated with LPS and Saline (LPS/Sal). The vertical bar charts in FIGS. 2A-3 and 2B3—depict the fold increase in the levels of Btk and MyD88 in lung neutrophils from LPS/IC mice compared to LPS/Sal mice. F2C to 2C-2: Histogram presenting co-localization between Btk and MyD88 in lung neutrophils of LPS/IC and LPS/Sal mice. The vertical bar chart in FIG. 2C-2 shows correlation factor (Correlation R) indicating the level of co-localization between Btk and MyD88 in lung neutrophils of LPS/IC and LPS/Sal mice.

As shown in FIG. 2A, an increase in the Btk level in neutrophils from mice with LPS/IC ALI (LPS/IC) was observed compared to neutrophils isolated from mice treated with LPS and saline (LPS/Sal group; $p<0.001$). This was in agreement with previous findings that anti-KC:KC immune complexes contribute in a significant way to severe lung inflammation in LPS treated mice (28). Further, Btk was detected in close proximity to the cell membrane in lung neutrophils from the two hit model of ALI (LPS/IC induced ALI), which indicated the activation of this kinase (25, 48, 55).

Figure 2B:
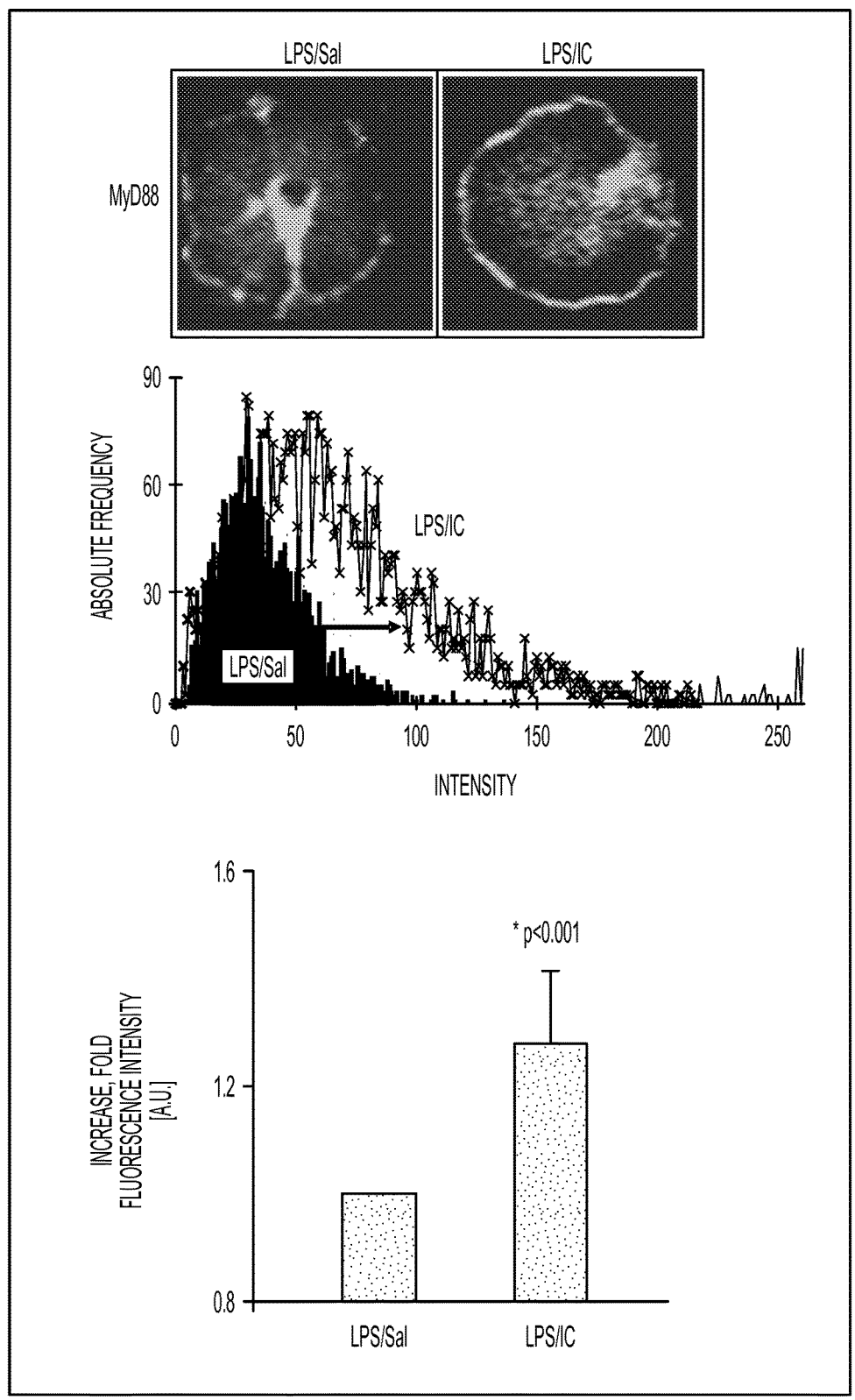
Figure 2C:
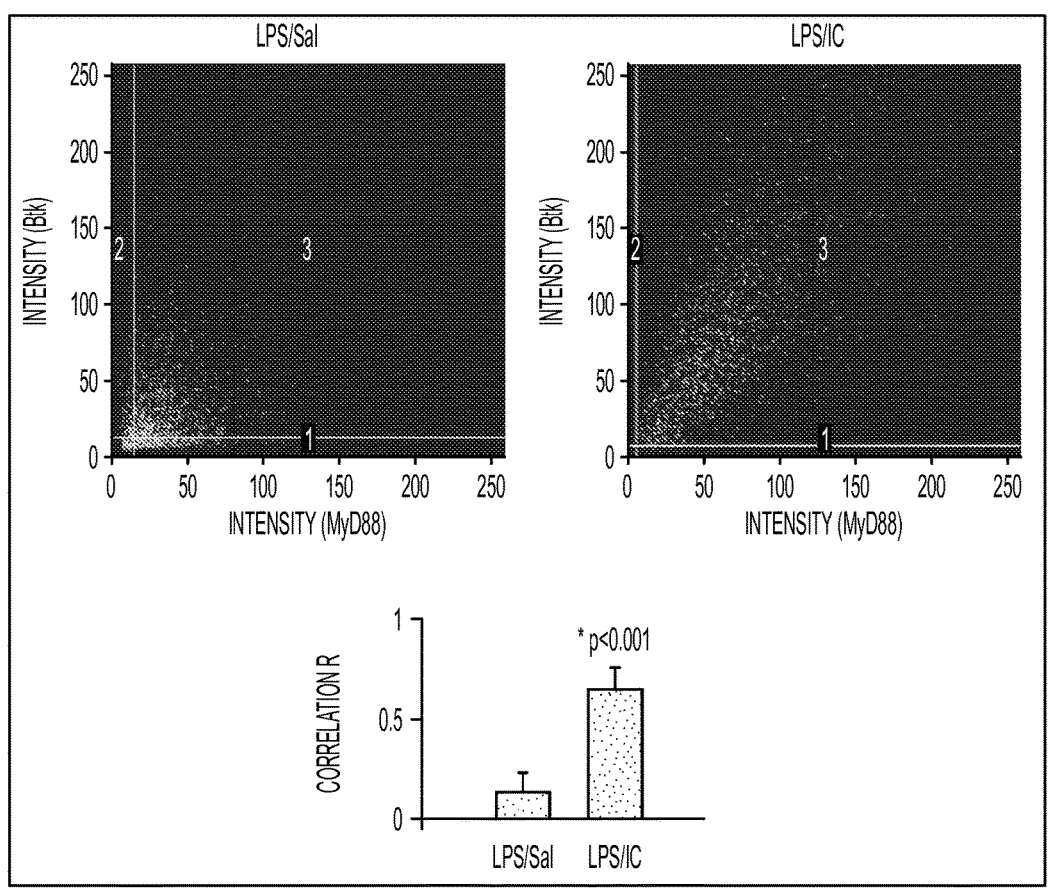
Figure 2D:
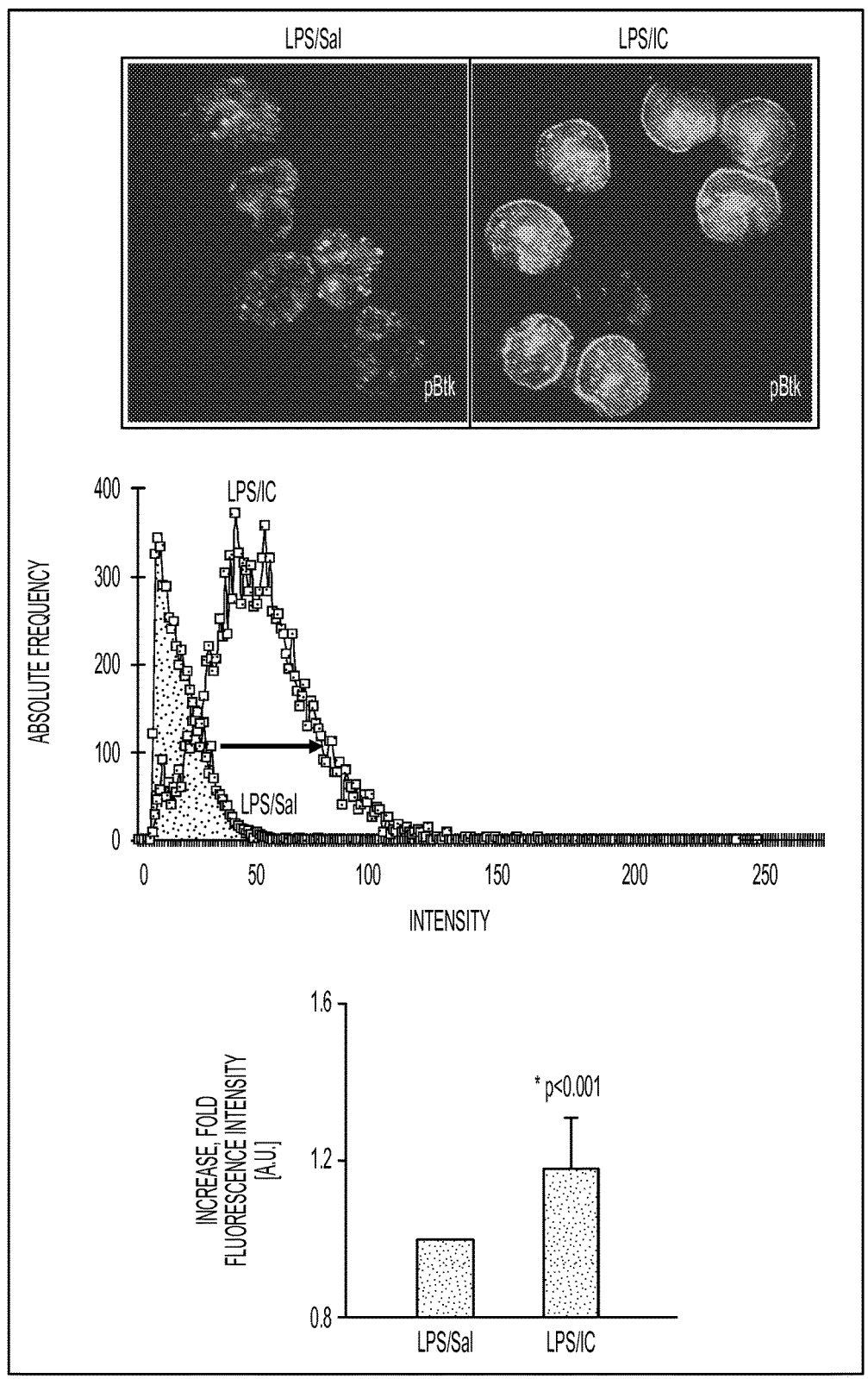

The level of another adaptor molecule associated with the TLR4 cascade, myeloid differentiation factor 88 (MyD88) was also evaluated. According to several reports, including those of the present inventor, Btk may interact with the TLR domains of MyD88 (21, 25). Further, translocation of MyD88 from the cytoplasm to the membrane denotes its activation (2, 25). A significant increase in the level of activated MyD88 was observed in lung neutrophils from mice with LPS/IC ALI (FIG. 2B; $p<0.001$). Moreover, a co-localization between Btk and MyD88 (FIG. 2C) we detected and the correlation factor (Correlation R) was calculated to confirm co-localization between these two molecules in alveolar neutrophils from LPS/IC mice ($p<0.001$). Finally, the amount of phosphorylated Btk (pBtk) was significantly elevated in lung neutrophils from mice with LPS/IC induced ALI (FIG. 2D; $p<0.001$).

EXAMPLE IV

Blocking of Btk Protects Mice from Acute Lung Injury

To study the role of Btk further, Btk in the alveolar compartment was inhibited by administering specific siRNA via intranasal route. Mice received siRNA for Btk after pre-treatment with LPS (8 h) but before anti-KC:KC immune complexes were administered. At this time neutrophils are already present in lungs, and treatment prevented further activation of alveolar neutrophils by immune complexes. This is in agreement with the present inventor's studies in patients with ALI/ARDS where immune complexes contribute to severity of lung inflammation and affect the outcome of ALI/ARDS (3, 14, 26, 27, 29, 30).

Figure 3A:
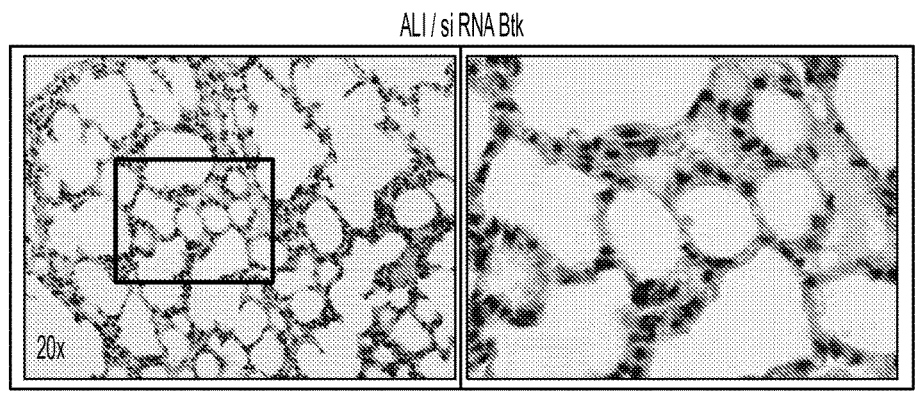
FIG. 3A-3C.
Figure 3B:
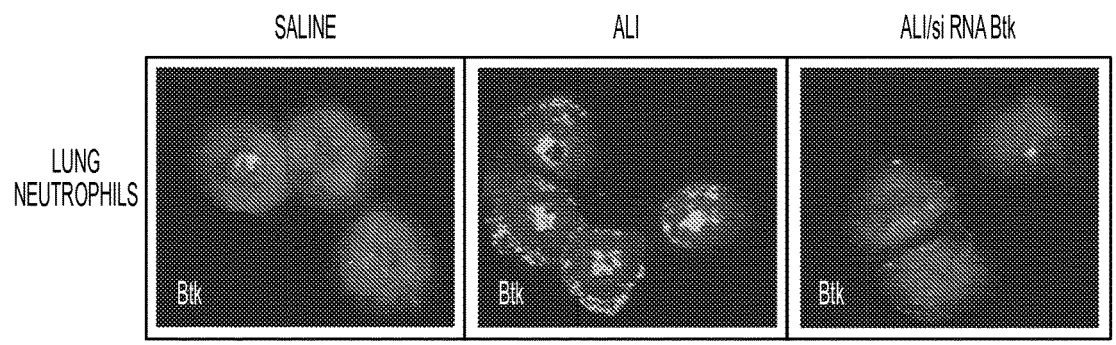
Figure 3C:
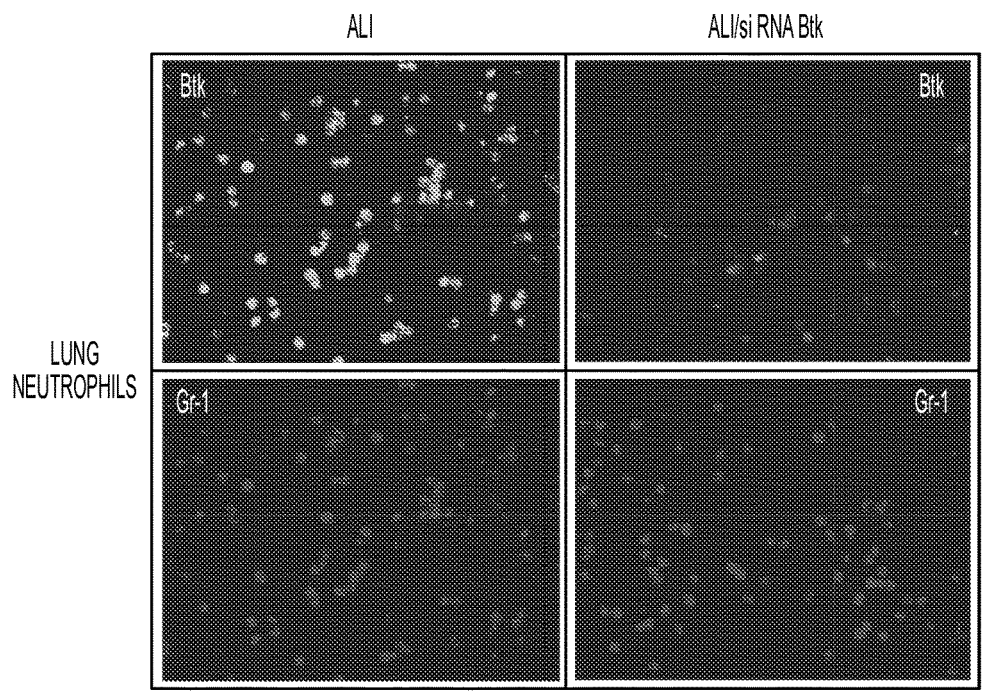

The analysis of lung histopathology showed attenuation of several indices of lung inflammation/injury, including alveolar hemorrhage, interstitial thickening, and presence of alveolar exudates in mice treated with siRNA specific for Btk (FIG. 3A). Analysis of images (Lung Injury Score, LIS) confirmed the protective effect of Btk inhibition, i.e., lessening of lung dysfunction in mice with LPS/IC induced ALI (Table 5). Finally, the effectiveness of blocking the expression of Btk, which substantially down-regulated in alveolar neutrophils from mice that received siRNA for Btk, is presented in FIG. 3B.

Due to the fact that neutrophils play a central role in the pathogenesis of ALI/ARDS a novel methodology of blocking Btk directly in lung neutrophils was introduced. F(ab')$_2$ fragments of anti-neutrophil Ab (Ly6G 1A8) were conjugated to specific siRNA for Btk, and the conjugate was administered via intranasal route to deliver siRNA specifically to alveolar neutrophils.

Figure 4A:
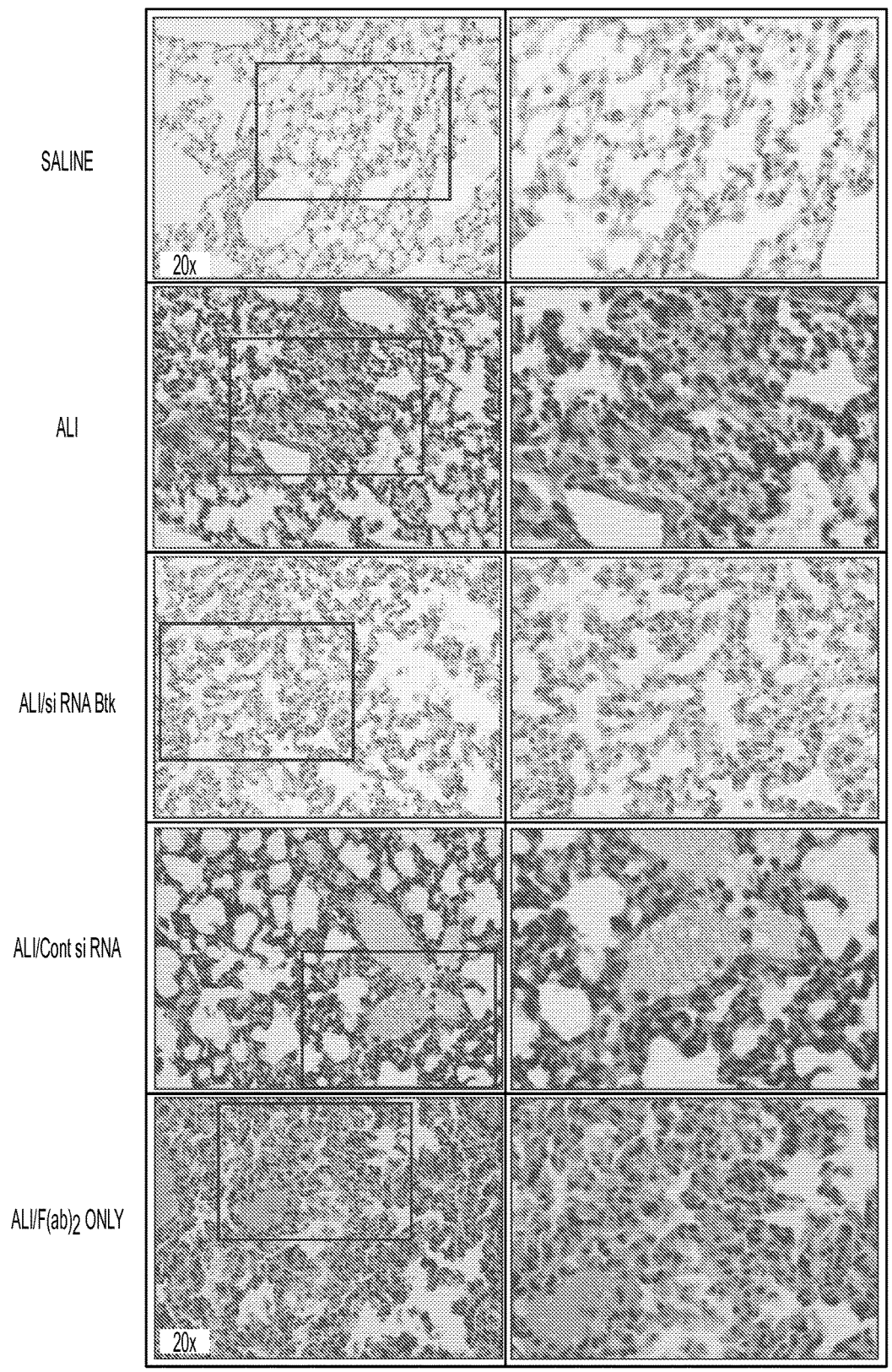
FIGS. 4A-4E.

Treatment with siRNA specific for Btk was protective in this model, since the influx of neutrophils as well as other indices of inflammation were significantly reduced in lungs of animals that received siRNA for Btk (FIG. 4A). This is in contrast to animals that received control siRNA or F(ab')$_2$ fragments alone (FIG. 4A). The analysis of lung histopathology showed a significant decrease in the occurrence of alveolar hemorrhage and interstitial thickening, and diminished presence of alveolar exudates in mice treated with siRNA specific for Btk (FIG. 4A). LIS for all groups of mice is presented in Table 5.

TABLE 5

Lung Injury - Targeting of Btk

| Treatment | Lung Injury Score | | |
|---|---|---|---|
| | Edema fluid | Thickening of alveolar septa | Inflammatory infiltration |
| Saline | 0.129 ± 0.177 | 0.055 ± 0.124 | 0.206 ± 0.034 |
| ALI | 1.468 ± 0.245* | 1.718 ± 0.216* | 1.925 ± 0.083* |
| ALI/siRNA Btk | 0.163 ± 0.090 | 0.055 ± 0.056 | 0.277 ± 0.109 |
| ALI/Cont siRNA | 1.337 ± 0.170** | 1.607 ± 0.276** | 1.824 ± 0.141** |
| ALI/F(ab')$_2$ only | 1.640 ± 0.221 § | 1.742 ± 0.099 § | 1.728 ± 0.071 § |
| ALI/siRNA MMP-9 | 0.069 ± 0.055 | 0.133 ± 0.194 | 0.230 ± 0.171 |

Figure 4B:
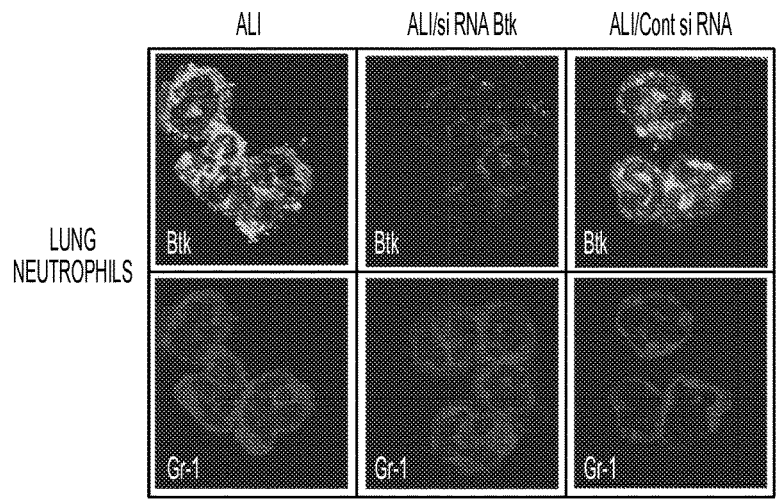
Figure 4C:
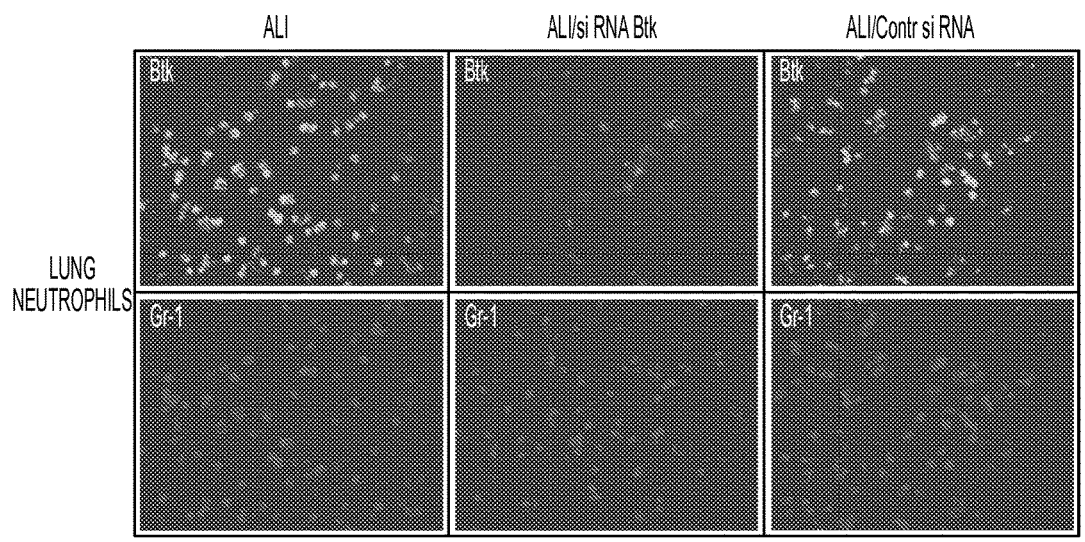
Figure 4D:
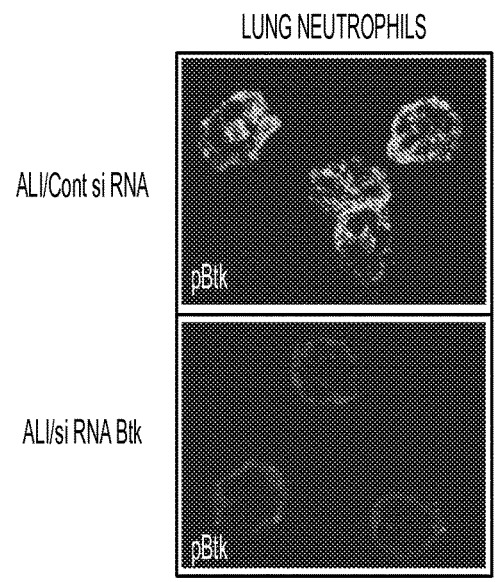
Figure 4E:
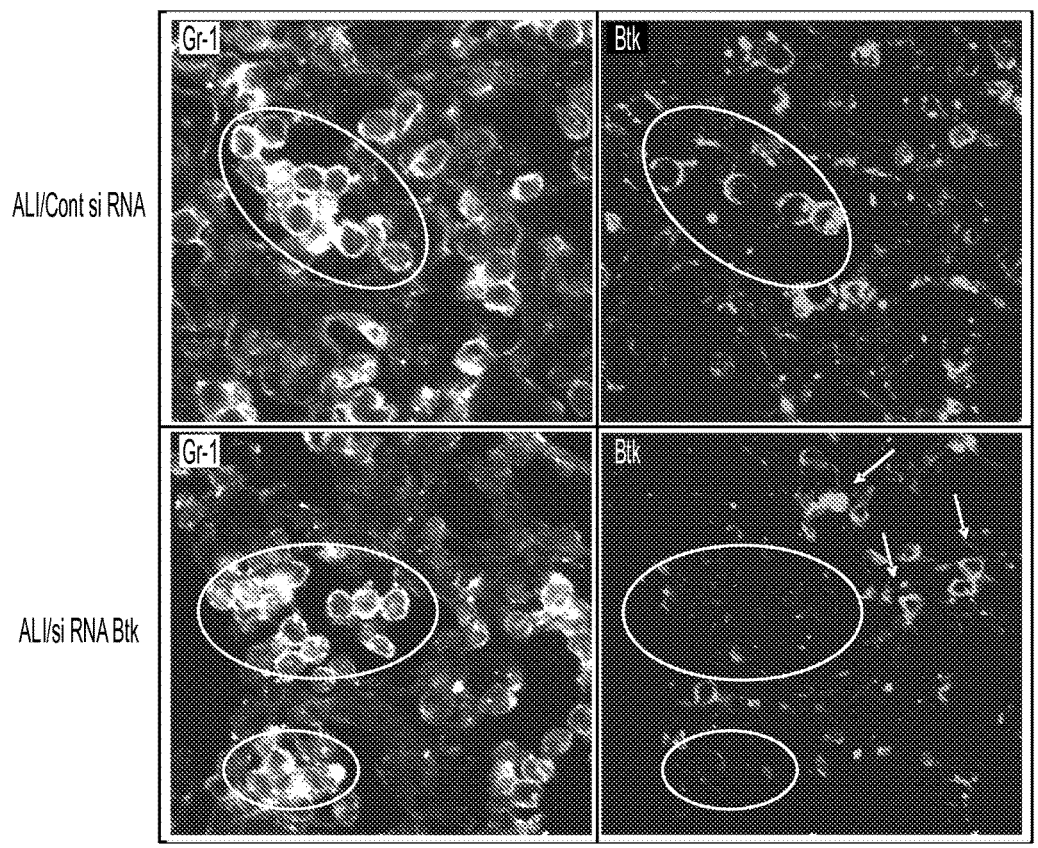

Values are means ± SD.
Analysis was done for 4-5 animals per group.
*$P < 0.001$ compared with Saline; ALI/siRNA Btk; ALI/siRNA MMP-9 groups of mice
**$P < 0.001$ compared with Saline; ALI/siRNA Btk; ALI/siRNA MMP-9 groups of mice
§ $P < 0.001$ compared with Saline; ALI/siRNA Btk; ALI/siRNA MMP-9 groups of mice Laser confocal microscopy was employed to confirm the effectiveness of Btk blocking in alveolar neutrophils. As shown in FIG. 4B there was no detectable Btk in lung neutrophils from mice treated with specific siRNA whereas cells from lungs of mice that received control siRNA or untreated mice with ALI expressed normal levels of this protein (FIG. 4B). The effectiveness of Btk silencing in alveolar neutrophils was 92%. In addition, lack of phosphorylated Btk (pBtk) after treatment with siRNA for Btk is depicted in FIG. 4C. These experiments were performed at 2 h after administration of ICs. Finally, specificity of this approach is shown in FIG. 4D. Expression of Btk was only suppressed in neutrophils but not in other cell types.

EXAMPLE V

Btk Dependent Signaling Pathways Control Neutrophil Survival and Modulate Neutrophil Uptake The two hit model of LPS/IC induced ALI was used to study the role of Btk in mediating neutrophil apoptosis and clearance. Alveolar neutrophils from mice with ALI were evaluated for the presence of active (cleaved) caspase 3. The level of cleaved caspase 3 in lung neutrophils from LPS/IC induced ALI did not differ from that detected in neutrophils from control mice (Saline), indicating that neutrophil apoptosis was down-regulated in this model (FIG. 5A) [p=0.71]. On the other hand, there was more active (cleaved) caspase 3 in cells from mice treated with Btk specific siRNA ($p<0.001$) but not with control siRNA or F(ab')$_2$ fragments alone. The observation that blocking of Btk enhanced apoptosis of lung neutrophils suggesting that Btk controls neutrophil survival in LPS/IC induced ALI. The results presented in FIG. 5A were generated using purified alveolar neutrophils and were standardized according to the cell number.

In other experiments, purified alveolar neutrophils were co-cultured with mouse spleen macrophages for 1 h, and the percentage of phagocytosed neutrophils was assessed by counting numbers of neutrophils present inside macrophages. There was a significant increase in the uptake of apoptotic alveolar neutrophils from mice treated with siRNA specific for Btk compared to cells from mice with LPS/IC induced ALI ($p<0.001$) when the equal numbers of apoptotic neutrophils were analyzed (bars 1 and 2 in FIG. 5B, respectively). Treatment of mice with either control siRNA or F(ab')$_2$ only had no effect on neutrophil phagocytosis (bars 3 and 4 in FIG. 5B, respectively).

In vitro experiments were conducted using mouse bone marrow neutrophils (BMPMNs) to study further the role of Btk in neutrophil apoptosis/clearance. BMPMNs were cultured for 24 h to induce spontaneous apoptosis in the presence or absence of LPS and immune complexes (anti-KC:KC immune complexes). In some experiments, Btk was blocked using siRNA conjugated to F(ab')$_2$ fragments of anti-neutrophil antibodies (Ly-6G1A8). Control siRNA conjugated in the same way served as a control.

Apoptotic BMPMNs were co-cultured with mouse spleen macrophages and the percentage of phagocytosed neutrophils was evaluated by light microscopy (FIG. 5C). As shown in FIG. 5C the presence of LPS and immune complexes delayed clearance of apoptotic neutrophils (FIG. 5C; bar 2 versus bar 1; $p<0.01$). Blocking of Btk after cells become apoptotic triggered the increase in the phagocytic uptake of apoptotic neutrophils (FIG. 5C; bar 3 versus bar 2; $p<0.01$). These observations indicate that Btk has a regulatory role in preparation of apoptotic cells for clearance from areas of inflammation in the lung.

EXAMPLE VI

Btk Controls Lung Neutrophil Function in Mice with LPS/IC Induced Acute Lung Injury Neutrophils are implicated in ALI because of various substances released from granules into the area of inflammation. MMP-9 (gelatinase B) is one of the most extensively studied MMPs in the context of ALI. Moreover, recent observations indicate that MMPs released from neutrophils may have a pathogenic role in ALI (17). The present inventor's previous in vitro study (25) showed the increase in the level of active MMP-9 released by neutrophils as a consequence of cross talk between TLR4 and FcγRIIa. Along these lines, the present findings indicate that Btk mediates MMP-9 production by alveolar neutrophils from mice with LPS/IC induced ALI. Analysis of lung neutrophils (FIGS. 6A and B) showed that cells from mice with LPS/IC ALI that received siRNA specific for Btk do not express MMP-9. In contrast, MMP-9 was detectable inside of neutrophils from ALI mice (ALI group) and from mice treated with control siRNA (ALI/cont siRNA group; FIG. 6B).

In some experiments, siRNA for MMP-9, conjugated to F(ab')$_2$ fragments of anti-neutrophil antibodies (Ly6G1A8), was administered to mice with LPS/IC induced ALI (ALI/siRNA MMP-9 group). Pulmonary histopathology (FIG. 6C) and assessment of LIS showed that inhibiting expression of MMP-9 in alveolar neutrophils leads to attenuation of lung injury in this model of ALI (FIG. 6C and Table 5). In addition, analysis of alveolar neutrophils (FIG. 6B) showed that cells from mice with LPS/IC ALI that received MMP-9 siRNA did not express MMP-9. The effectiveness of MMP-9 silencing in alveolar neutrophils was 91%. Additionally, these findings indicate that there was diminished lung dysfunction in ALI/siRNA MMP-9 group compared to mice with LPS/IC induced ALI (FIG. 6C versus FIG. 1A and FIG. 4A, respectively). This was in contrast to mice that were treated with control siRNA (FIG. 4A). It should be noted that both interventions (siRNA for MMP-9 as well as control siRNA) were part of the same set of experiments.

Endothelial damage in this ALI model was also examined by assessing the release of thrombomodulin (TM), which is a membrane protein expressed on the capillary endothelium (40, 52). A Western Blot analysis of BAL fluid samples was performed (FIG. 6D) from control mice (Saline), mice with LPS/IC induced ALI, and mice treated with siRNA specific for Btk, or MMP-9, or control siRNA. The bar graph in FIG. 6D includes data from 3 experiments. For each repetition a fold over a corresponding control was calculated. Means of all repetitions as well as associated standard deviations were graphed. In addition, statistical analysis has revealed that levels of thrombomodulin (TM) were significantly higher ($p<0.05$) in bronchoalveolar (BAL) fluid from mice with LPS/IC induced ALI compared to mice treated with either siRNA for Btk or siRNA for MMP-9. The same was true for mice that received nonspecific control siRNA ($p<0.05$).

In summary, FIG. 6D shows significantly increased levels of TM released by damaged endothelium in LPS/IC induced ALI and mice treated with control siRNA. In contrast, no TM was detected in the Saline group. Very low levels of TM in BAL fluids from mice that received siRNA for Btk or MMP-9 further support the protective effect of both treatments in mouse ALI (FIG. 6D).

Figure 7A:
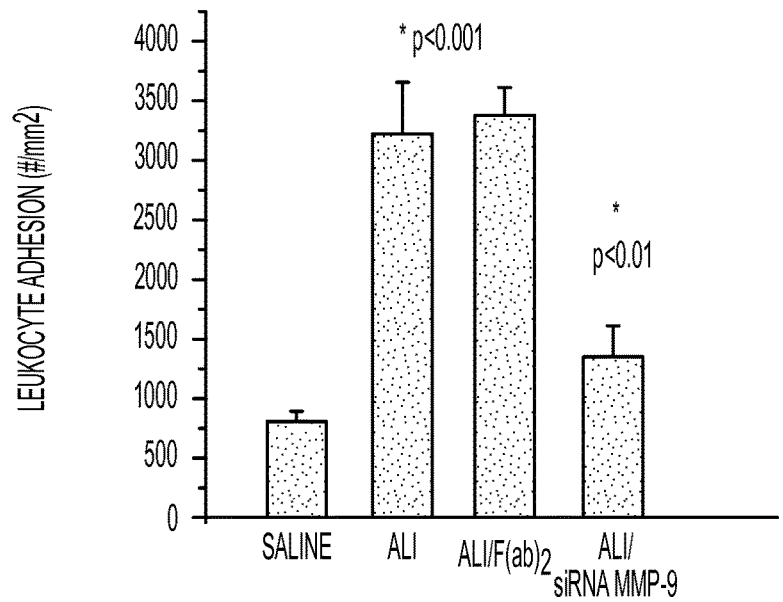
FIGS. 7A-7C are graphs showing adhesion of leukocytes to endothelium (FIG. 7A), leukocyte emigration (FIG. 7B), and wall Shear rate (FIG. 7C). Mice were treated with Saline (Saline), with LPS and anti-KC:KC ICs (ALI), with LPS and Ly6G1A8 F(ab')$_2$ fragments and ICs (ALI/F(ab')$_2$), with LPS and MMP-9 siRNA conjugated to Ly6G1A8 F(ab')$_2$ fragments and ICs (ALI/siRNA MMP-9). Samples were obtained 14 hours after anti-KC:KC IC administration.
Figure 7B:
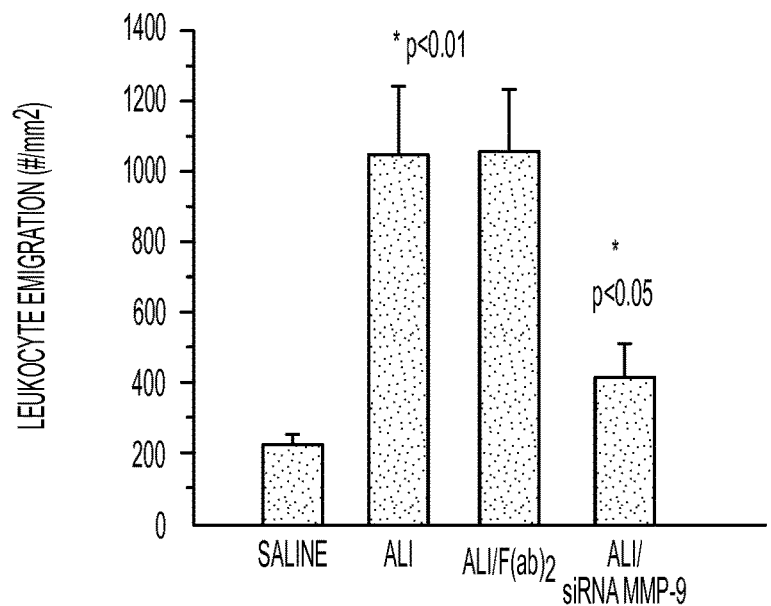

Finally, intravital microscopy was performed to monitor neutrophil adhesion to endothelium in mice with LPS/IC induced ALI. Leukocyte adhesion was significantly increased ($p<0.001$) in mice with LPS/IC induced acute lung injury (ALI group) when compared to control mice (Saline group) [FIG. 7A]. Emigration of leukocytes in LPS/IC treated mice (ALI group) was elevated approximately 5-times in comparison to control mice (Saline group; FIG. 7B; $p<0.01$). Administering F(ab')$_2$ fragments of anti-neutrophil antibodies to LPS/IC treated mice neither altered adhesion of leukocytes to endothelium nor emigration of these cells (FIGS. 7A and B). In contrast, animals that were treated with LPS and received siRNA for MMP-9 conjugated to F(ab')$_2$ fragments of anti-neutrophil antibodies prior to administration of anti-KC:KC immune complexes (ALI/ siRNA MMP-9 group) showed a significant decrease in leukocyte adhesion and emigration (p<0.01 and p<0.05 respectively).

Figure 7C:
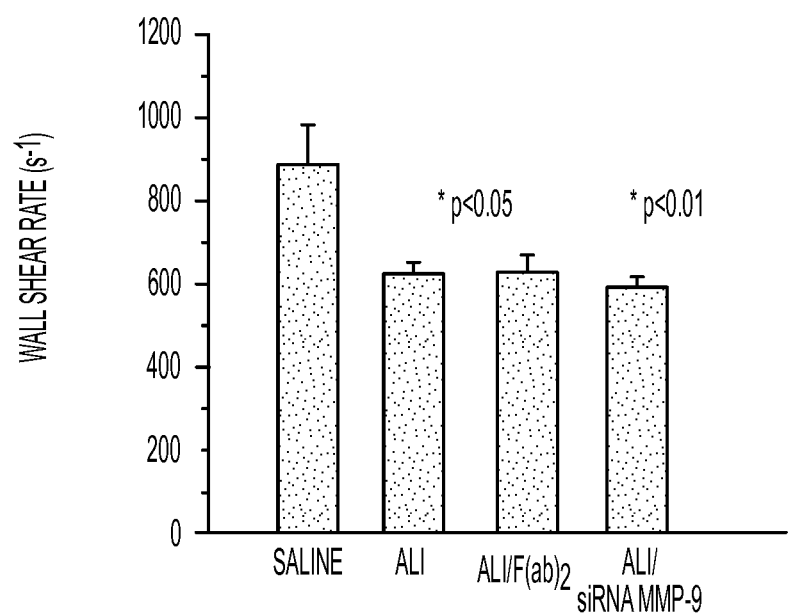
Figure 7D:
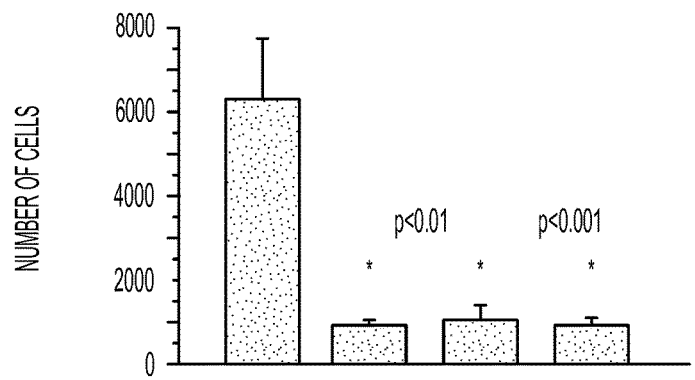
Figure 7E:
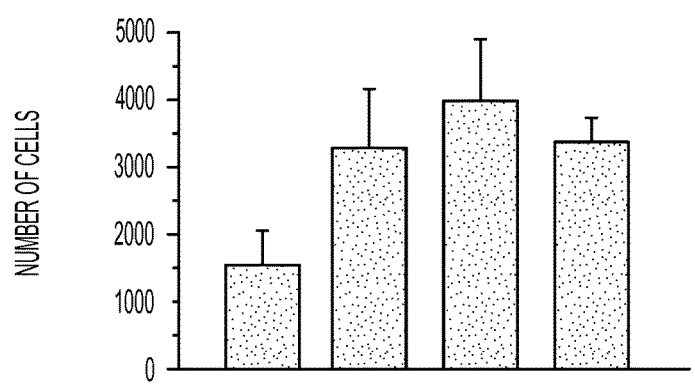
Figure 7F:
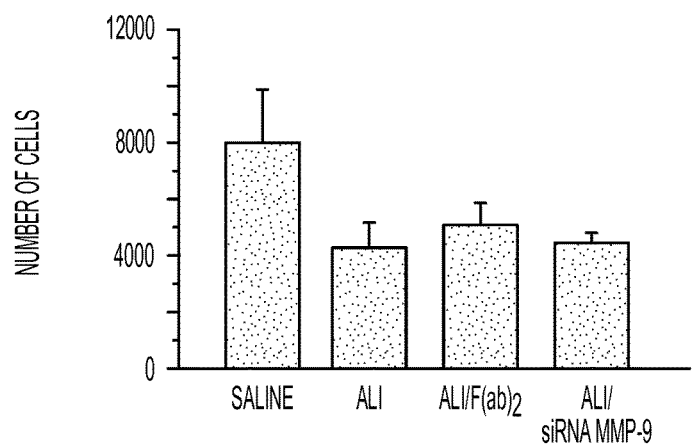

Although the Wall Shear Rate (WSR) was significantly lower in the LPS/IC groups (FIG. 7C), venules with WSRs above 500 s$^{-1}$ were chosen to minimize any non-specific effect of this on leukocyte adhesion (47). In addition, the protection observed in the ALI/siRNA MMP-9 group was not related to a recovery of normal WSR, suggesting this was not a major factor in the observed responses, but rather that the siRNA had anti-inflammatory properties. Circulating neutrophil counts were increased 2-fold, and lymphocyte counts were significantly reduced in all ALI groups, suggesting that the siRNA was not acting by preserving normal leukocyte counts (FIG. 7D).

EXAMPLE VI

KC:Anti-KC Complexes are Equivalent to Clinical Immune Complexes

The present inventors furthermore established that anti-KC:KC complexes are the mouse equivalent of clinical immune complexes purified from the pulmonary edema fluids of patients with ALI/ARDS, i.e., human anti-IL-8:IL-8 immune complexes. In functional assays (myeloperoxidase release: MPO; FIG. 8A) and superoxide release; pp40phox (45); FIG. 8B), it was confirmed that mouse bone marrow neutrophils respond to mouse anti-KC:KC ICs in a similar manner to human neutrophils responding to clinical anti-IL-8:IL-8 ICs (ICEF) (13, 26, 27). Further, ICEF were purified from pulmonary edema fluids from patients with ALI/ARDS and human neutrophils used for these experiments from blood of these patients.

EXAMPLE VII

Figure 10A:
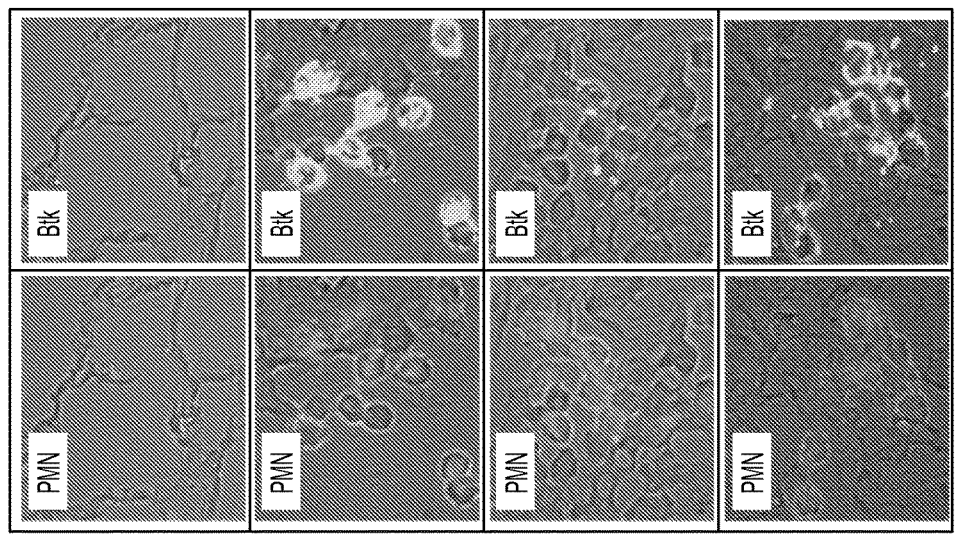
FIGS. 10A-10C.

Btk as Treatment Target in Mice with Influenza A Virus-induced Acute Lung Injury Critically ill patients infected with influenza viruses frequently require hospitalization and develop ALI/ARDS. Inflammatory responses triggered by the infection may contribute to the accumulation of excessive numbers of neutrophils in lungs, and ultimately may promote lung tissue damage and progression to ALI/ARDS (T. Narasaraju et al., *Am. J. Pathol.* 179:199-210, 2011). Histopathological changes that are characteristic of ALI/ARDS include alveolar hemorrhage, interstitial thickening, and the presence of alveolar exudate. We have observed such characteristics as well as evidence of increased infiltration of inflammatory cells when analyzing lung tissue sections from mice with flu induced ALI (second panels from the top in FIG. 10A). Lung tissues from control/uninfected animals are also shown in FIG. 10A/1A (top panels). The presence of lung dysfunction in animals with influenza virus triggered ALI was confirmed by analysis of LIS (Table 6). LIS is based on a histological scale from "0" (no changes) to "2" (significant changes).

TABLE 6

Lung Injury in Flu-Infected Animals: Btk Targeting

| | Lung Injury Score (LIS) in Treatment Groups | | |
|---|---|---|---|
| Lung changes | Flu | Flu/siRNA Btk | Flu/control siRNA |
| Inflammatory infiltration | 1.52 ± 0.21 | 0.89 ± 0.35* | 1.48 ± 0.14* |
| Thickening of alveolar septa | 1.67 ± 0.14 | 0.79 ± 0.42* | 1.72 ± 0.12* |
| Edema fluid | 1.44 ± 0.37 | 0.73 ± 0.26* | 1.29 ± 0.30* |

Values are means ± SD of 5-9 animals per group.
*p < 0.05 compared to Flu and control siRNA
LIS Criteria:
0 - No changes
1 - Moderate changes
2 - Significant changes Btk Activation is Increased in Alveolar Neutrophils of Mice with Flu-Induced ALI.

Figure 10B:
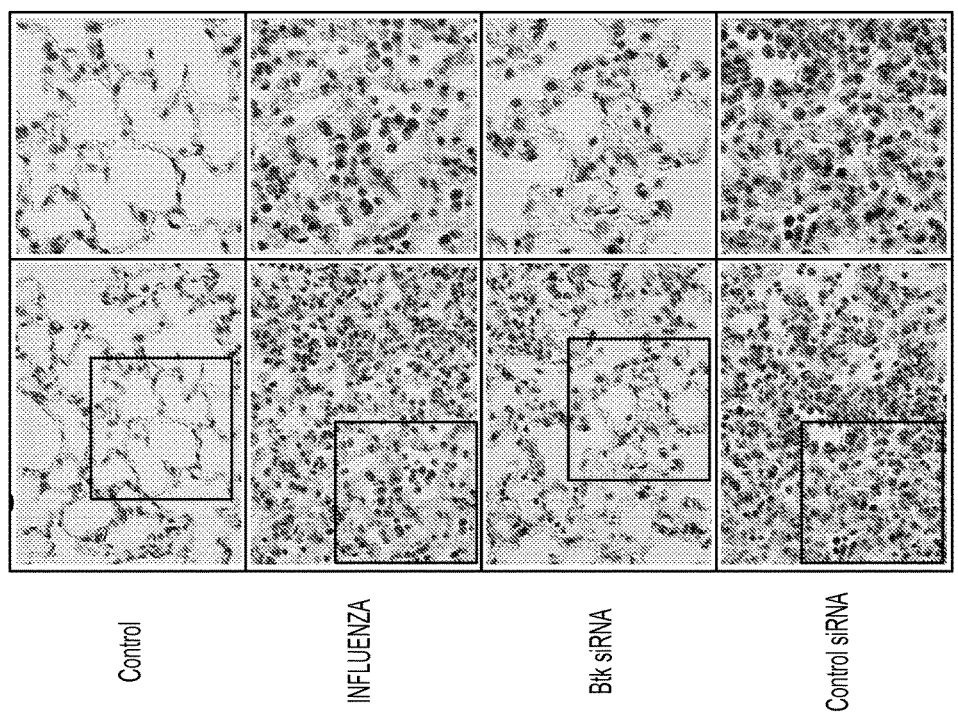
Figure 10C:
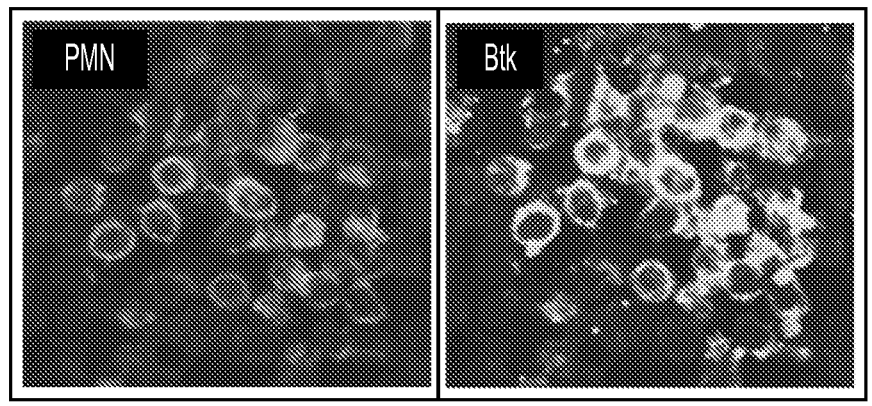

A substantial increase in Btk activation (membrane localization) was observed in pulmonary neutrophils (PMN) in lungs of infected animals (FIG. 10C). Upon activation Btk was recruited to the plasma membrane (FIGS. 10C and 10B). Neutrophils from lungs of mice with ALI are shown in second panels from the top in FIG. 10B whereas the top panels of this figure depict tissues from uninfected/control mice.

Blocking of Btk in Alveolar Neutrophils Protects Mice from Flu Induced ALI

Because neutrophils play a central role in the pathogenesis of ALI/ARDS, the method of the present invention was introduced to block Btk directly in lung neutrophils: siRNA specific for Btk was conjugated to F(ab')$_2$ fragments of the anti-neutrophil mAb Ly6G 1A8, and the conjugate administered i.n. to deliver the siRNA specifically to Btk-expressing alveolar neutrophils to silence Btk selectively in such cells. As depicted in FIG. 10A (second panels from bottom) such treatment with siRNA specific for Btk was protective; the influx of neutrophils as well as other indices of inflammation were significantly reduced in lungs of animals that received Btk-specific siRNA.

Analysis of lung histopathology showed a significant decrease in the occurrence of alveolar hemorrhage and interstitial thickening, and diminished presence of alveolar exudates in mice treated with Btk-specific siRNA (FIG. 10A). In contrast, administration of control siRNA had a negligible effect (bottom panels in FIG. 10A).

Figure 11A:
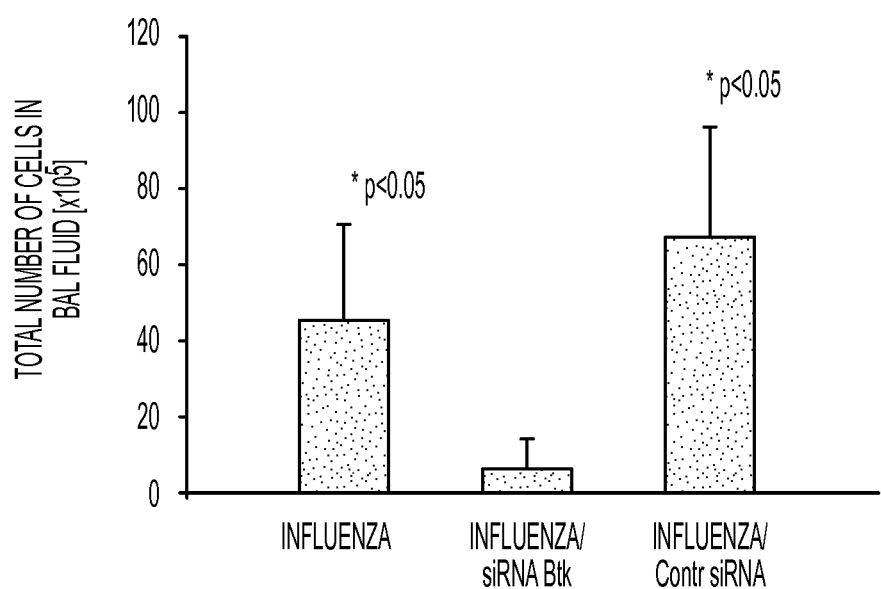
FIGS. 11A-11C. Total cell numbers (FIG. 11A), and concentrations of neutrophils (FIG. 11B) and erythrocytes (FIG. 11C) in BAL fluid from mice with Flu virus-induced ALI (Influenza), mice with ALI treated with Btk siRNA conjugated to Ly6G1A8 F(ab')$_2$ fragments (Influenza/siRNA Btk) and mice with ALI that received control siRNA conjugated to Ly6G1A8 F(ab')$_2$ fragments (Influenza/Contr siRNA). 5-10 animals per group; typical findings are presented.
Figure 11B:
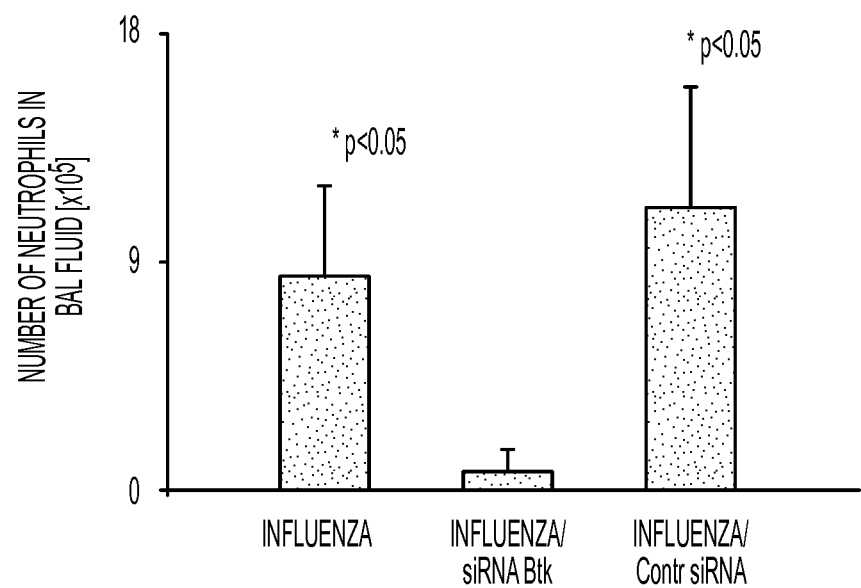
Figure 11C:
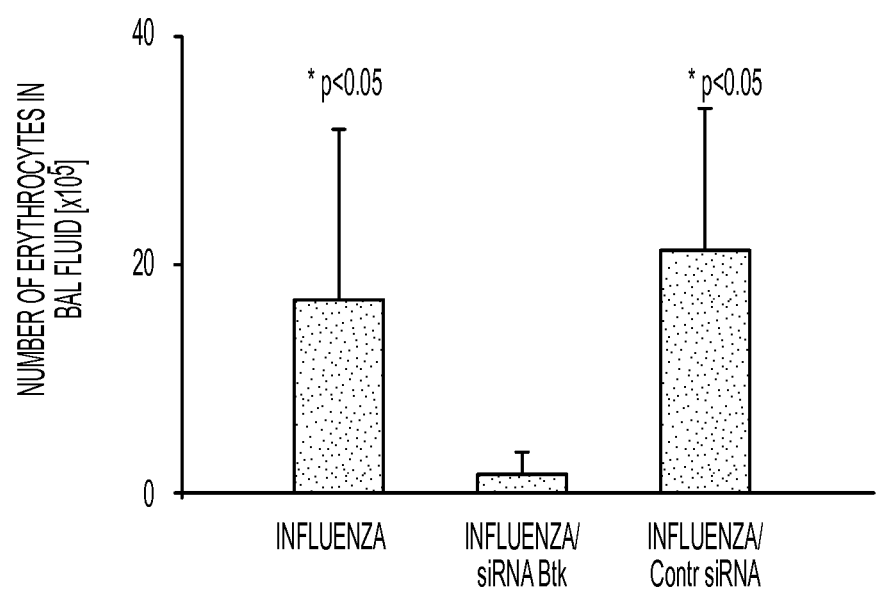

Effectiveness of Btk inhibition in neutrophils (PMN) is presented in FIG. 10B (Btk specific siRNA [second panels from the bottom] vs. control siRNA [bottom panels in FIG. 10B]). Table 7 shows LIS (lung injury score) for mice that received Btk specific siRNA and control siRNA. The total cell number as well as the levels of neutrophils and red blood cells (RBCs) in BAL fluids for these two groups of mice are depicted in FIGS. 11A, 11B and 11C, respectively. Moreover, it should be stressed that the therapeutic effects disclosed herein were cell specific, i.e., targeting specifically alveolar neutrophils.

Figure 12:
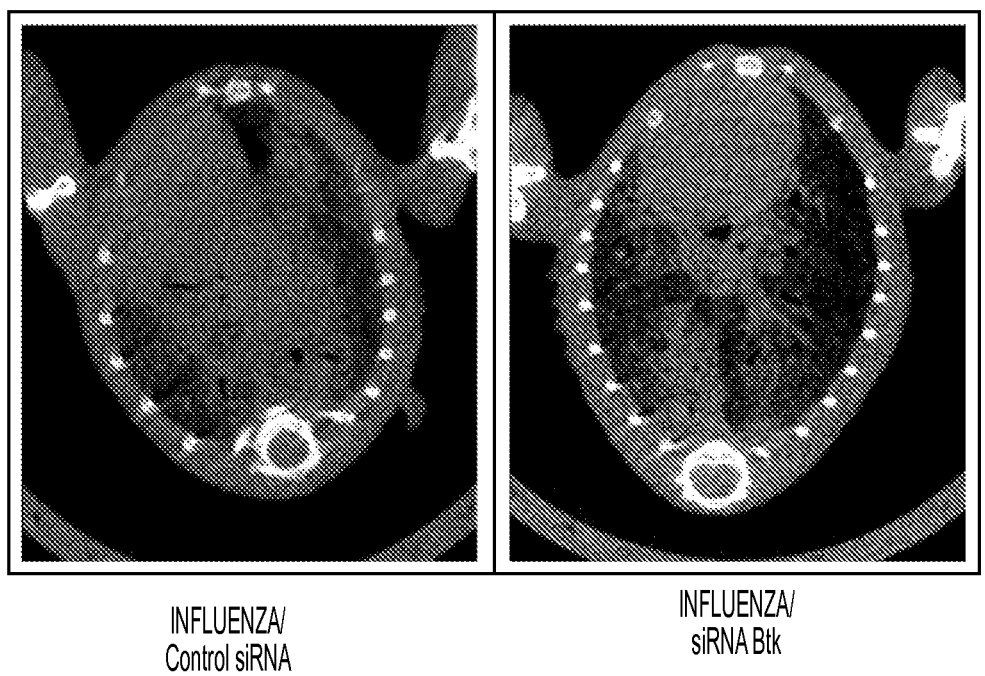
FIG. 12. Computed tomographic scan (CT Scan) of mice with ALI that received control siRNA conjugated to Ly6G1A8 F(ab')$_2$ fragments (Influenza/Control siRNA) and mice with ALI treated with Btk siRNA conjugated to Ly6G1A8 F(ab')$_2$ fragments (Influenza/siRNA Btk). 5 animals per group; typical findings are presented.

In addition, the presence of lung dysfunction in these animals was confirmed using Computed Tomography (CT). Analysis of images obtained using CT confirmed the protective effect of Btk inhibition, i.e., lessening of lung dysfunction in mice with flu induced ALI (FIG. 12).

Figure 13:
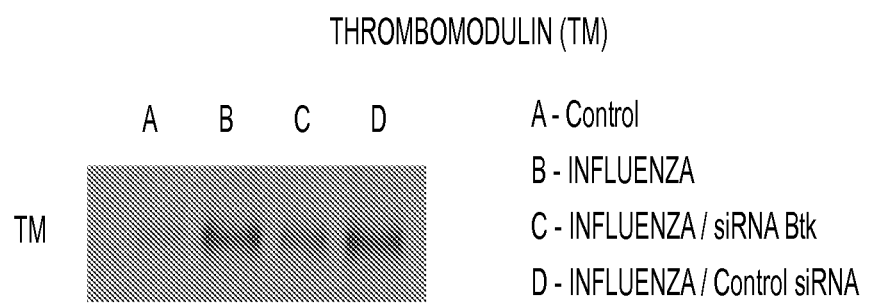
FIG. 13. Levels of Thrombomodulin (TM) in BAL fluid from control mice (Control), mice with Flu virus-induced ALI (Influenza), mice with ALI treated with Btk siRNA conjugated to Ly6G1A8 F(ab')$_2$ fragments (Influenza/siRNA Btk) and mice with ALI that received control siRNA conjugated to Ly6G1A8 F(ab')$_2$ fragments (Influenza/Control siRNA). Typical results from 3 experiments are presented.

Moreover, the high amount of thrombomodulin™ in the BAL fluid is an indication of endothelial damage. TM is a membrane protein expressed on the capillary endothelium (40, 52) A Western Blot analysis of BAL fluid samples (FIG. 13) from control mice (Control), mice with flu induced ALI, and mice treated with siRNA specific for Btk, or control siRNA. FIG. 13 showed significantly increased levels of TM released by damaged endothelium in flu induced ALI and mice treated with control siRNA. In contrast, virtually no TM in the Control group was detected. Very low levels of TM in BAL fluids from mice that received siRNA for Btk further support the protective effect of this treatment in mouse ALI (FIG. 13).

Figure 14:
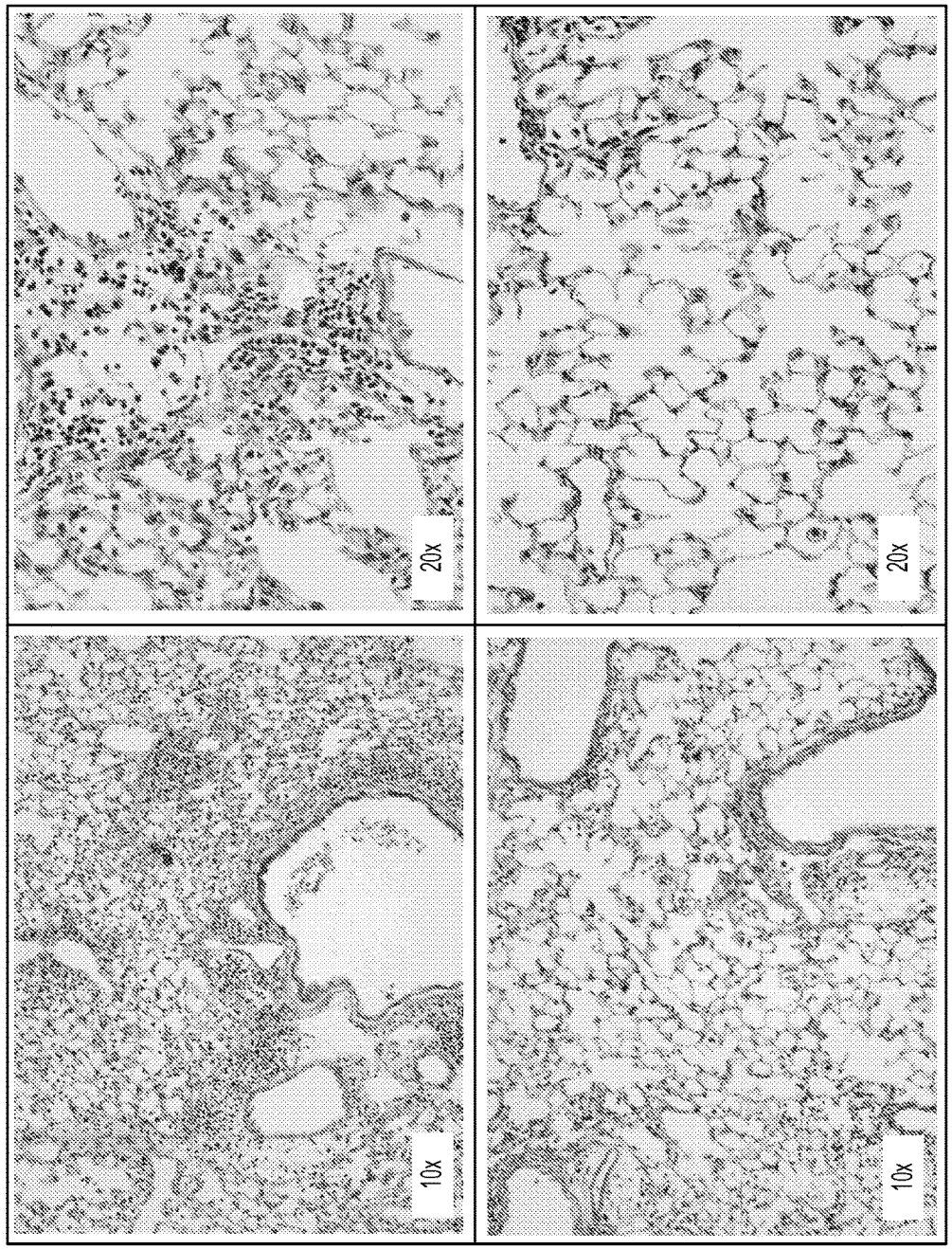
FIG. 14. H&E staining of lung sections of mice with Flu virus-induced ALI (Influenza) and mice with ALI treated with Btk inhibitor ibrutinib/PCI-32765 (Pharmacyclics) (Influenza/Btk inhibitor). Five animals per group; typical findings are presented.

Finally, administration of specific Btk inhibitor had a similar protective effect as siRNA for Btk (FIG. 14 and Table 7).

TABLE 7

Protection from Lung Injury by Btk Targeting

| Lung changes | Lung Injury (LIS) with Treatment | |
|---|---|---|
| | Flu | Flu + Btk Inhibitor |
| Inflammatory infiltration | 1.38 ± 0.20 | 0.79 ± 0.08* |
| Thickening of alveolar septa | 1.37 ± 0.15 | 0.60 ± 0.25* |
| Edema fluid | 1.52 ± 0.16 | 0.59 ± 0.28* |

Values are means ± SD.
Analysis was done for 5 animals per group.
*p < 0.001
LIS Criteria:
0 - No changes
1 - Moderate changes
2 - Significant changes

EXAMPLE VIII

Btk as Treatment Target in Mice with Lung Injury of COPD/Emphysema

Figure 15:
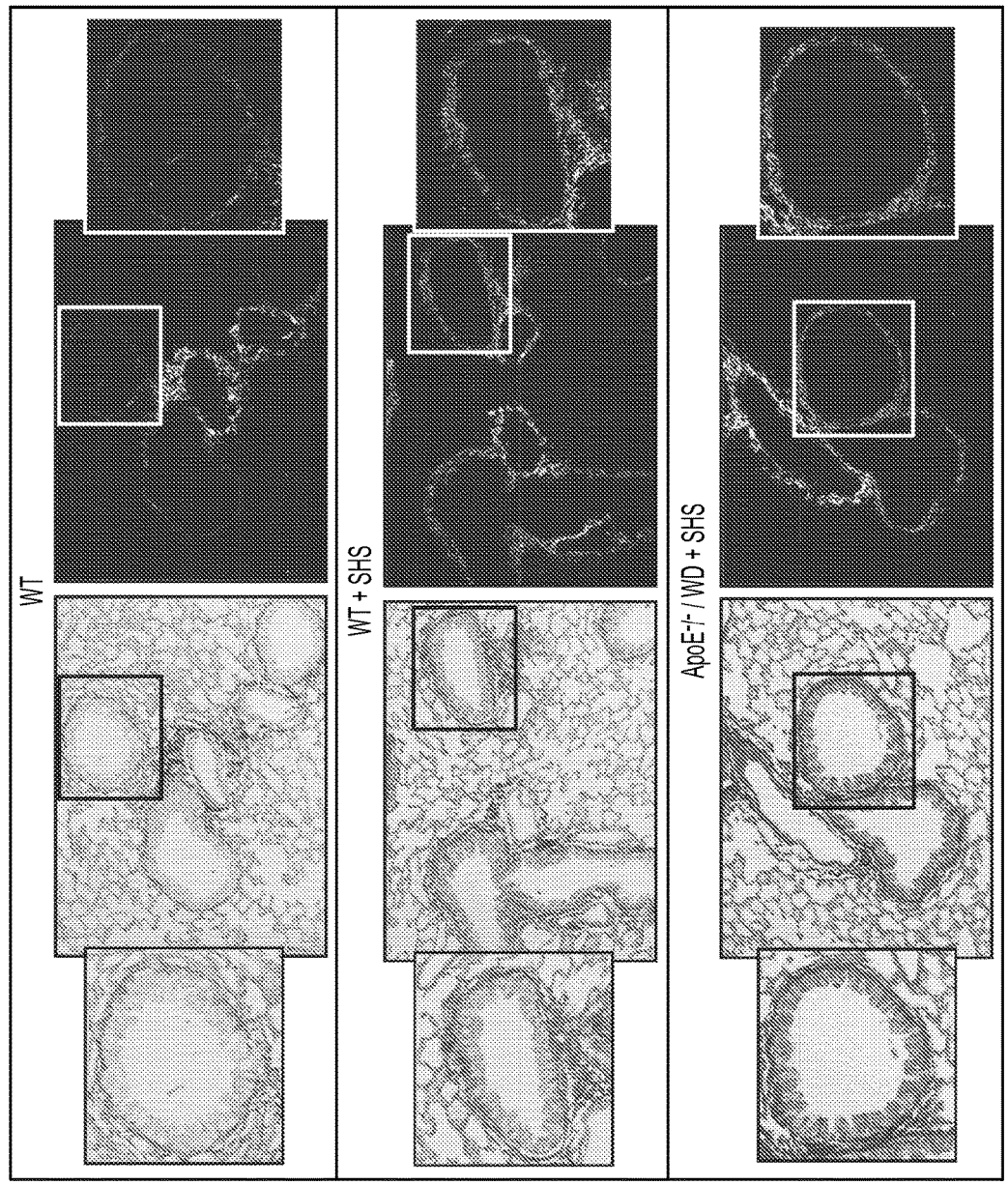
FIGS. 15A-15C shows results of PicroSirius Red staining (for collagen) of lung sections of WT animals (WT) (FIG. 15A), WT animals exposed to SHS (WT+SHS) (FIG. 15B) and ApoE$^{-/-}$ mice fed Western Diet (WD) and exposed to SHS (ApoE$^{-/-}$/WD+SHS) (FIG. 15C) analyzed using white light (images on left) and polarized light (images on right). 3-5 animals per group; typical findings are presented.

PicroSirius Red stained lung sections were examined under plane polarized light to visualize collagen content of the airway walls. In FIG. 15 it can be seen that not only is the layer of airway collagen larger in smoking (SHS) animals (WT and ApoE$^{-/-}$; shown in the middle and bottom images of FIG. 15, respectively), but that a greater proportion of the collagen is made up of thick fibers vs. those seen in non-smoking animals (WT; top images in FIG. 15). Deposition of thick collagen fibers around airways in smoke exposed animals is a suspected source of increased airway stiffness and associated airway resistance (WD=Western Diet).

Figure 16:
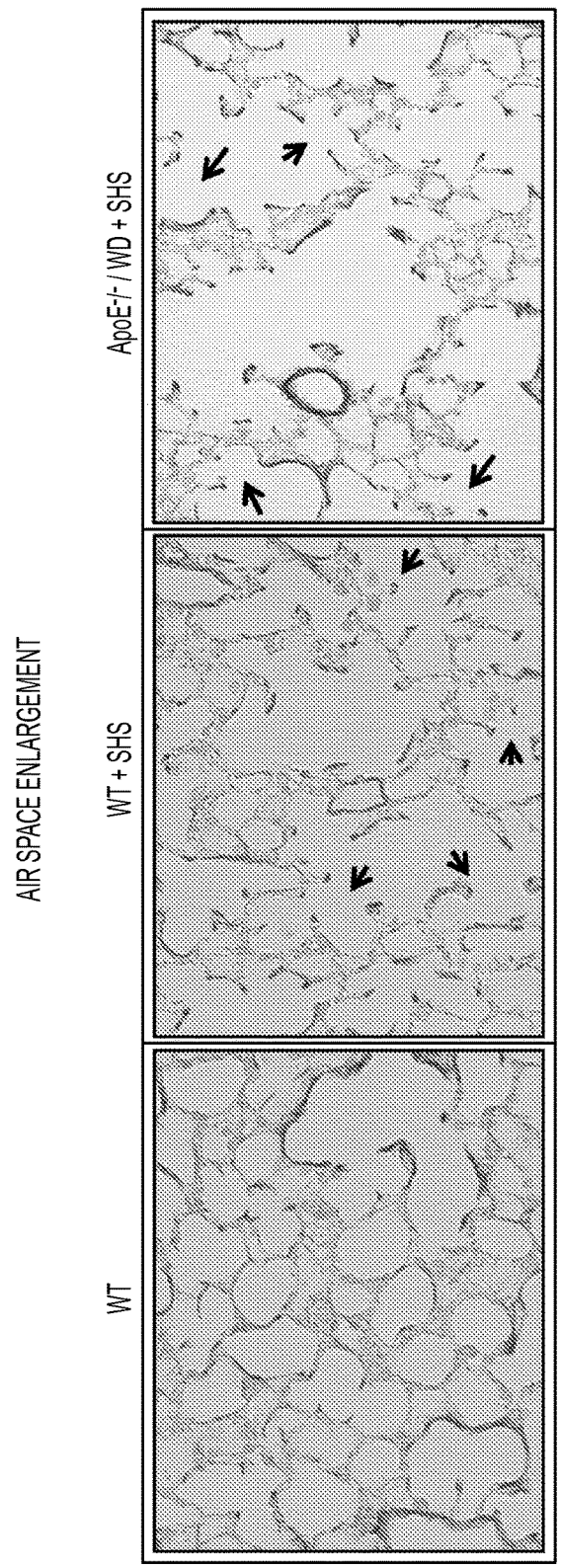
FIG. 16 shows results of Hart's Elastin stained lung sections of WT animals (WT), WT animals exposed to SHS (WT/SHS) and ApoE$^{-/-}$ mice fed Western Diet (WD) and exposed to SHS (ApoE$^{-/-}$/WD+SHS). 3 animals per group; typical findings presented.

Hart's Elastin stain was used to visualize airspace elastin, to detect strand breaks in alveolar walls (FIG. 16). In non-smoking controls (WT; left image) elastin appears as thin continuous strands which outline alveolar walls. In smoke-(SHS) exposed animals (WT and ApoE$^{-/-}$; middle and right images in FIG. 16, respectively) alveolar destruction/air space enlargement is visible as a loss of round, intact alveoli, and alveolar destruction is further visualized/confirmed by the appearance of thick elastin nodules. These nodules result from recoil of severed elastin strands upon loss of tension due to breaks in alveolar walls.

Figure 17:
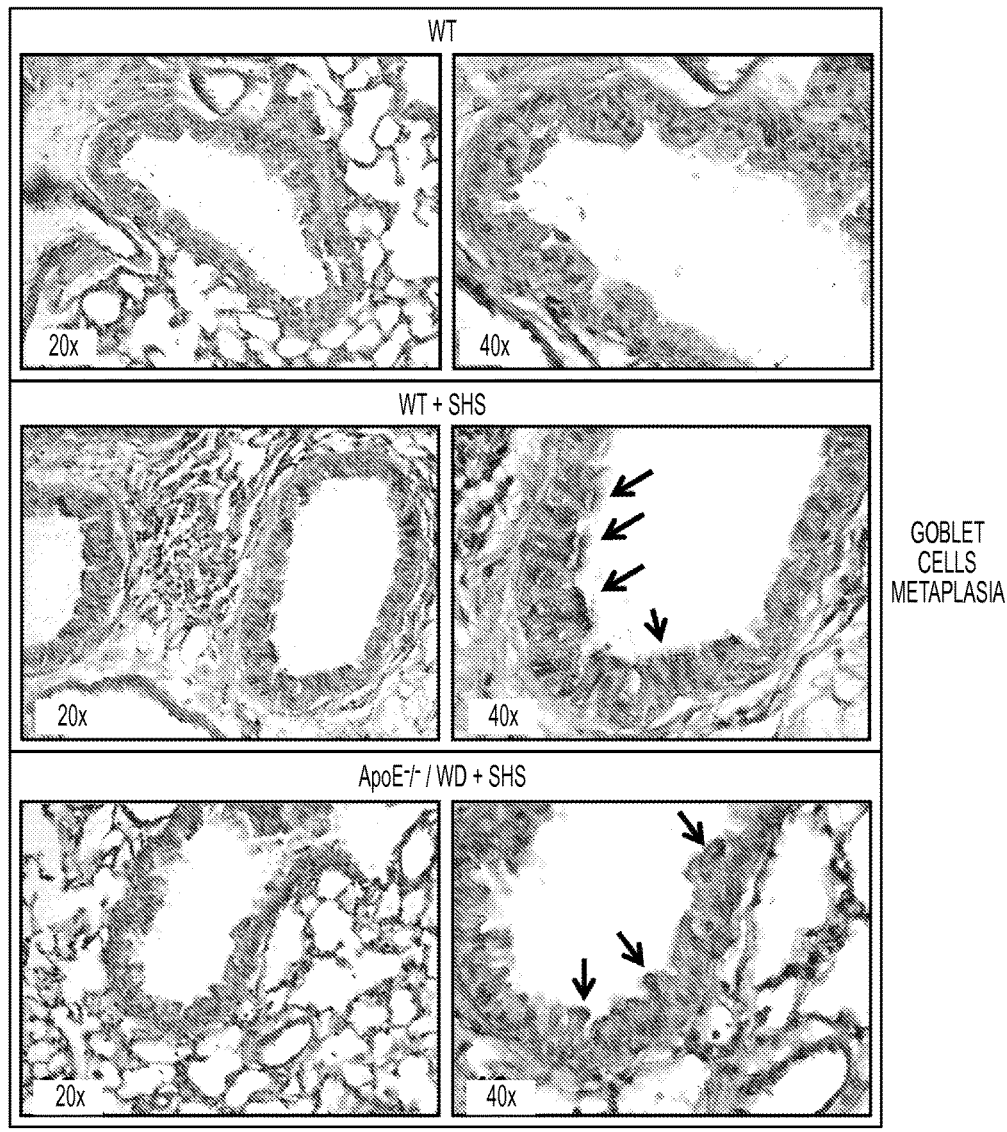
FIGS. 17A-17C shows the presence of Goblet Cell Metaplasia (GCM) in three groups of mice. Control WT animals (WT) (FIG. 17A), WT animals exposed to SHS (WT+SHS) (FIG. 17B) and ApoE$^{-/-}$ mice fed Western Diet (WD) and exposed to SHS (ApoE$^{-/-}$/WD+SHS) (FIG. 17C). 3-4 animals per group; typical findings are presented.

COPD is characterized by an excessive production of mucus (chronic bronchitis) and impaired mucociliary clearance both of which contribute to airway obstruction in patients with this condition (Pappas et al., supra). There are very few goblet cells present in the bronchi/bronchioles of healthy mice (WT; top images in FIG. 17). The appearance of clusters of goblet cells in the bronchi/bronchioles of smoke exposed mice is considered acceptable evidence of Goblet Cell Metaplasia (GCM). Examples of GCM are presented in FIG. 17 (WT and ApoE$^{-/-}$ mice; middle and bottom images in FIG. 17, respectively). Along with other factors, GCM is a component of small airway remodeling in patients with COPD.

Figure 18:
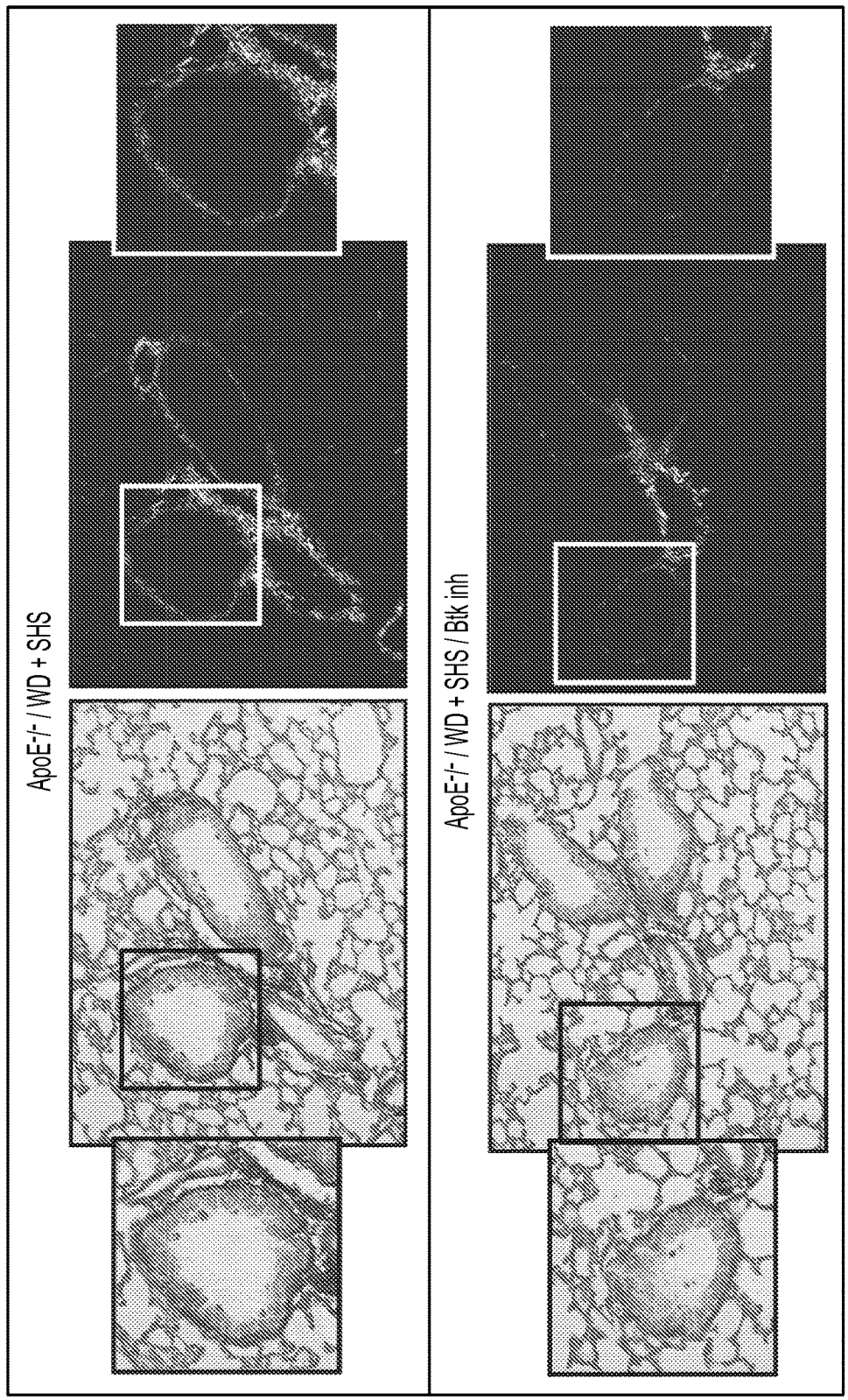
FIGS. 18A-18B show results of PicroSirius Red staining (for collagen) in lung sections of ApoE$^{-/-}$ mice fed Western Diet and exposed to SHS (ApoE$^{-/-}$/WD+SHS) (FIG. 18A) and ApoE$^{-/-}$ mice fed Western Diet, exposed to SHS and treated with Btk inhibitor (ApoE$^{-/-}$/WD+SHS/Btk inh) (FIG. 18B). Sections were analyzed using white light (images on left) and polarized light (images on right). 6-9 animals per group; typical findings are presented.
Figure 19:
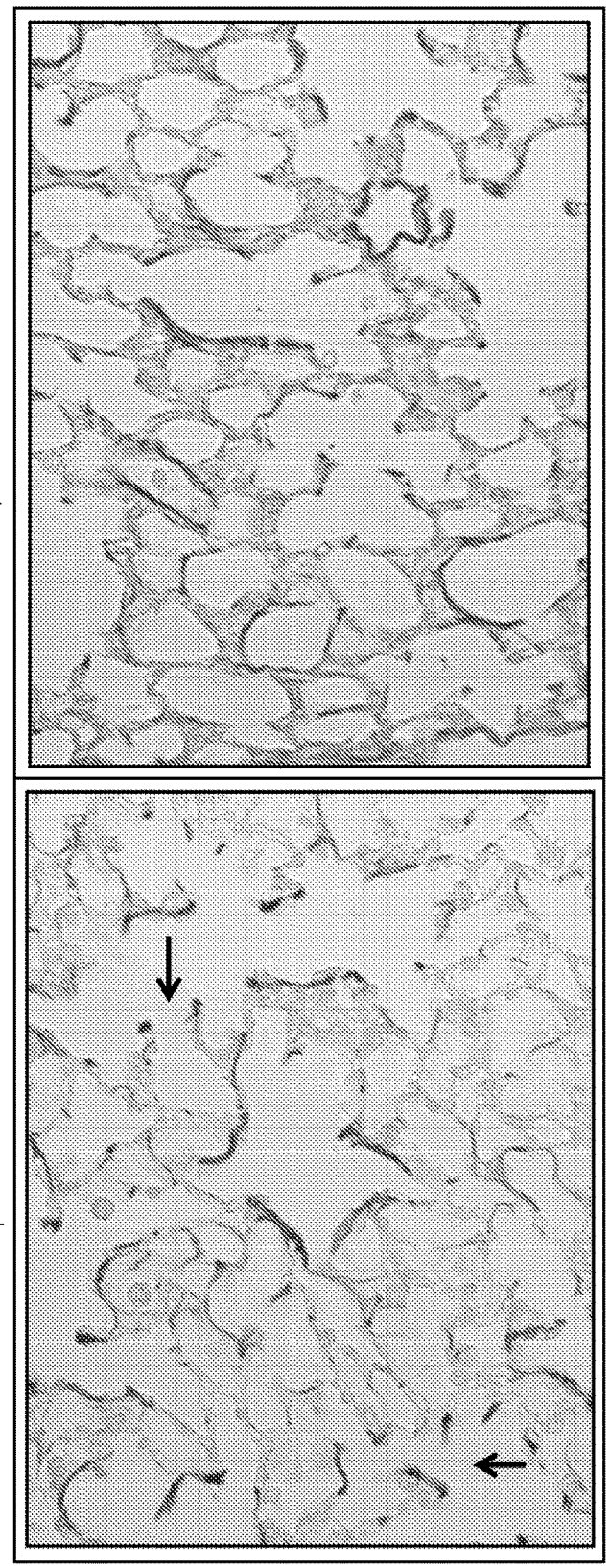
FIG. 19. Hart's Elastin stained lung sections of ApoE$^{-/-}$ mice fed Western Diet (WD) and exposed to SHS (ApoE$^{-/-}$/WD+SHS) and ApoE$^{-/-}$ mice fed Western Diet (WD), exposed to SHS and treated with Btk inhibitor ibrutinib/PCI-32765 (Pharmacyclics) (ApoE$^{-/-}$/WD+SHS/Btk inh). 4 animals per group; typical findings are presented.

Finally, inhibiting Btk with a selective small molecule pharmacological inhibitor (PCI-32765) had a dramatic protective effect on symptoms of emphysema/COPD (ApoE$^{-/-}$ mice) as shown in FIG. 18; bottom images and FIG. 19; right image. Thus it was concluded that inhibition of Btk is useful for treatment of emphysema/COPD.

REFERENCES CITED BY NUMBER

In Addition to Those Cited Fully in the Body of the Text

1. Abraham E, Carmody A, Shenkar R, Arcaroli J. Neutrophils as early immunologic effectors in hemorrhage or endotoxemia-induced acute lung injury. *Am. J. Physiol. Lung Cell. Mol. Physiol.* 279:1137-1145, 2000.
2. Akira S, Takeda K. Toll-like receptor signaling. *Nat. Rev. Immunol.* 4:499-511, 2004.
3. Allen T C, Fudala R, Nash S, Kurdowska A. Anti-interleukin-8 autoantibody:interleukin-8 immune complexes visualized by laser confocal microscopy in injured lung. Co-localization with FcγRIIa in lung tissues from patients with acute respiratory distress syndrome. *Arch. Pathol. Lab. Med.* 131:452-456, 2007.
4. Azoulay E, Darmon M, Delclaux C, Fieux F, Bornstain C, Moreau D, Attalah H, Le Gall J R, Schlemmer B. Deterioration of previous acute lung injury during neutropenia recovery. *Crit. Care Med.* 30:781-786, 2002.
5. Baumann U., Schmidt R. E., Gessner J. E. New insights into the pathophysiology and in vivo function of IgG Fc receptors through gene deletion studies. *Arch. Immunol. Ther. Exp.* 51:399-406, 2003.
6. Bozic C R, Kolakowski L F, Gerard N P, Garcia-Rodriguez C, von Uexkull-Guldenband C, Conklyn M J, Breslow R, Showell H J, Gerard C. Expression and biologic characterization of the murine chemokine KC. *J. Immunol.* 154:6048-6057, 1995.
7. Desiderio S. Role of Btk in B cell development and signaling. *Curr. Opin. Immunol.* 9:534-540, 1997.
8. Donnelly S, Roake W, Brown S, Young P, Naik H, Wordsworth P, Isenberg D A, Reid K B, Eggleton P. Impaired recognition of apoptotic neutrophils by the C1q/calreticulin and CD91 pathway in systemic lupus erythematosus. *Arthritis Rheum.* 54:1543-1556, 2006.
9. Duffin R, Leitch A E, Fox S, Haslett C, Rossi A G. Targeting granulocyte apoptosis: mechanisms, models, and therapies. *Immunol. Rev.* 236:28-40, 2010.
10. Fiedler K, Sindrilaru A, Terszowski G, Kokai E, Feyerabend T B, Bullinger L, Rodewald H R, Brunner C. Neutrophil development and function critically depend on Bruton tyrosine kinase in a mouse model of X-linked agammaglobulinemia. *Blood* 117:1329-1339, 2011.
11. Flick M R, Perel A, Staub N C. Leukocytes are required for increased lung microvascular permeability after microembolization in sheep. *Circ. Res.* 48:344-351, 1981.
12. Fligiel S E, Standiford T, Fligiel H M, Tashkin D, Strieter R M, Warner R L, Johnson K J, Varani J. Matrix metalloproteinases and matrix metalloproteinase inhibitors in acute lung injury. *Hum. Pathol.* 37:422-30.2006.

13. Fudala R, Krupa A, Matthay M A, Allen T C, Kurdowska A K. Anti-IL-8 autoantibody:IL-8 immune complexes suppress spontaneous apoptosis of neutrophils. *Am. J. Physiol. Lung Cell. Mol. Physiol.* 293:L364-L374, 2007.
14. Fudala R, Krupa A, Stankowska D, Allen T C, Kurdowska A K. Does activation of the FcgammaRIIa play a role in the pathogenesis of the acute lung injury/acute respiratory distress syndrome? *Clin. Sci. (Lond).* 118:519-26, 2010.
15. Gao H., Neff T., Ward P. A. Regulation of lung inflammation in the model of IgG immune-complex injury. *Annu. Rev. Pathol. Mech. Dis.* 1:215-242, 2006.
16. Gilbert C, Levasseur S, Desaulniers P, Dusseault A A, Thibault N, Bourgoin S G, Naccache P H. Chemotactic factor-induced recruitment and activation of Tec family kinases in human neutrophils. II. Effects of LFM-A13, a specific Btk inhibitor. *J. Immunol.* 170:5235-5243, 2003.
17. Gonzalez-López A, Albaiceta G M. Repair after acute lung injury: molecular mechanisms and therapeutic opportunities. *Crit. Care.* 16:209 doi: 10.1186/cc11224, 2012.
18. Grommes J, Soehnlein O. Contribution of neutrophils to acute lung injury. *Mol. Med.* 17:293-307, 2011.
19. Heflin A C Jr, Brigham K L. Prevention by granulocyte depletion of increased vascular permeability of sheep lung following endotoxemia. *J. Clin. Invest.* 68:1253-1260, 1981.
20. Honda F, Kano H, Kanegane H, Nonoyama S, Kim E S, Lee S K, Takagi M, Mizutani S, Mono T. The kinase Btk negatively regulates the production of reactive oxygen species and stimulation-induced apoptosis in human neutrophils. *Nat. Immunol.* 13:369-78, 2012.
21. Jefferies C A, Doyle S, Brunner C, Dunne A, Brint E, Wietek C, Walch E, Wirth T O, Neill L A. Bruton's tyrosine kinase is a Toll/interleukin-1 receptor domain-binding protein that participates in nuclear factor kappaB activation by Toll-like receptor 4. *J. Biol. Chem.* 278: 26258-26264, 2003.
22. Kawakami Y, Kitaura J, Hata D, Yao L, Kawakami T. Functions of Bruton's tyrosine kinase in mast and B cells. *J. Leukoc. Biol.* 65:286-290, 1999.
23. Kennedy A D, DeLeo F R. Neutrophil apoptosis and the resolution of infection. *Immunol. Res.* 43:25-61, 2009.
24. Kim J H, Suk M H, Yoon D W, Lee S H, Hur G Y, Jung K H, Jeong H C, Lee S Y, Lee S Y, Suh I B, Shin C, Shim J J, In K H, Yoo S H, Kang K H. Inhibition of matrix metalloproteinase-9 prevents neutrophilic inflammation in ventilator-induced lung injury. *Am. J. Physiol. Lung Cell. Mol. Physiol.* 291:L580-587, 2006.
25. Krupa A, Fudala R, Florence J M, Tucker T, Allen T C, Standiford T J, Luchowski R, Fol M, Rahman M, Gryczynski Z, Gryczynski I, Kurdowska A K. Bruton's Tyrosine Kinase mediates FcγRIIa/Toll-Like Receptor-4 receptor crosstalk in human neutrophils. *Am. J. Respir. Cell. Mol. Biol.* 48:240-249, 2013.
26. Krupa A, Fudala R, Stankowska D, Loyd T, Matthay M, Allen T C, et al. Anti-chemokine autoantibody:chemokine immune complexes activate endothelial cells via IgG receptors. *Am. J. Respir. Cell. Mol. Biol.* 41:155-169, 2009.
27. Krupa A, Kato H, Matthay M A, Kurdowska A. Proinflammatory activity of anti-IL-8 autoantibody:IL-8 complexes in alveolar edema fluid from patients with acute lung injury. *Am. J. Physiol. Lung Cell. Mol. Physiol.* 286:L1105-L1113, 2004.
28. Krupa A, Walencka M J, Shrivastava V, Loyd T, Fudala R, Frevert C W, Martin T R, Kurdowska A K. Anti-KC autoantibody:KC complexes cause severe lung inflammation in mice via IgG receptors. *Am. J. Respir. Cell. Mol. Biol.* 37:532-543, 2007.
29. Kurdowska A, Noble J M, Grant I S, Robertson R, Haslett C, Donnelly S C. Anti-interleukin-8 autoantibodies in patients at risk for the acute respiratory distress syndrome. *Crit. Care Med.* 30:2335-2337, 2002.
30. Kurdowska A, Noble J M, Steinberg K P, Ruzinski J, Hudson L D, Martin T R. Anti-interleukin-8 autoantibody: interleukin-8 complexes in the acute respiratory distress syndrome. Relationship between the complexes and clinical disease activity. *Am. J. Respir. Crit. Care Med.* 163: 463-468, 2001.
31. Looney M R, Su X, Van Ziffle J A, Lowell C A, Matthay M A. Neutrophils and their Fcgamma receptors are essential in a mouse model of transfusion-related acute lung injury. *J. Clin. Invest.* 116:1615-1623, 2006.
32. Martin T R, Pistorese B P, Hudson L D, Maunder R J. Function of lung and blood neutrophils in patients with the adult respiratory distress syndrome. Implications for the pathogenesis of lung infections. *Am. Rev. Respir. Dis.* 144:254-262, 1991.
33. Martin T R, Nakamura M, Matute-Bello G. The role of apoptosis in acute lung injury. *Crit. Care Med.* 31:S184-S188, 2003.
34. Matthay M A, Ware L B, Zimmerman G A. The acute respiratory distress syndrome. *J. Clin. Invest.* 122:2731-2740, 2012.
35. Matute-Bello G, Liles W C, Radella F 2nd, Steinberg K P, Ruzinski J T, Hudson L D, Martin T R. Modulation of neutrophil apoptosis by granulocyte colony-stimulating factor and granulocyte/macrophage colony-stimulating factor during the course of acute respiratory distress syndrome. *Crit. Care Med.* 28:1-7, 2000.
36. Matute-Bello G, Liles W C, Radella II F, Steinberg K P, Ruzinski J T, Jonas M, Chi E Y, Hudson L D. Neutrophil apoptosis in the acute respiratory distress syndrome. *Am. J. Respir. Crit. Care Med.* 156:1969-1977, 1997.
37. Michiels A, Tuyaerts S, Bonehill A, Corthals J, Breckpot K, Heirman C, Van Meirvenne S, Dullaers M, Allard S, Brasseur F, van der Bruggen P, Thielemans K. Electroporation of immature and mature dendritic cells: implications for dendritic cell-based vaccines. *Gene Ther.* 12:772-782, 2005.
38. Mohamed A J, Yu L, Bäckesjö C M, Vargas L, Faryal R, Aints A, Christensson B, Berglöf A, Vihinen M, Nore B F, Smith C I. Bruton's tyrosine kinase (Btk): function, regulation, and transformation with special emphasis on the PH domain. *Immunol. Rev.* 228:58-73, 2009.
39. Mueller H, Stadtmann A, Van Aken H, Hirsch E, Wang D, Ley K, Zarbock A. Tyrosine kinase Btk regulates E-selectin-mediated integrin activation and neutrophil recruitment by controlling phospholipase C (PLC) gamma 2 and PI3K gamma pathways. *Blood* 115:3118-3127, 2010.
40. Narasaraju T, Yang E, Samy R P, Ng H H, Poh W P, Liew A A, Phoon M C, van Rooijen N, Chow V T. Excessive neutrophils and neutrophil extracellular traps contribute to acute lung injury of influenza pneumonitis. *Am. J. Pathol.* 179:199-210, 2011.
41. Nimmerjahn F., Ravetch J. V. Fcγ receptors as regulators of immune responses. *Nature* 8:34-47, 2008.
42. Ognibene F P, Martin S E, Parker M M, Schlesinger T, Roach P, Burch C, Shelhamer J H, Parrillo J E. Adult respiratory distress syndrome in patients with severe neutropenia. *N. Engl. J. Med.* 315:547-551, 1986.

43. Park Y J, Liu G, Lorne E F, Zhao X, Wang J, Tsuruta Y, Zmijewski J, Abraham E. PAI-1 inhibits neutrophil efferocytosis. *Proc. Natl. Acad. Sci. USA* 105:11784-11789, 2008.
44. Park Y J, Liu G, Tsuruta Y, Lorne E, Abraham E. Participation of the urokinase receptor in neutrophil efferocytosis. *Blood* 114:860-870, 2009.
45. Quinn M T, Gauss K A. Structure and regulation of the neutrophil respiratory burst oxidase: comparison with nonphagocyte oxidases. *J. Leukoc. Biol.* 76:760-781, 2004.
46. Ravichandran K S. Find-me and eat-me signals in apoptotic cell clearance: progress and conundrums. *J. Exp. Med.* 207:1807-1817, 2010.
47. Russell J, Cooper D, Tailor A, Stokes K Y, Granger D N: Low venular shear rates promote leukocyte-dependent recruitment of adherent platelets. *Am. J. Physiol. Gastrointest. Liver Physiol.* 284:G123-129, 2003.
48. Schaeffer E M, Schwartzberg P L. Tec family kinases in lymphocyte signaling and function. *Curr. Opin Immunol.* 12:282-288, 2000.
49. Shasby D M, Vanbenthuysen K M, Tate R M, Shasby S S, McMurty I, Repine J E. Granulocytes mediate acute edematous lung injury in rabbits and in isolated rabbit lungs perfused with phorbol myristate acetate: Role of oxygen radicals. *Am. Rev. Respir. Dis.* 125:443-447, 1982.
50. Stokes K Y, Gurwara S, Granger D N. T-cell derived interferon-gamma contributes to arteriolar dysfunction during acute hypercholesterolemia. *Arterioscler. Thromb. Vasc. Biol.* 27:1998-2004, 2007.
51. Tanino Y, Coombe D R, Gill S E, Kett W C, Kajikawa O, Proudfoot A E, Wells T N, Parks W C, Wight T N, Martin T R, Frevert C W. Kinetics of chemokine-glycosaminoglycan interactions control neutrophil migration into the airspaces of the lungs. *J. Immunol.* 184:2677-2685, 2010.
52. Ware L B, Fang X, Matthay M A. Protein C and thrombomodulin in human acute lung injury. *Am. J. Physiol. Lung Cell. Mol. Physiol.* 285:L514-521, 2003.
53. Weiland J E, Davis W B, Holter J F, Mohammed J R, Dorinsky P M, Gadek J E. Lung neutrophils in the adult respiratory distress syndrome. Clinical and pathological significance. *Am. Rev. Respir. Dis.* 133:218-225, 1986.
54. Welch E J, Naikawadi R P, Li Z, Lin P, Ishii S, Shimizu T, Tiruppathi C, Du X, Subbaiah P V, Ye R D. Opposing effects of platelet-activating factor and lyso-platelet-activating factor on neutrophil and platelet activation. *Mol. Pharmacol.* 75:227-234, 2009.
55. Zemans R L, Arndt P G. Tec kinases regulate actin assembly and cytokine expression in LPS-stimulated human neutrophils via JNK activation. *Cell. Immunol.* 258:90-97, 2009.
56. Yago T, Shao B, Miner J J, Yao L, Klopocki A G, Maeda K, Coggeshall K M, McEver R P. E-selectin engages PSGL-1 and CD44 through a common signaling pathway to induce integrin alphaLbeta2-mediated slow leukocyte rolling. *Blood* 116:485-494, 2010.
57. Yang K Y, Arcaroli J J, Abraham E. Early alterations in neutrophil activation are associated with outcome in acute lung injury. *Am. J. Respir. Crit. Care Med.* 167:1567-1574, 2003.

The references cited above in the numbered list as well as those in the body of the text are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method for inhibiting Bruton's tyrosine kinase (Btk) activity in alveolar neutrophils in the lungs of a subject in need of such inhibiting, comprising providing to the neutrophils in the lungs of the subject, by inhalation, intranasal administration or lung instillation, an effective amount of a Btk inhibitor that is:
   (a) a combination of three siRNA molecules each of which:
      (i) is between about 10 and about 31 nucleotides in length;
      (ii) binds specifically to a complementary target Btk nucleotide sequence, or
   (b) a small organic molecule inhibitor of Btk,
   wherein said siRNA molecules and said small molecule inhibitor are targeted to said alveolar neutrophils by a neutrophil-specific antibody or an antigen-binding fragment or derivative thereof that is conjugated to said siRNAs or to said small organic molecule inhibitor.

2. A method for treating symptoms of a lung disease or disorder that is mediated by alveolar neutrophils and results from activation or activity of Btk in the lungs of a subject, comprising delivering to the alveolar neutrophils in the lungs of said subject in need of such treatment, by inhalation, intranasal administration or lung instillation, an effective amount of a Btk inhibitor that is:
   (a) three siRNA molecules, each of which
      (i) is between about 10 and about 31 nucleotides in length;
      (ii) binds specifically to a complementary Btk nucleotide target sequence, or
   (b) a small organic molecule inhibitor of Btk,
   wherein both said siRNA molecules and said small molecule inhibitor are targeted to said alveolar neutrophils by a neutrophil-specific antibody or an antigen-binding fragment or derivative thereof that is conjugated to said siRNAs or to said small organic molecule inhibitor, and
   wherein the lung disease or disorder is selected from the group consisting of acute lung injury, acute respiratory distress syndrome, emphysema, chronic obstructive pulmonary disease, acute bacterial lung infection, acute viral lung infection and cystic fibrosis.

3. The method according to claim 1, wherein the conjugated siRNAs or the small organic molecule Btk inhibitor are administered intranasally.

4. The method according to claim 2, wherein the conjugated siRNAs or the small organic molecule Btk inhibitor are administered intranasally.

5. The method according to claim 1 wherein the antibody, fragment or derivative is specific for a neutrophil surface antigen selected from the group consisting of CD66b/CD67 and CD177.

6. The method according to claim 2 wherein the antibody, fragment or derivative is specific for a neutrophil surface antigen selected from the group consisting of CD66b/CD67 and CD177.

7. The method according to claim 1 wherein the small organic molecule Btk inhibitor is selected from the group consisting of Ibrutinib/PCI-32765, AVL-101, AVL 291; AVL-292; Dasatinib; LFM-A13; and GDC-0834.

8. The method according to claim 2 wherein the small organic molecule Btk inhibitor is selected from the group consisting of Ibrutinib/PCI-32765; AVL-101; AVL-291; AVL-292; Dasatinib; LFM-A13; and GDC-0834.

9. The method according to claim 1, wherein three Btk target sequences which the siRNAs target are any three of the sequences SEQ ID NO:5, SEQ ID NO:6, SEQ ID NO:7, SEQ ID NO:8, SEQ ID NO:9, SEQ ID NO:10 or SEQ ID NO:11.

10. The method according to claim 2, wherein three Btk target sequences which the siRNAs target are any three of the sequences SEQ ID NO:5, SEQ ID NO:6, SEQ ID NO:7, SEQ ID NO:8, SEQ ID NO:9, SEQ ID NO:10 or SEQ ID NO:11.

11. The method according to claim 1, wherein the siRNAs are ds RNA molecules.

12. The method according to claim 2, wherein the siRNAs are ds RNA molecules.

13. The method according to claim 1, wherein the siRNAs comprise any three of the antisense sequences selected from the group consisting of SEQ ID NO:13, SEQ ID NO:15, SEQ ID NO:17, SEQ ID NO:19, SEQ ID NO:21, SEQ ID NO:23 and SEQ ID NO:25.

14. The method according to any of claims 2, wherein the siRNAs comprise any three of the antisense sequences selected from the group consisting of SEQ ID NO:13, SEQ ID NO:15, SEQ ID NO:17, SEQ ID NO:19, SEQ ID NO:21, SEQ ID NO:23 and SEQ ID NO:25.

15. The method according to claim 1, wherein the Btk target sequences targeted by the three siRNAs are sequences SEQ ID NO:8, SEQ ID NO:9 and SEQ ID NO:10.

16. The method according to claim 2, wherein the Btk target sequences targeted by the three siRNAs are sequences SEQ ID NO:8, SEQ ID NO:9 and SEQ ID NO:10.

17. The method according to claim 1, the three siRNAs comprise the antisense sequences of SEQ ID NO:19, SEQ ID NO:21 and SEQ ID NO:23.

18. The method according to claim 2, the three siRNAs comprise the antisense sequences of SEQ ID NO:19, SEQ ID NO:21 and SEQ ID NO:23.

* * * * *

SEQUENCE LISTING

```
<160> NUMBER OF SEQ ID NOS: 27

<210> SEQ ID NO 1
<211> LENGTH: 1707
<212> TYPE: DNA
<213> ORGANISM: Homo sapiens

<400> SEQUENCE: 1
atggccgcag tgattctgga gagcatcttt ctgaagcgat cccaacagaa aaagaaaaca      60
tcacctctaa acttcaagaa gcgcctgttt ctcttgaccg tgcacaaact ctcctactat     120
gagtatgact ttgaacgtgg gagaagaggc agtaagaagg gttcaataga tgttgagaag     180
atcacttgtg ttgaaacagt ggttcctgaa aaaaatcctc ctccagaaag acagattccg     240
agaagaggtg aagagtccag tgaaatggag caaatttcaa tcattgaaag gttcccttat     300
cccttccagg ttgtatatga tgaagggcct ctctacgtct tctccccaac tgaagaacta     360
aggaagcggt ggattcacca gctcaaaaac gtaatccggt acaacagtga tctggttcag     420
aaatatcacc cttgcttctg gatcgatggg cagtatctct gctgctctca gacagccaaa     480
aatgctatgg gctgccaaat tttggagaac aggaatggaa gcttaaaacc tgggagttct     540
caccggaaga caaaaaagcc tcttccccca acgcctgagg aggaccagat cttgaaaaag     600
ccactaccgc ctgagccagc agcagcacca gtctccacaa gtgagctgaa aaaggttgtg     660 gcccttatg attacatgcc aatgaatgca aatgatctac agctgcggaa gggtgatgaa     720
```

| | | |
|---|---|---|
| tattttatct tggaggaaag caacttacca tggtggagag cacgagataa aaatgggcag | 780 | |
| gaaggctaca ttcctagtaa ctatgtcact gaagcagaag actccataga aatgtatgag | 840 | |
| tggtattcca aacacatgac tcggagtcag gctgagcaac tgctaaagca agaggggaaa | 900 | |
| gaaggaggtt tcattgtcag agactccagc aaagctggca aatatacagt gtctgtgttt | 960 | |
| gctaaatcca caggggaccc tcaaggggtg atacgtcatt atgttgtgtg ttccacacct | 1020 | |
| cagagccagt attacctggc tgagaagcac cttttcagca ccatccctga gctcattaac | 1080 | |
| taccatcagc acaactctgc aggactcata tccaggctca aatatccagt gtctcaacaa | 1140 | |
| aacaagaatg caccttccac tgcaggcctg ggatacggat catgggaaat tgatccaaag | 1200 | |
| gacctgacct tcttgaagga gctggggact ggacaatttg gggtagtgaa gtatgggaaa | 1260 | |
| tggagaggcc agtacgacgt ggccatcaag atgatcaaag aaggctccat gtctgaagat | 1320 | |
| gaattcattg aagaagccaa agtcatgatg aatctttccc atgagaagct ggtgcagttg | 1380 | |
| tatggcgtct gcaccaagca gcgccccatc ttcatcatca ctgagtacat ggccaatggc | 1440 | |
| tgcctcctga actacctgag ggagatgcgc accgcttcc agactcagca gctgctagag | 1500 | |
| atgtgcaagg atgtctgtga agccatggaa tacctggagt caaagcagtt ccttcaccga | 1560 | |
| gacctggcag ctcgaaactg tttggtaaac gatcaaggag ttgttaaagt atctgatttc | 1620 | |
| ggcctgtcca ggtatgtcct ggatgatgaa tacacaagct cagtaggctc caaatttcca | 1680 | |
| gtccggtggt ccccaccgga gtcctga | 1707 | |

<210> SEQ ID NO 2
<211> LENGTH: 568
<212> TYPE: PRT
<213> ORGANISM: Homo sapiens

<400> SEQUENCE: 2

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala

```
                195                 200                 205
Ala Pro Val Ser Thr Ser Glu Leu Lys Lys Val Ala Leu Tyr Asp
210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
                260                 265                 270

Glu Asp Ser Ile Glu Met Tyr Glu Trp Tyr Ser Lys His Met Thr Arg
            275                 280                 285

Ser Gln Ala Glu Gln Leu Leu Lys Gln Glu Gly Lys Glu Gly Gly Phe
            290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
                340                 345                 350

Ser Thr Ile Pro Glu Leu Ile Asn Tyr His Gln His Asn Ser Ala Gly
            355                 360                 365

Leu Ile Ser Arg Leu Lys Tyr Pro Val Ser Gln Gln Asn Lys Asn Ala
370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
                420                 425                 430

Lys Glu Gly Ser Met Ser Glu Asp Glu Phe Ile Glu Glu Ala Lys Val
            435                 440                 445

Met Met Asn Leu Ser His Glu Lys Leu Val Gln Leu Tyr Gly Val Cys
450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
            515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Ser
                565

<210> SEQ ID NO 3
<211> LENGTH: 1980
<212> TYPE: DNA
<213> ORGANISM: Mus musculus

<400> SEQUENCE: 3
```

```
atggctgcag tgatactgga gagcatcttt ctgaagcgct cccagcagaa aaagaaaaca        60
tcacctttaa acttcaagaa gcgcctgttt ctcttgactg tacacaaact ttcatactat       120
gaatatgact ttgaacgtgg gagaagaggc agtaagaaag gttcaataga tgttgagaag       180
atcacctgtg ttgaaacagt aattcctgaa aaaaatcccc caccagaaag acagattccg       240
aggagaggtg aggagtctag tgaaatggaa cagatttcaa tcattgaaag gttcccgtac       300
ccattccagg ttgtatatga tgaaggacct ctctatgttt ctcccccaac tgaagagctg       360
agaaagcgct ggattcacca gctcaaaaat gtaatccggt acaatagtga cctggtacag       420
aaataccatc cttgcttctg gattgatgga cagtatctct gctgctctca gacagccaag       480
aatgctatgg gctgccaaat tttggagaac aggaatggaa gcttaaaacc tgggagttct       540
catcgaaaaa cgaaaaagcc tcttccccct accccagagg aagatcagat cttgaaaaaa       600
ccgcttcccc cggagccaac agcagcacca atctccacaa ccgagctgaa aaaggtcgtg       660
gcccttatg attacatgcc aatgaacgca atgacttac aattgcgaaa gggcgaggag        720
tattttatcc tggaggagag caacctaccg tggtggcgag cacgagataa aaatgggcag       780
gaaggctaca tcccaagtaa ctatatcact gaagctgagg actccataga gatgtatgag       840
tggtattcca agcacatgac tcgaagtcaa gctgagcaac tgctaaagca gaggggaaa        900
gaaggaggtt tcattgtcag agactccagc aaagctggaa atacaccgt gtctgtgttt        960
gctaaatcta ctggggagcc tcaagggggtg atccgccatt acgttgtgtg ttccacgcca      1020
cagagccagt attacctggc tgagaaacac ctcttcagca ccatccctga gctcattaac      1080
taccatcaac acaactctgc aggcctcata tccaggctga aatatcctgt gtctaaacaa      1140
aacaaaaacg cgccttctac tgcaggcctg ggctatggat catgggaaat tgatccaaag      1200
gacctcacct tcttgaagga gcttgggact ggacaattcg gtgtcgtgaa atatgggaag      1260
tggaggggcc aatatgatgt ggccatcaag atgatcagag aaggttccat gtcggaggat      1320
gaattcattg aagaagccaa agtcatgatg aatctttccc atgagaagct ggtgcagttg      1380
tatggcgtct gcaccaaaca acgccccatc ttcatcatca ccgagtacat ggctaatggc      1440
tgcctcttga actacctgag ggagatgcgg caccgcttcc agacacagca gctgcttgag      1500
atgtgcaaag atgtctgtga agcaatggaa tacttggagt cgaagcagtt ccttcacaga      1560
gacctggcag ctcgaaactg tttggtaaac gatcaaggag ttgtgaaagt atctgacttt      1620
ggcctgtcta ggtatgtcct tgatgatgag tacaccagct ctgtaggctc caagtttcca      1680
gtccggtggt ctccaccaga agtgcttatg tatagcaagt tcagcagcaa atctgacatc      1740
tgggcttttg gggttttaat gtgggagatc tactccctgg ggaagatgcc gtatgagaga      1800
tttactaaca gtgagacagc agaacacatt gctcaaggct acgtctctta caggcctcat      1860
ctggcatcag agagggtata taccatcatg tacagctgct ggcacgagaa agcagatgaa      1920
cgtcctagtt tcaaaattct cttgagtaac attctagatg tgatggatga agaatcctga     1980
```

<210> SEQ ID NO 4
<211> LENGTH: 659
<212> TYPE: PRT
<213> ORGANISM: Mus musculus

<400> SEQUENCE: 4

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

-continued

```
Thr Val His Lys Leu Ser Tyr Glu Tyr Asp Phe Glu Arg Gly Arg
        35                  40                  45
Arg Gly Ser Lys Lys Gly Ser Ile Asp Val Glu Lys Ile Thr Cys Val
 50                  55                  60
Glu Thr Val Ile Pro Lys Asn Pro Pro Glu Arg Gln Ile Pro
 65                  70                  75                  80
Arg Arg Gly Glu Glu Ser Ser Glu Met Glu Gln Ile Ser Ile Glu
                     85                  90                  95
Arg Phe Pro Tyr Pro Phe Gln Val Val Tyr Asp Glu Gly Pro Leu Tyr
                100                 105                 110
Val Phe Ser Pro Thr Glu Glu Leu Arg Lys Arg Trp Ile His Gln Leu
         115                 120                 125
Lys Asn Val Ile Arg Tyr Asn Ser Asp Leu Val Gln Lys Tyr His Pro
 130                 135                 140
Cys Phe Trp Ile Asp Gly Gln Tyr Leu Cys Cys Ser Gln Thr Ala Lys
145                 150                 155                 160
Asn Ala Met Gly Cys Gln Ile Leu Glu Asn Arg Asn Gly Ser Leu Lys
                165                 170                 175
Pro Gly Ser Ser His Arg Lys Thr Lys Lys Pro Leu Pro Pro Thr Pro
                180                 185                 190
Glu Glu Asp Gln Ile Leu Lys Lys Pro Leu Pro Glu Pro Thr Ala
        195                 200                 205
Ala Pro Ile Ser Thr Thr Glu Leu Lys Lys Val Val Ala Leu Tyr Asp
 210                 215                 220
Tyr Met Pro Met Asn Ala Asn Asp Leu Gln Leu Arg Lys Gly Glu Glu
225                 230                 235                 240
Tyr Phe Ile Leu Glu Glu Ser Asn Leu Pro Trp Trp Arg Ala Arg Asp
                245                 250                 255
Lys Asn Gly Gln Glu Gly Tyr Ile Pro Ser Asn Tyr Ile Thr Glu Ala
                260                 265                 270
Glu Asp Ser Ile Glu Met Tyr Glu Trp Tyr Ser Lys His Met Thr Arg
        275                 280                 285
Ser Gln Ala Glu Gln Leu Leu Lys Gln Glu Gly Lys Glu Gly Gly Phe
 290                 295                 300
Ile Val Arg Asp Ser Ser Lys Ala Gly Lys Tyr Thr Val Ser Val Phe
305                 310                 315                 320
Ala Lys Ser Thr Gly Glu Pro Gln Gly Val Ile Arg His Tyr Val Val
                325                 330                 335
Cys Ser Thr Pro Gln Ser Gln Tyr Tyr Leu Ala Glu Lys His Leu Phe
                340                 345                 350
Ser Thr Ile Pro Glu Leu Ile Asn Tyr His Gln His Asn Ser Ala Gly
        355                 360                 365
Leu Ile Ser Arg Leu Lys Tyr Pro Val Ser Lys Gln Asn Lys Asn Ala
 370                 375                 380
Pro Ser Thr Ala Gly Leu Gly Tyr Gly Ser Trp Glu Ile Asp Pro Lys
385                 390                 395                 400
Asp Leu Thr Phe Leu Lys Glu Leu Gly Thr Gly Gln Phe Gly Val Val
                405                 410                 415
Lys Tyr Gly Lys Trp Arg Gly Gln Tyr Asp Val Ala Ile Lys Met Ile
                420                 425                 430
Arg Glu Gly Ser Met Ser Glu Asp Glu Phe Ile Glu Glu Ala Lys Val
        435                 440                 445
```

```
Met Met Asn Leu Ser His Glu Lys Leu Val Gln Leu Tyr Gly Val Cys
    450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
        515                 520                 525

Val Asn Asp Gln Gly Val Val Lys Val Ser Asp Phe Gly Leu Ser Arg
    530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
            580                 585                 590

Leu Gly Lys Met Pro Tyr Glu Arg Phe Thr Asn Ser Glu Thr Ala Glu
        595                 600                 605

His Ile Ala Gln Gly Leu Arg Leu Tyr Arg Pro His Leu Ala Ser Glu
    610                 615                 620

Arg Val Tyr Thr Ile Met Tyr Ser Cys Trp His Glu Lys Ala Asp Glu
625                 630                 635                 640

Arg Pro Ser Phe Lys Ile Leu Leu Ser Asn Ile Leu Asp Val Met Asp
                645                 650                 655

Glu Glu Ser

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
ttggtaaacg atcaaggag                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
gggaaagaag gaggtttca                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
gaagcttaaa acctgggag                                                19

<210> SEQ ID NO 8
```

```
<211> LENGTH: 25
<212> TYPE: DNA
<213> ORGANISM: Artificial Sequence
<220> FEATURE:
<223> OTHER INFORMATION: Synthetic

<400> SEQUENCE: 8
ccctttatga ttacatgcca atgaa                                           25

<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9
gcaccatccc tgagctcatt aacta                                           25

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
ggacaattcg gtgtcgtgaa atatg                                           25

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
ggacaatttg gggtagtgaa gtatg                                           25

<210> SEQ ID NO 12
<211> LENGTH: 21
<212> TYPE: RNA
<213> ORGANISM: Artificial Sequence
<220> FEATURE:
<223> OTHER INFORMATION: Synthetic

<400> SEQUENCE: 12
uugguaaacg aucaaggagu u                                               21

<210> SEQ ID NO 13
<211> LENGTH: 21
<212> TYPE: RNA
<213> ORGANISM: Artificial Sequence
<220> FEATURE:
<223> OTHER INFORMATION: Synthetic

<400> SEQUENCE: 13
cuccuugauc guuuaccaau u                                               21

<210> SEQ ID NO 14
<211> LENGTH: 21
<212> TYPE: RNA
<213> ORGANISM: Artificial Sequence
<220> FEATURE:
<223> OTHER INFORMATION: Synthetic

<400> SEQUENCE: 14
```

```
gggaaagaag gagguuucau u                                              21

<210> SEQ ID NO 15
<211> LENGTH: 20
<212> TYPE: RNA
<213> ORGANISM: Artificial Sequence
<220> FEATURE:
<223> OTHER INFORMATION: Synthetic

<400> SEQUENCE: 15
ugaaccuccu ucuuucccuu                                                20

<210> SEQ ID NO 16
<211> LENGTH: 21
<212> TYPE: RNA
<213> ORGANISM: Artificial Sequence
<220> FEATURE:
<223> OTHER INFORMATION: Synthetic

<400> SEQUENCE: 16
gaagcuuaaa accugggagu u                                              21

<210> SEQ ID NO 17
<211> LENGTH: 21
<212> TYPE: RNA
<213> ORGANISM: Artificial Sequence
<220> FEATURE:
<223> OTHER INFORMATION: Synthetic

<400> SEQUENCE: 17
cucccaccuu uuaagcuucu u                                              21

<210> SEQ ID NO 18
<211> LENGTH: 25
<212> TYPE: RNA
<213> ORGANISM: Artificial Sequence
<220> FEATURE:
<223> OTHER INFORMATION: Synthetic

<400> SEQUENCE: 18
cccuuuauga uuacaugcca augaa                                          25

<210> SEQ ID NO 19
<211> LENGTH: 25
<212> TYPE: RNA
<213> ORGANISM: Artificial Sequence
<220> FEATURE:
<223> OTHER INFORMATION: Synthetic

<400> SEQUENCE: 19
gggaaauacu aauguacggu uacuu                                          25

<210> SEQ ID NO 20
<211> LENGTH: 25
<212> TYPE: RNA
<213> ORGANISM: Artificial Sequence
<220> FEATURE:
<223> OTHER INFORMATION: Synthetic

<400> SEQUENCE: 20
gcaccauccc ugagcucauu aacua                                          25

<210> SEQ ID NO 21
<211> LENGTH: 25
<212> TYPE: RNA
```

```
<213> ORGANISM: Artificial Sequence
<220> FEATURE:
<223> OTHER INFORMATION: Synthetic

<400> SEQUENCE: 21
cgugguaggg acucgaguaa uugau                                          25

<210> SEQ ID NO 22
<211> LENGTH: 25
<212> TYPE: RNA
<213> ORGANISM: Artificial Sequence
<220> FEATURE:
<223> OTHER INFORMATION: Synthetic

<400> SEQUENCE: 22
ggacaauucg gugucgugaa auaug                                          25

<210> SEQ ID NO 23
<211> LENGTH: 25
<212> TYPE: RNA
<213> ORGANISM: Artificial Sequence
<220> FEATURE:
<223> OTHER INFORMATION: Synthetic

<400> SEQUENCE: 23
ccuguuaagc cacagcacuu uauac                                          25

<210> SEQ ID NO 24
<211> LENGTH: 25
<212> TYPE: RNA
<213> ORGANISM: Artificial Sequence
<220> FEATURE:
<223> OTHER INFORMATION: Synthetic

<400> SEQUENCE: 24
ggacaauuug ggguagugaa guaug                                          25

<210> SEQ ID NO 25
<211> LENGTH: 25
<212> TYPE: RNA
<213> ORGANISM: Artificial Sequence
<220> FEATURE:
<223> OTHER INFORMATION: Synthetic

<400> SEQUENCE: 25
ccuguuaaac cccaucacuu cauac                                          25

<210> SEQ ID NO 26
<211> LENGTH: 25
<212> TYPE: RNA
<213> ORGANISM: Artificial Sequence
<220> FEATURE:
<223> OTHER INFORMATION: Synthetic

<400> SEQUENCE: 26
uuccucucca cgcgcaguac auuua                                          25

<210> SEQ ID NO 27
<211> LENGTH: 25
<212> TYPE: RNA
```

```
<213> ORGANISM: Artificial Sequence
<220> FEATURE:
<223> OTHER INFORMATION: Synthetic

<400> SEQUENCE: 27
aaggagaggu gcgcgucaug uaaau                                          25
```